(12) United States Patent
Anryu et al.

(10) Patent No.: US 9,260,407 B2
(45) Date of Patent: Feb. 16, 2016

(54) SALT AND PHOTORESIST COMPOSITION COMPRISING THE SAME

(75) Inventors: Yukako Anryu, Osaka (JP); Koji Ichikawa, Osaka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 125 days.

(21) Appl. No.: 13/295,943

(22) Filed: Nov. 14, 2011

(65) Prior Publication Data

US 2012/0122032 A1 May 17, 2012

(30) Foreign Application Priority Data

| Nov. 15, 2010 | (JP) | ................................ 2010-254541 |
| Apr. 6, 2011 | (JP) | ................................ 2011-084367 |
| Sep. 7, 2011 | (JP) | ................................ 2011-194759 |

(51) Int. Cl.

| G03F 7/004 | (2006.01) |
|---|---|
| C07D 327/02 | (2006.01) |
| C07D 327/04 | (2006.01) |
| C07D 327/06 | (2006.01) |
| C07D 333/46 | (2006.01) |
| C07D 335/02 | (2006.01) |
| C07D 337/04 | (2006.01) |
| C07C 303/32 | (2006.01) |
| C07C 309/04 | (2006.01) |
| C07C 309/06 | (2006.01) |
| C07C 309/12 | (2006.01) |
| C07C 309/17 | (2006.01) |
| C07C 309/19 | (2006.01) |
| G03F 7/039 | (2006.01) |
| G03F 7/38 | (2006.01) |
| G03F 7/20 | (2006.01) |

(52) U.S. Cl.
CPC ............ *C07D 327/02* (2013.01); *C07C 303/32* (2013.01); *C07D 327/04* (2013.01); *C07D 327/06* (2013.01); *C07D 333/46* (2013.01); *C07D 335/02* (2013.01); *C07D 337/04* (2013.01); *G03F 7/0045* (2013.01); *G03F 7/0046* (2013.01); *G03F 7/0392* (2013.01); *G03F 7/0397* (2013.01); *C07C 309/04* (2013.01); *C07C 309/06* (2013.01); *C07C 309/12* (2013.01); *C07C 309/17* (2013.01); *C07C 309/19* (2013.01); *G03F 7/2041* (2013.01); *G03F 7/38* (2013.01)

(58) Field of Classification Search
CPC ... G03F 7/0045; G03F 7/0046; G03F 7/0397; G03F 7/38; G03F 7/2041; C07D 335/02; C07D 327/02; C07D 327/04; C07D 327/06; C07D 333/46; C07D 337/04; C07C 309/04; C07C 309/17; C07C 309/19; C07C 309/06; C07C 309/12; C07C 303/32

USPC ............ 430/270.1, 921, 922; 549/13, 10, 14, 549/28, 30, 62; 562/109, 113, 110; 560/149
See application file for complete search history.

(56) References Cited

U.S. PATENT DOCUMENTS

| 3,779,778 A | 12/1973 | Smith et al. |
| 3,849,137 A | 11/1974 | Barzynski et al. |
| 4,576,902 A | 3/1986 | Saenger et al. |
| 4,822,716 A | 4/1989 | Onishi et al. |
| 4,857,437 A | 8/1989 | Banks et al. |
| 5,017,453 A | 5/1991 | Onishi et al. |
| 5,073,476 A | 12/1991 | Meier et al. |
| 5,198,520 A | 3/1993 | Onishi et al. |
| 5,260,410 A | 11/1993 | Schwalm |
| 5,453,341 A | 9/1995 | Schwalm |
| 5,663,035 A | 9/1997 | Masuda et al. |
| 7,304,175 B2 | 12/2007 | Harada et al. |

(Continued)

FOREIGN PATENT DOCUMENTS

| DE | 3914407 A1 | 10/1990 |
| EP | 0126712 A1 | 11/1984 |

(Continued)

OTHER PUBLICATIONS

Luis et al., "Non Concerted Pathways in the Generation of Dehydroarenes by Thermal Decomposition of Diaryliodonium Carboxylates", Tetrahedron, vol. 45, No. 19, 1989, pp. 6281-6296.

(Continued)

*Primary Examiner* — John S Chu
(74) *Attorney, Agent, or Firm* — Birch, Stewart, Kolasch & Birch, LLP

(57) ABSTRACT

The present invention provides a salt represented by the formula (I):

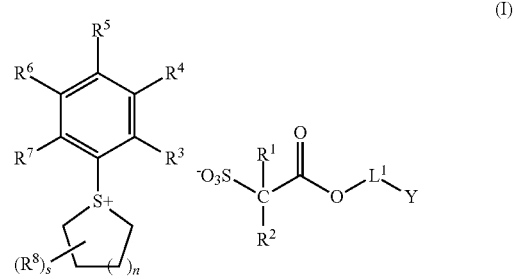

wherein $R^1$, $R^2$, $L^1$, Y, $R^3$, $R^4$, $R^5$, $R^6$, $R^7$, n, s, and $R^8$ represent variables outlined in the specification.

8 Claims, No Drawings

(56) References Cited

U.S. PATENT DOCUMENTS

| | | | |
|---|---|---|---|
| 7,439,006 B2 | 10/2008 | Yoshida et al. | |
| 7,531,686 B2 * | 5/2009 | Harada | C07C 309/12 430/270.1 |
| 7,575,850 B2 | 8/2009 | Takata et al. | |
| 7,579,132 B2 | 8/2009 | Harada et al. | |
| 7,612,217 B2 | 11/2009 | Sakamoto et al. | |
| 8,039,200 B2 | 10/2011 | Kodama | |
| 8,124,803 B2 | 2/2012 | Yoshida et al. | |
| 8,206,886 B2 | 6/2012 | Kodama | |
| 8,703,387 B2 * | 4/2014 | Kawaue et al. | 430/270.1 |
| 8,921,029 B2 * | 12/2014 | Ichikawa et al. | 430/270.1 |
| 2005/0209224 A1 | 9/2005 | Singh et al. | |
| 2005/0266336 A1 | 12/2005 | Kodama | |
| 2006/0194982 A1 | 8/2006 | Harada et al. | |
| 2007/0027336 A1 | 2/2007 | Yoshida et al. | |
| 2007/0100158 A1 | 5/2007 | Harada et al. | |
| 2008/0044738 A1 | 2/2008 | Harada et al. | |
| 2008/0076063 A1 | 3/2008 | Yoshida et al. | |
| 2008/0081293 A1 * | 4/2008 | Harada et al. | 430/287.1 |
| 2008/0081925 A1 | 4/2008 | Sakamoto et al. | |
| 2008/0090171 A1 * | 4/2008 | Irie et al. | 430/270.1 |
| 2008/0193874 A1 | 8/2008 | Takata et al. | |
| 2009/0023095 A1 | 1/2009 | Hada et al. | |
| 2009/0068591 A1 | 3/2009 | Kawaue et al. | |
| 2009/0197204 A1 | 8/2009 | Shiono et al. | |
| 2009/0202945 A1 | 8/2009 | Nakagawa et al. | |
| 2009/0317745 A1 | 12/2009 | Mimura et al. | |
| 2010/0009288 A1 | 1/2010 | Kato et al. | |
| 2010/0035185 A1 | 2/2010 | Hagiwara et al. | |
| 2010/0081088 A1 | 4/2010 | Kawaue et al. | |
| 2010/0203446 A1 | 8/2010 | Ichikawa et al. | |
| 2010/0304300 A1 | 12/2010 | Kodama | |
| 2011/0020749 A1 | 1/2011 | Ichikawa et al. | |
| 2011/0053082 A1 | 3/2011 | Ichikawa et al. | |
| 2011/0111343 A1 * | 5/2011 | Hirano et al. | 430/270.1 |
| 2011/0171576 A1 | 7/2011 | Yamaguchi et al. | |
| 2011/0200935 A1 | 8/2011 | Masuyama et al. | |
| 2011/0201823 A1 | 8/2011 | Yoshida et al. | |
| 2012/0015297 A1 * | 1/2012 | Komuro et al. | 430/283.1 |
| 2012/0015299 A1 | 1/2012 | Komuro et al. | |
| 2012/0028188 A1 | 2/2012 | Ichikawa et al. | |
| 2012/0052443 A1 | 3/2012 | Masuyama et al. | |
| 2012/0088190 A1 | 4/2012 | Ichikawa et al. | |
| 2012/0100483 A1 | 4/2012 | Masuyama et al. | |
| 2012/0100487 A1 * | 4/2012 | Hirano et al. | 430/325 |
| 2012/0135350 A1 | 5/2012 | Kobayashi et al. | |
| 2012/0156620 A1 | 6/2012 | Ichikawa et al. | |
| 2012/0237875 A1 | 9/2012 | Asano et al. | |

FOREIGN PATENT DOCUMENTS

| | | |
|---|---|---|
| JP | 55-164824 A | 12/1980 |
| JP | 62-69263 A | 3/1987 |
| JP | 62-153853 A | 7/1987 |
| JP | 63-26653 A | 2/1988 |
| JP | 63-146029 A | 6/1988 |
| JP | 63-146038 A | 6/1988 |
| JP | 63-163452 A | 7/1988 |
| JP | 11-52575 A | 2/1999 |
| JP | 2005-221721 A | 8/2005 |
| JP | 2006-257078 A | 9/2006 |
| JP | 2007-57670 A | 3/2007 |
| JP | 2007-514775 A | 6/2007 |
| JP | 2007-224008 A | 9/2007 |
| JP | 2008-13551 A | 1/2008 |
| JP | 2008-69146 A | 3/2008 |
| JP | 2008-127367 A | 6/2008 |
| JP | 2008-209917 A | 9/2008 |
| JP | 2009-145408 A | 7/2009 |
| JP | 2009-229603 A | 10/2009 |
| JP | 2010-26478 A | 2/2010 |
| JP | 2010-61018 A | 3/2010 |
| JP | 2010-111660 A | 5/2010 |
| JP | 2010-152341 A | 7/2010 |
| JP | 2010-197413 A | 9/2010 |
| JP | 2010-204646 A | 9/2010 |
| JP | 2011-113034 A | 6/2011 |
| JP | 2011-128226 A | 6/2011 |
| WO | WO 2008/099869 A1 | 8/2008 |
| WO | WO 2011/034176 A1 | 3/2011 |

OTHER PUBLICATIONS

U.S. Office Action dated Apr. 26, 2013 for U.S. Appl. No. 13/551,906.

U.S. Restriction Requirement dated Oct. 4, 2013 for U.S. Appl. No. 13/551,807.

The Office Action (including an English translation), dated Apr. 28, 2015, issued in the corresponding Japanese Patent Application No. 2011-194759.

The Office Action (including an English translation), dated May 8, 2015, issued in the corresponding Taiwanese Patent Application No. 100141221.

* cited by examiner

SALT AND PHOTORESIST COMPOSITION COMPRISING THE SAME

This nonprovisional application claims priority under 35 U.S.C. §119(a) on Patent Application No. 2010-254541 filed in JAPAN on Nov. 15, 2010, on Patent Application No. 2011-084367 filed in JAPAN on Apr. 6, 2011, and on Patent Application No. 2011-194759 filed in JAPAN on Sep. 7, 2011, the entire contents of which are hereby incorporated by reference.

FIELD OF THE INVENTION

The present invention relates to a salt and a photoresist composition comprising the same.

BACKGROUND OF THE INVENTION

A photoresist composition is used for semiconductor microfabrication employing a lithography process.

JP 2007-057670 A discloses a photoresist composition comprising a salt represented by the following formula:

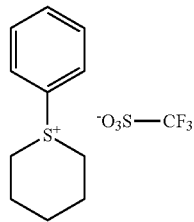

as an acid generator.

SUMMARY OF THE INVENTION

The present invention is to provide a salt for suitable for an acid generator and a photoresist composition comprising the same.

The present invention relates to the followings:

<1> A salt represented by the formula (I):

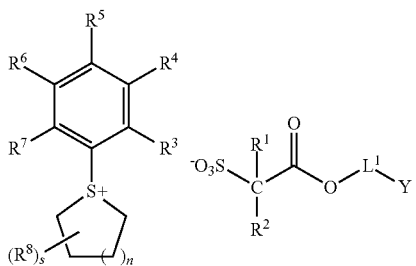

wherein $R^1$ and $R^2$ independently each represent a fluorine atom or a C1-C6 perfluoroalkyl group, $L^1$ represents a single bond, a C1-C6 alkanediyl group, a C4-C8 divalent alicyclic hydrocarbon group, —$(CH_2)_t$—CO—O—* or —$(CH_2)_t$—CO—O—$CH_2$—$(CH_2)_u$—*, one or more —$CH_2$— in the alkanediyl group and —$(CH_2)_u$— can be replaced by —O—, t represents an integer of 1 to 12, u represents an integer of 0 to 12, * represents a binding position to Y, Y represents a C3-C18 monovalent alicyclic hydrocarbon group which can have one or more substituents, and one or more —$CH_2$— in the monovalent alicyclic hydrocarbon group can be replaced by —O—, —CO— or —$SO_2$—, $R^3$, $R^4$, $R^5$, $R^6$ and $R^7$ each independently represent a hydrogen atom, a hydroxyl group, a C1-C6 alkyl group, a C1-C6 alkoxy group, a C2-C7 alkoxycarbonyl group or a C2-C12 acyloxy group, and one or more —$CH_2$— in the alicycle containing $S^+$ can be replaced by —O— or —CO—, n represents an integer of 1 to 3, s represents an integer of 0 to 3, and $R^8$ is independently in each occurrence a C1-C6 alkyl group;

<2> The salt according to <1>, wherein $L^1$ is a single bond or a methylene group;

<3> An acid generator comprising the salt according to <1> or <2>;

<4> A photoresist composition comprising the acid generator according to <3> and a resin having an acid-labile group, being insoluble or poorly soluble in an aqueous alkali solution but becoming soluble in an aqueous alkali solution by the action of an acid;

<5> The photoresist composition according to <4>, which further comprises a basic compound;

<6> A process for producing a photoresist pattern comprising the following steps (1) to (5):

(1) a step of applying the photoresist composition according to <4> or <5> on a substrate, (2) a step of forming a photoresist film by conducting drying, (3) a step of exposing the photoresist film to radiation, (4) a step of baking the exposed photoresist film, and (5) a step of developing the baked photoresist film with an alkaline developer, thereby forming a photoresist pattern.

DESCRIPTION OF PREFERRED EMBODIMENTS

The salt of the present invention is represented by the formula (I):

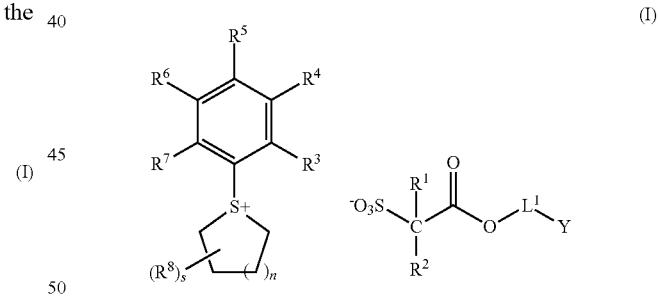

wherein $R^1$ and $R^2$ independently each represent a fluorine atom or a C1-C6 perfluoroalkyl group, $L^1$ represents a single bond, a C1-C6 alkanediyl group, a C4-C8 divalent alicyclic hydrocarbon group, —$(CH_2)_t$—CO—O—* or —$(CH_2)_t$—CO—O—$CH_2$—$(CH_2)_u$—*, one or more —$CH_2$— in the alkanediyl group and —$(CH_2)_u$— can be replaced by —O—, t represents an integer of 1 to 12, u represents an integer of 0 to 12, * represents a binding position to Y, Y represents a C3-C18 monovalent alicyclic hydrocarbon group which can have one or more substituents, and one or more —$CH_2$— in the monovalent alicyclic hydrocarbon group can be replaced by —O—, —CO— or —$SO_2$—, $R^3$, $R^4$, $R^5$, $R^6$ and $R^7$ each independently represent a hydrogen atom, a hydroxyl group, a C1-C6 alkyl group, a C1-C6 alkoxy group, a C2-C7 alkoxycarbonyl group or a C2-C12 acyloxy group, and one or more —$CH_2$— in the alicycle containing $S^+$ can be replaced by —O— or —CO—, n represents an integer of 1 to 3, s represents an integer of 0 to 3, and $R^8$ is independently in each occurrence a C1-C6 alkyl group (hereinafter, simply referred to as SALT (I)).

Examples of the C1-C6 perfluoroalkyl group include a trifluoromethyl group, a perfluoroethyl group, a perfluoropropyl group, a perfluoroisopropyl group, a perfluorobutyl group, a perfluoro-sec-butyl group, a perfluoro-tert-butyl group, a perfluoropentyl group and a perfluorohexyl group, and a trifluoromethyl group is preferable. It is preferred that $R^1$ and $R^2$ independently each represent a fluorine atom or a trifluoromethyl group, and it is more preferred that $R^1$ and $R^2$ are fluorine atoms.

Examples of the C1-C6 alkanediyl group include a linear alkanediyl group such as a methylene group, an ethylene group, a propane-1,3-diyl group, a propane-1,2-diyl group, a butane-1,4-diyl group, a pentane-1,5-diyl group and a hexane-1,6-diyl group, and a branched alkanediyl group such as a butane-1,3-diyl group, a 2-methylpropane-1,3-diyl group, a 2-methylpropane-1,2-diyl group, a pentane-1,4-diyl group and a 2-methylbutane-1,4-diyl group.

One or more —CH$_2$— in the alkanediyl group can be replaced by —O—, and examples of the alkanediyl group in which one or more —CH$_2$— are replaced by —O— include —CH$_2$—O—, —CH$_2$—CH$_2$—O—, —CH$_2$—CH$_2$—CH$_2$—O— and —CH$_2$—CH$_2$-O—CH$_2$—, and —CH$_2$—CH$_2$—O— is preferable.

Examples of the C4-C8 divalent alicyclic hydrocarbon group include a C4-C8 cycloalkanediyl group such as a cyclobutane-1,3-diyl group, a cyclopentane-1,3-diyl group, a cyclohexane-1,4-diyl group and a cyclooctane-1,5-diyl group.

Examples of —(CH$_2$)$_t$—CO—O—* include —CH$_2$—CO—O—*, —(CH$_2$)$_2$—CO—O—*, —(CH$_2$)$_3$—CO—O—*, —(CH$_2$)$_4$—CO—O—*, —(CH$_2$)$_6$—CO—O—*, and —(CH$_2$)$_8$—CO—O—*, and —CH$_2$—CO—O—* and —(CH$_2$)$_2$—CO—O—* are preferable.

Examples of —(CH$_2$)$_t$—CO—O—CH$_2$—(CH$_2$)$_u$—* include —CH$_2$—CO—O—CH$_2$—*, —CH$_2$—CO—O—CH$_2$—CH$_2$—*, —CH$_2$—CO—O—CH$_2$—(CH$_2$)$_2$—*, —CH$_2$—CO—O—CH$_2$—CH$_2$—O—* and —CH$_2$—CO—O—CH$_2$—CH$_2$—O—CH$_2$—*.

Preferable examples of the C3-C18 monovalent alicyclic hydrocarbon group include a C3-C18 cycloalkyl group, and a C3-C12 cycloalkyl group is more preferable. The cycloalkyl group may be a monocyclic or a polycyclic. Herein, "cylcoalkyl group" contains a cycloalkyl group wherein one or more C1-C12 alkyl groups are bonded to one or more ring carbons.

The C3-C18 monovalent alicyclic hydrocarbon group can have one or more substituents. Examples of the substituent include a halogen atom other than a fluorine atom, a hydroxyl group, a glycidyloxy group, a C2-C4 acyl group, a C1-C12 alkoxy group, a C6-C18 aromatic hydrocarbon group, a C7-C21 aralkyl group and —(CH$_2$)$_{j2}$—O—CO—$R^{i1}$— in which $R^{i1}$ represents a C1-C16 aliphatic hydrocarbon group, a C3-C16 alicyclic hydrocarbon group or a C6-C18 aromatic hydrocarbon group and j2 represents an integer of 0 to 4. The C6-C18 aromatic hydrocarbon group and the C7-C21 aralkyl group can have a C1-C8 alkyl group, a halogen atom or a hydroxyl group.

Examples of the C1-C16 aliphatic hydrocarbon group represented by $R^{i1}$ include a methyl group, an ethyl group, a propyl group, a butyl group, a pentyl group, a hexyl group, a heptyl group and an octyl group. The C3-C16 alicyclic hydrocarbon group may be monocyclic or polycyclic. Examples of the monocyclic alicyclic hydrocarbon group include a cycloalkyl group such as a cyclopentyl group, a cyclohexyl group, a methylcyclohexyl group, a dimethylcyclohexyl group, a cycloheptyl group and a cyclooctyl group. Examples of the polycyclic alicyclic hydrocarbon group include a decahydronaphthyl group, an adamantyl group, a norbornyl group, a methylnorbornyl group and the following.

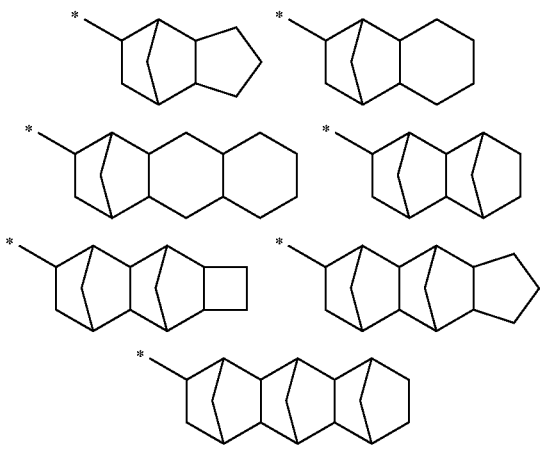

Examples of the C6-C18 aromatic hydrocarbon group represented by $R^{i1}$ include a C6-C18 aryl group such as a phenyl group, a naphthyl group, an anthryl group, a p-methylphenyl group, a p-tert-butylphenyl group, a p-adamantylphenyl group, a tolyl group, a xylyl group, a cumyl group, a mesityl group, a biphenyl group, a phenanthryl group, a 2,6-diethylphenyl group and a 2-methyl-6-ethylphenyl group.

One or more —CH$_2$— in the monovalent alicyclic hydrocarbon group can be replaced by —O—, —CO— or —SO$_2$—, and examples of the monovalent alicyclic in which one or more —CH$_2$— are replaced by —O—, —CO— or —SO$_2$— include a group having a cyclic ether structure, a saturated cyclic hydrocarbon group having an oxo group, a sultone ring group and a lactone ring group.

Preferable examples thereof include the groups represented by the formulae (Y1) to (Y29) in which * represents a binding position to $L^1$.

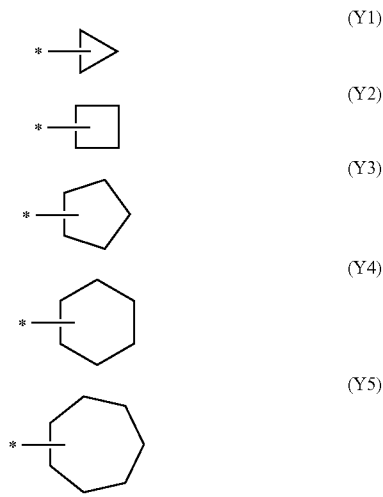

-continued
(Y6) 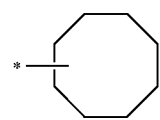
(Y7) 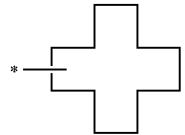
(Y8) 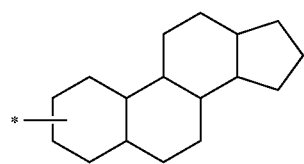
(Y9) 
(Y10) 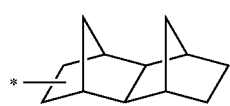
(Y11) 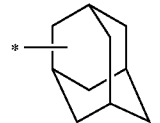
(Y12) 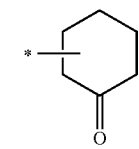
(Y13) 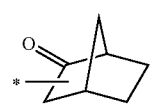
(Y14) 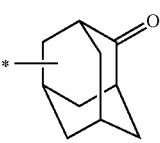
(Y15) 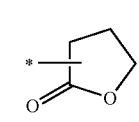
(Y16) 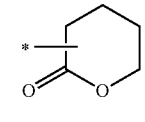
(Y17) 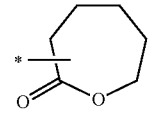
-continued
(Y18) 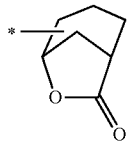
(Y19) 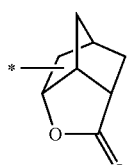
(Y20) 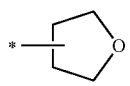
(Y21) 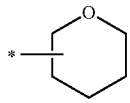
(Y22) 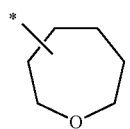
(Y23) 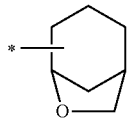
(Y24) 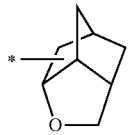
(Y25) 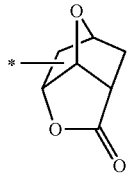
(Y26) 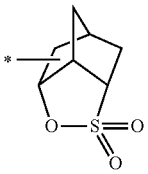
(Y27) 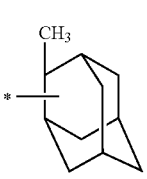

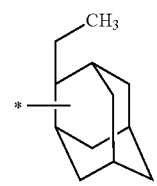
(Y28)

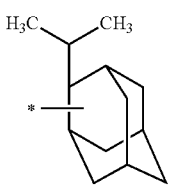
(Y29)

Among them, preferred are groups represented by the formulae (Y1) to (Y19) and (Y27) to (Y29), and more preferred are groups represented by the formulae (Y11), (Y14), (Y15), (Y19), (Y27), (Y28) and (Y29), and especially preferred are groups represented by the formulae (Y11) and (Y14).

Examples of Y having one or more substituents include the followings:

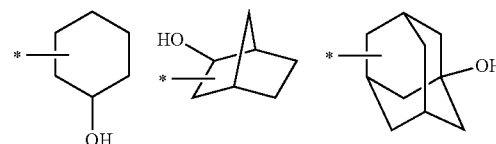

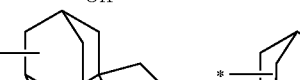

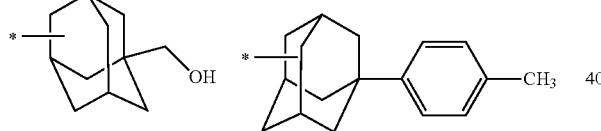

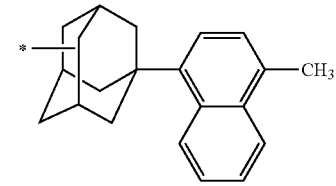

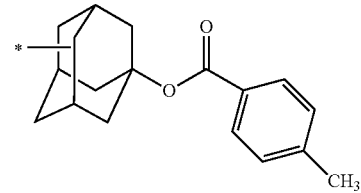

Y is preferably an adamantyl group which can have one or more substituents, and is more preferably an adamantyl group or an hydroxyadamantyl group.

Preferable examples of the anion part of SALT (I) include the following anions represented by the formulae (b1-1-1) to (b1-1-9).

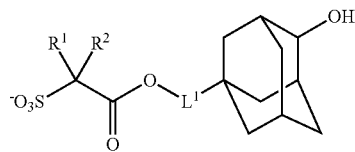
(b1-1-1)

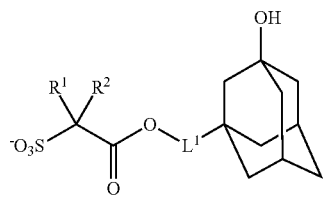
(b1-1-2)

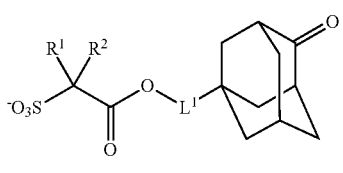
(b1-1-3)

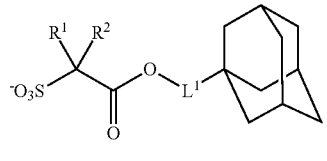
(b1-1-4)

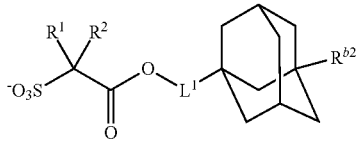
(b1-1-5)

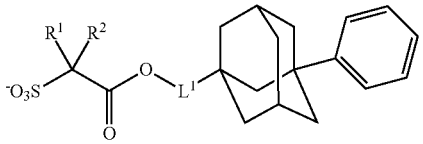
(b1-1-6)

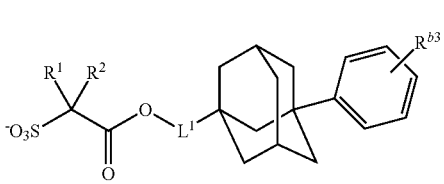
(b1-1-7)

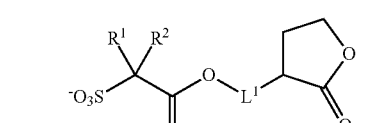
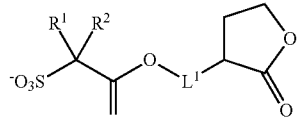
(b1-1-8)

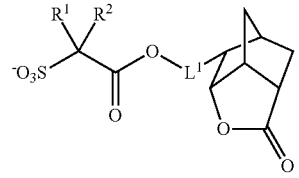
(b1-1-9)

wherein $R^1$, $R^2$ and $L^1$ are the same as defined above, and $R^{b2}$ and $R^{b3}$ each independently represent the same group as described as the substituent of the alicyclic hydrocarbon group represented by Y, and it is more preferred that $R^{b2}$ and $R^{b3}$ each independently represent a C1-C4 aliphatic hydrocarbon group or a hydroxyl group, and it is still more preferred that $R^{b2}$ and $R^{b3}$ each independently represent a methyl group or a hydroxyl group.
Specific examples of the anion part of SALT (I) include the followings.
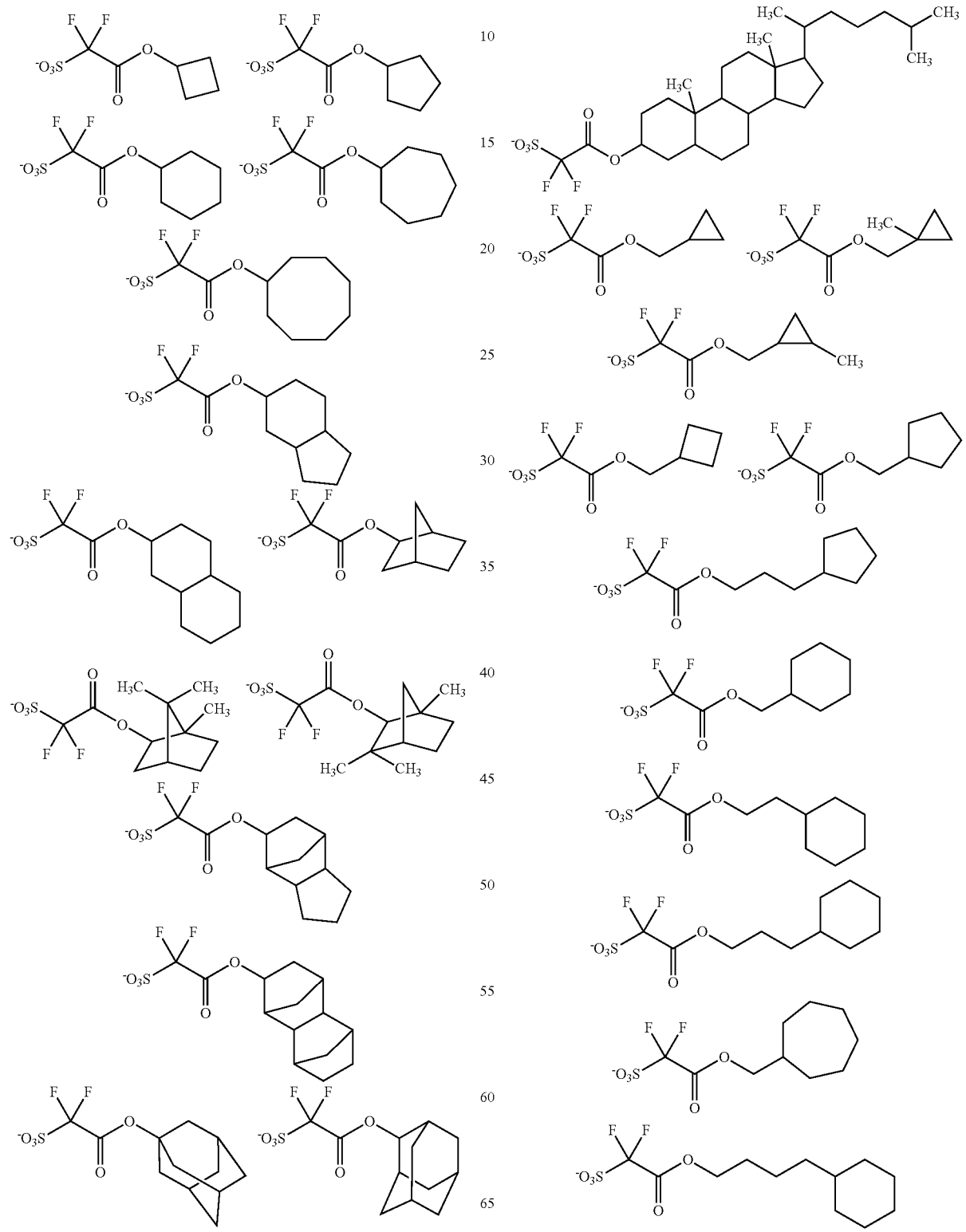

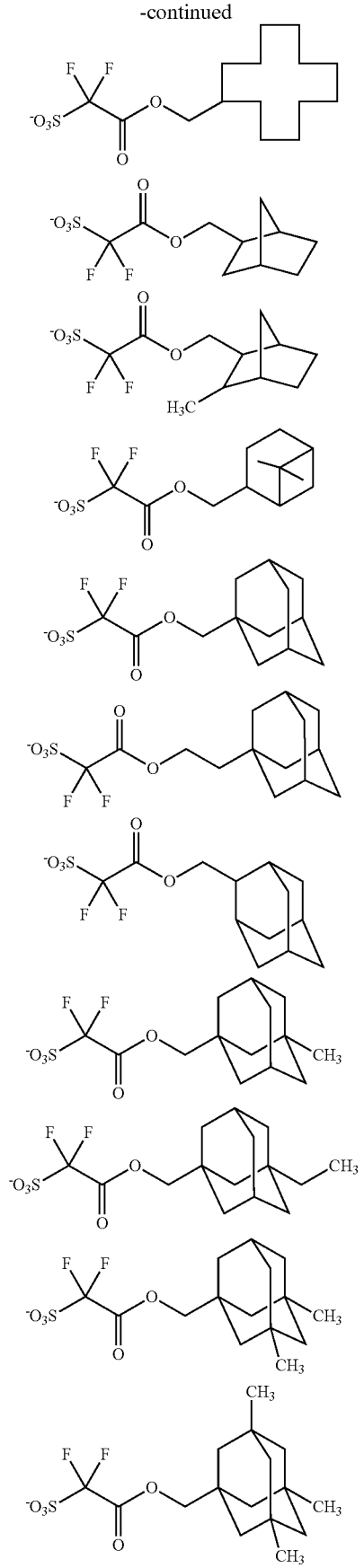
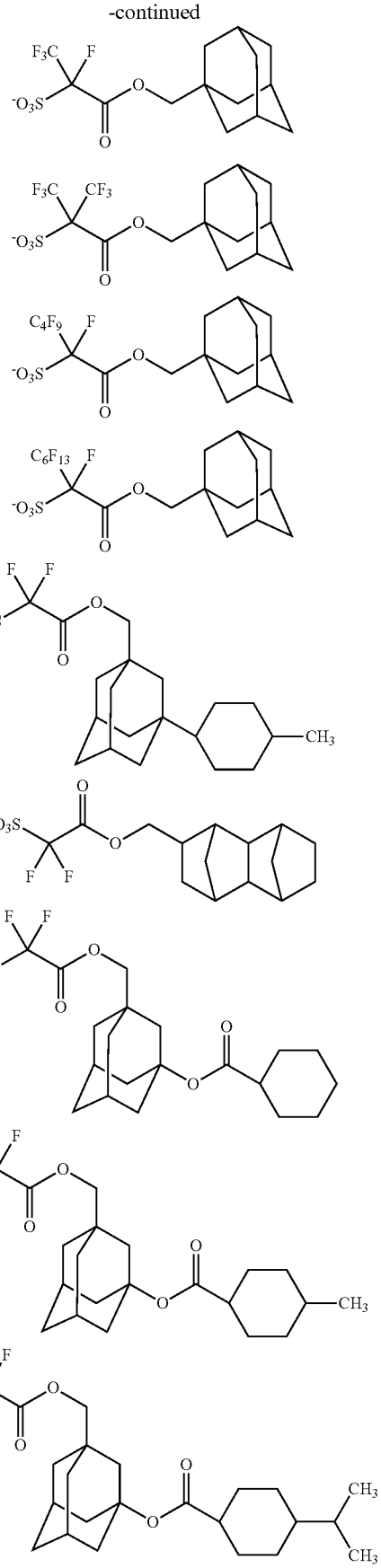

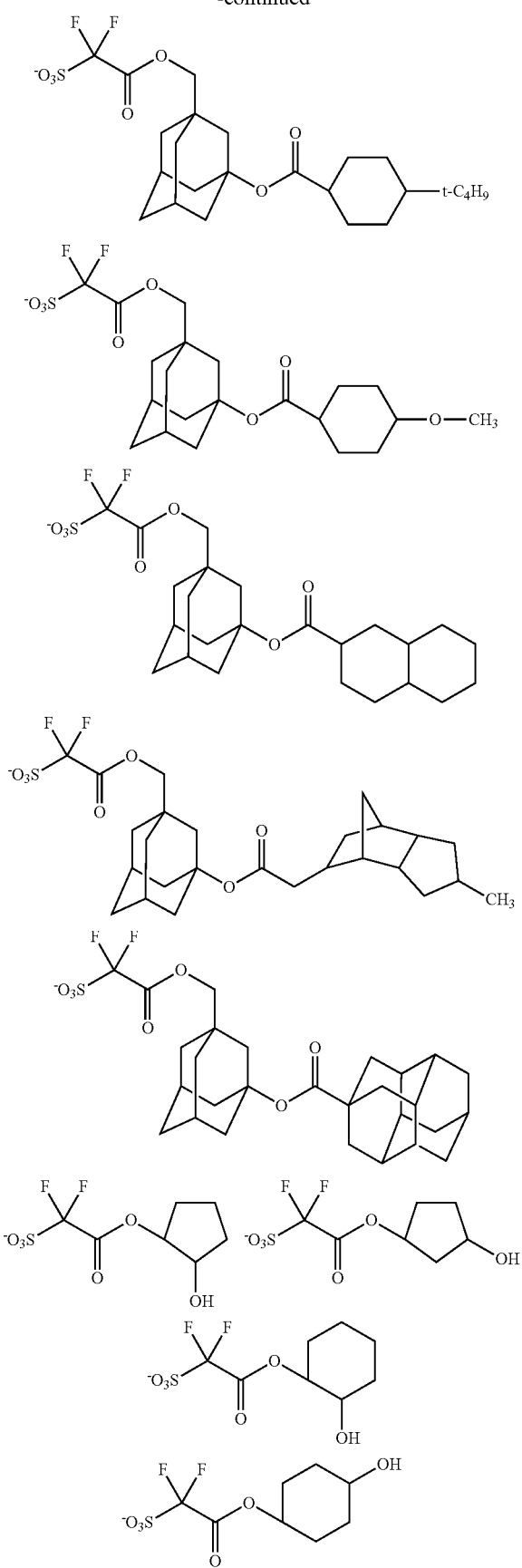
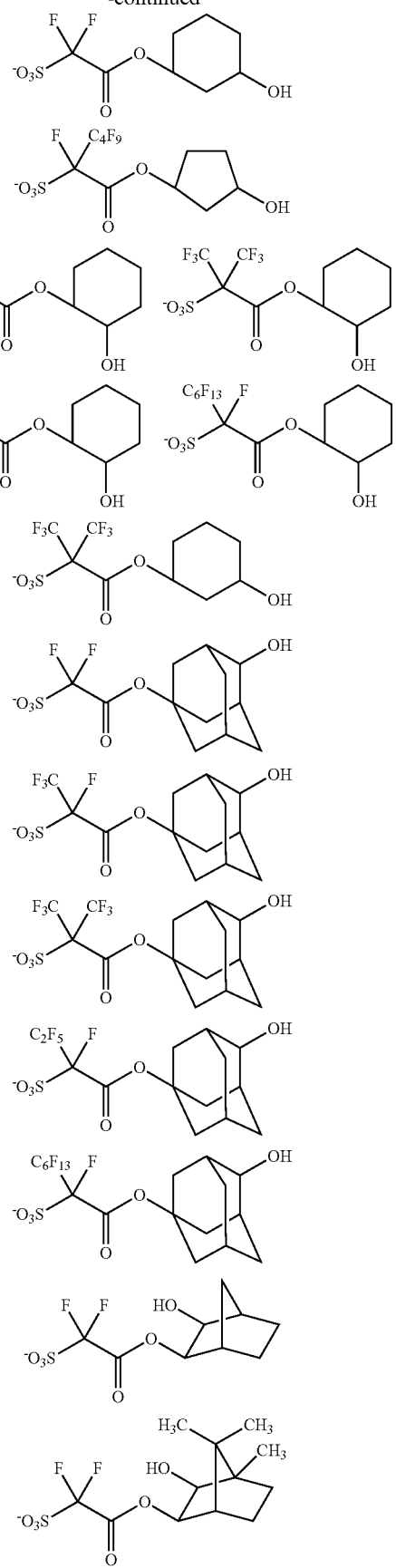

-continued
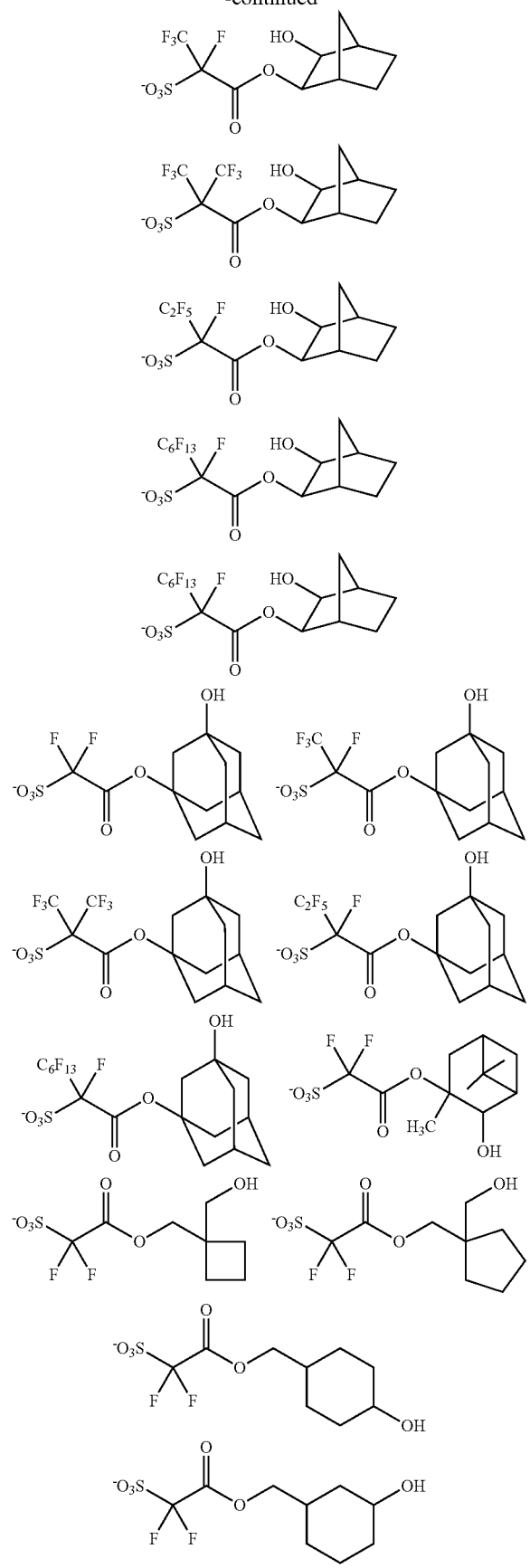
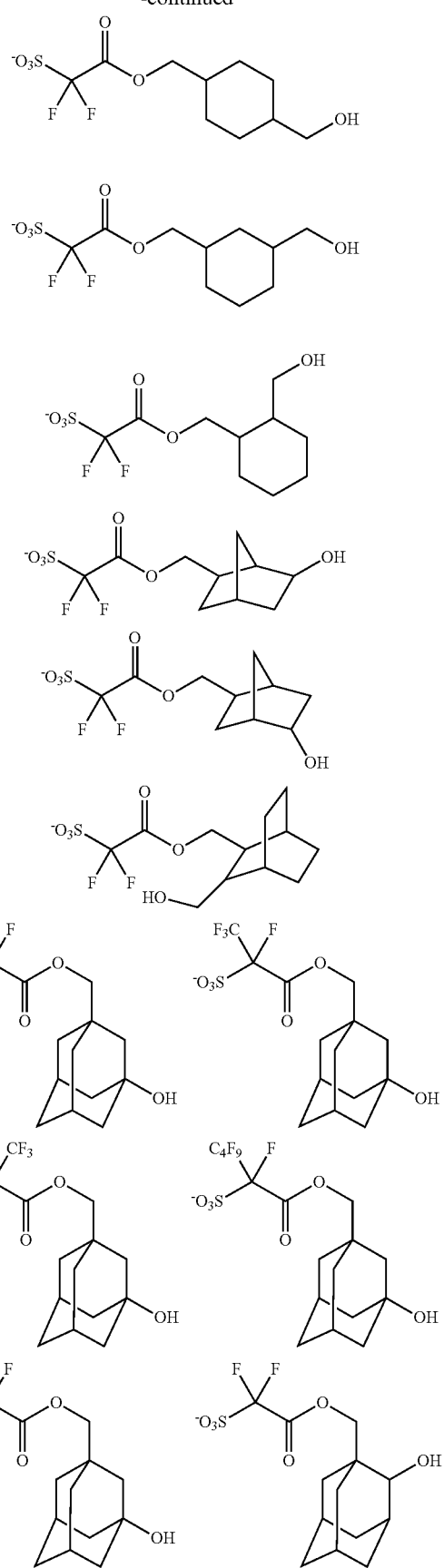

17
-continued
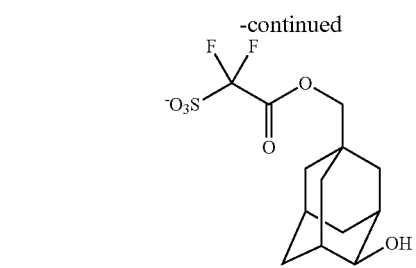
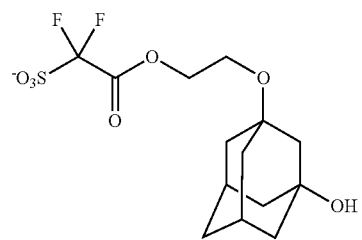
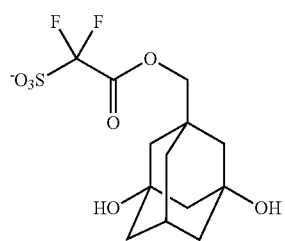 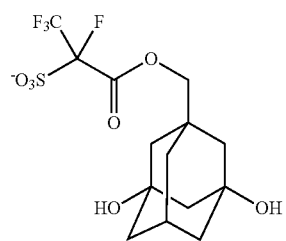
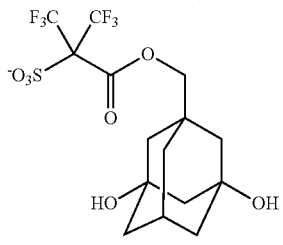 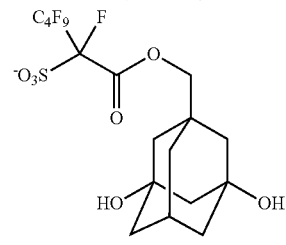
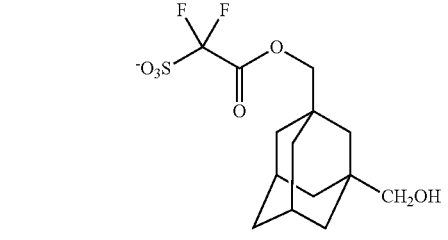
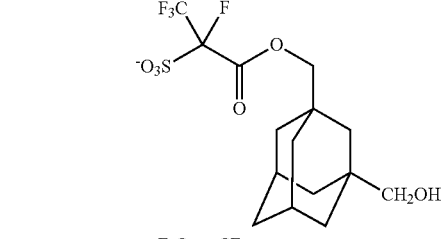
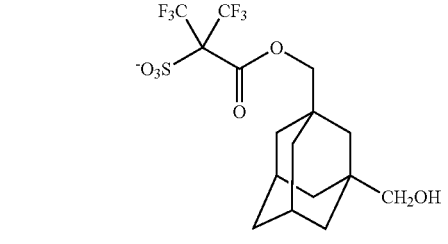
18
-continued
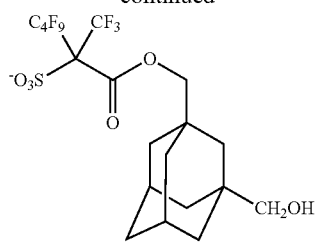
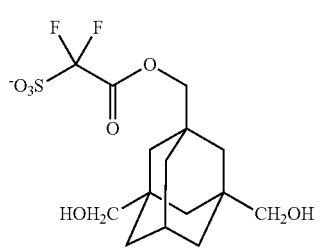
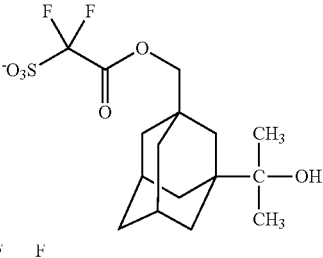
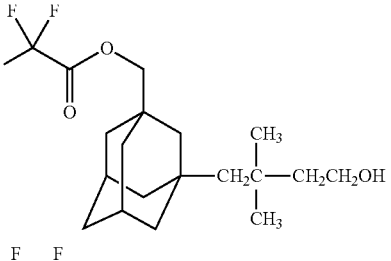
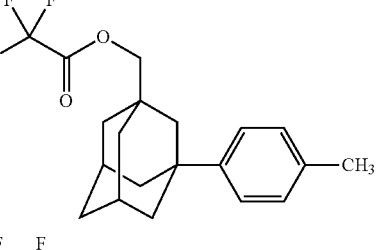
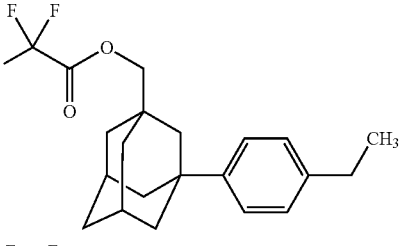
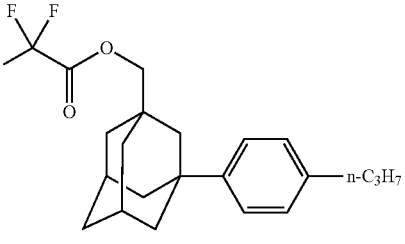

-continued
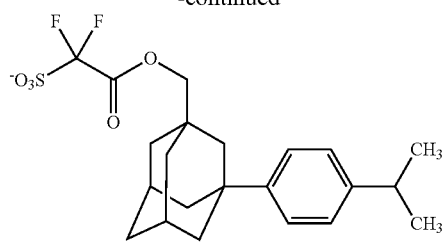
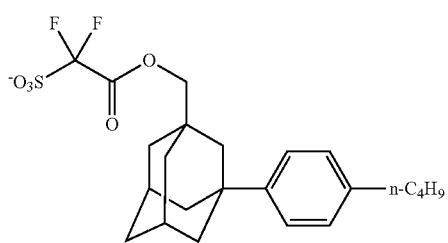
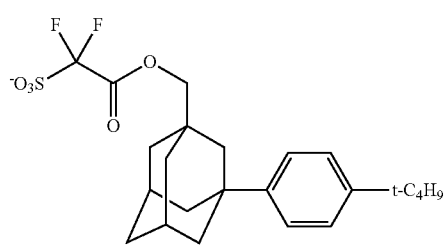
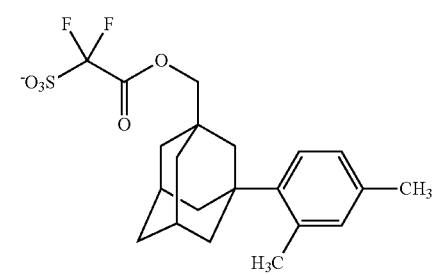
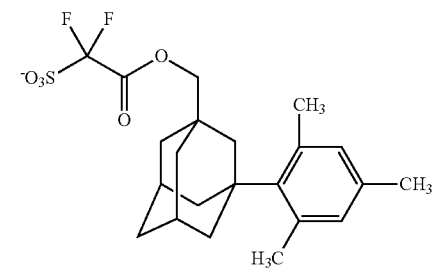
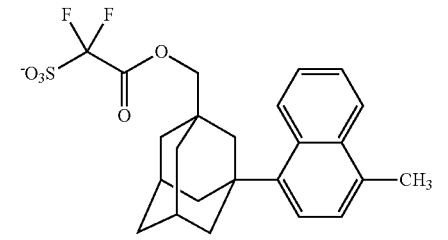
-continued
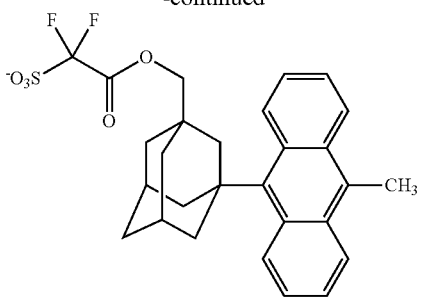
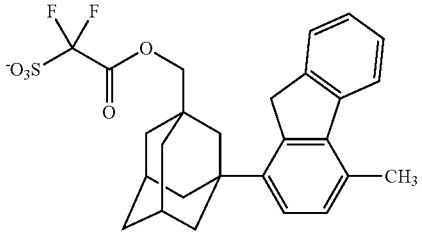
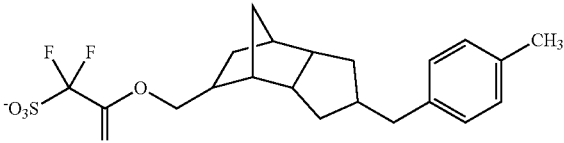
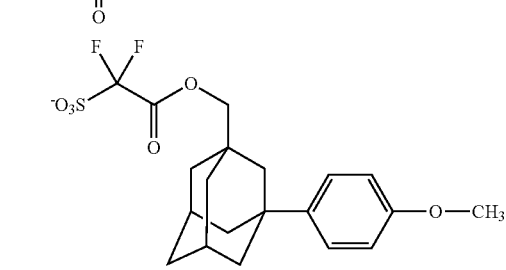
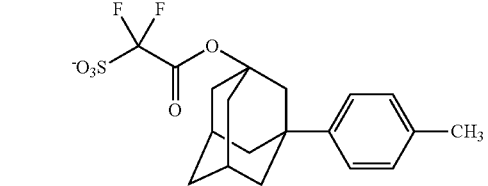
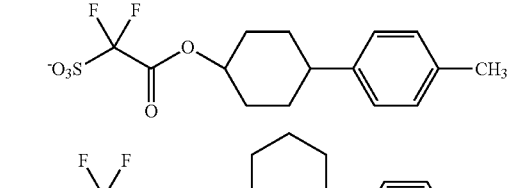
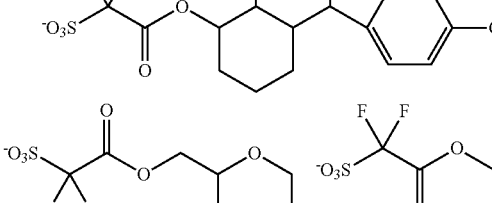
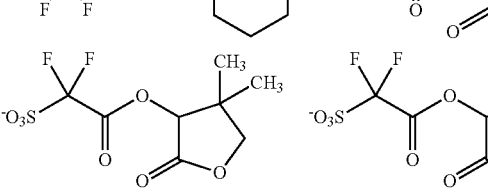

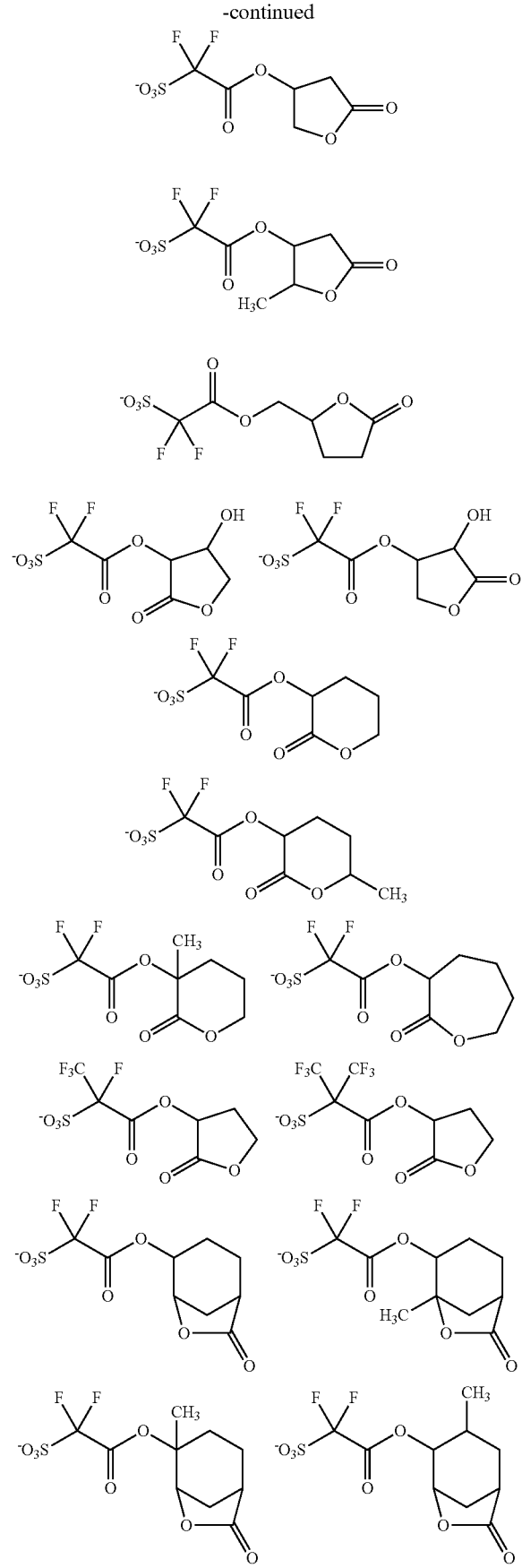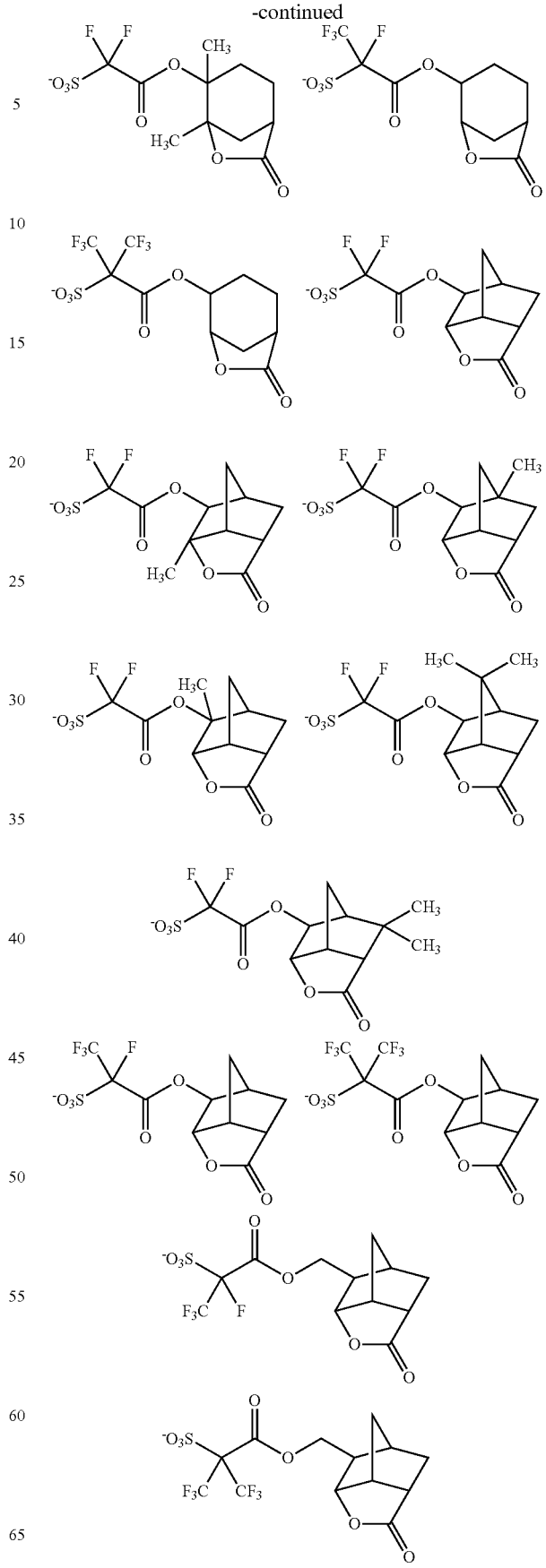

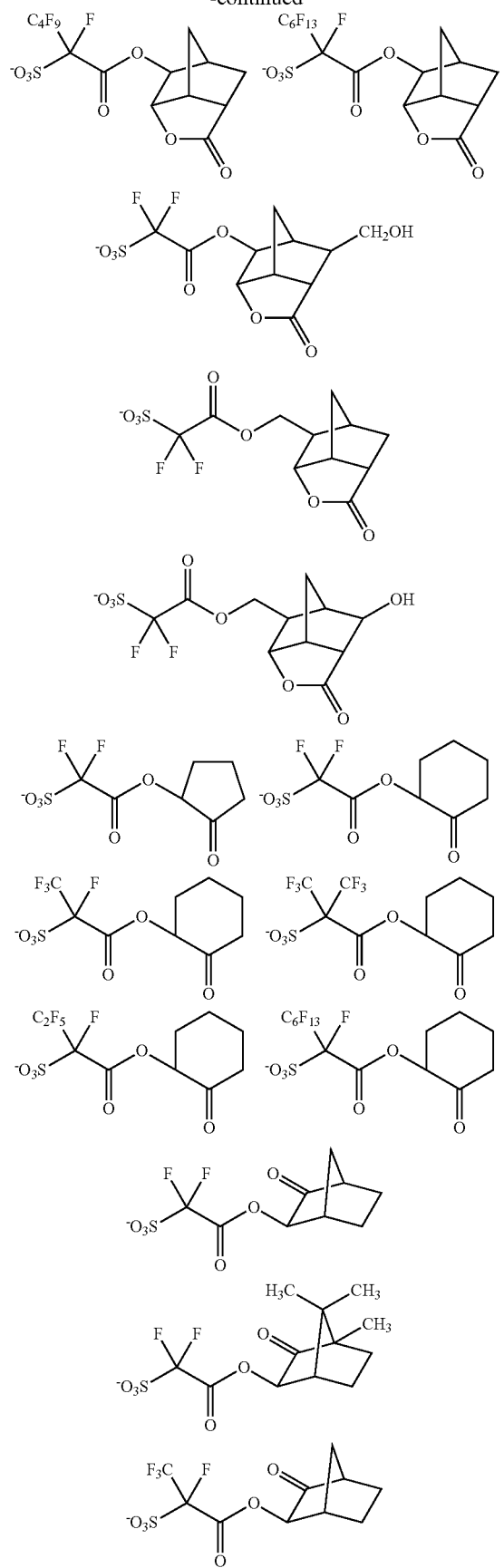
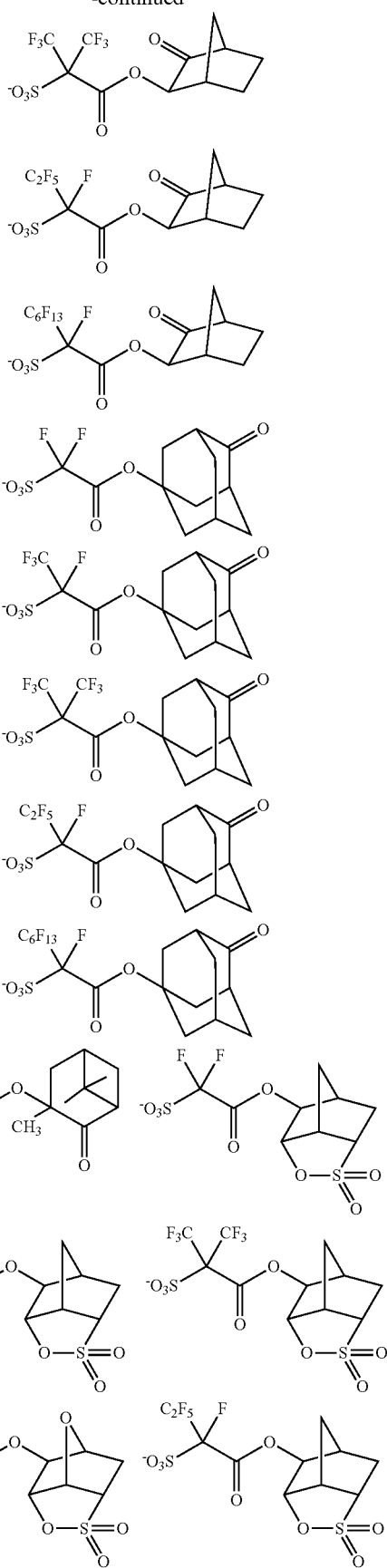

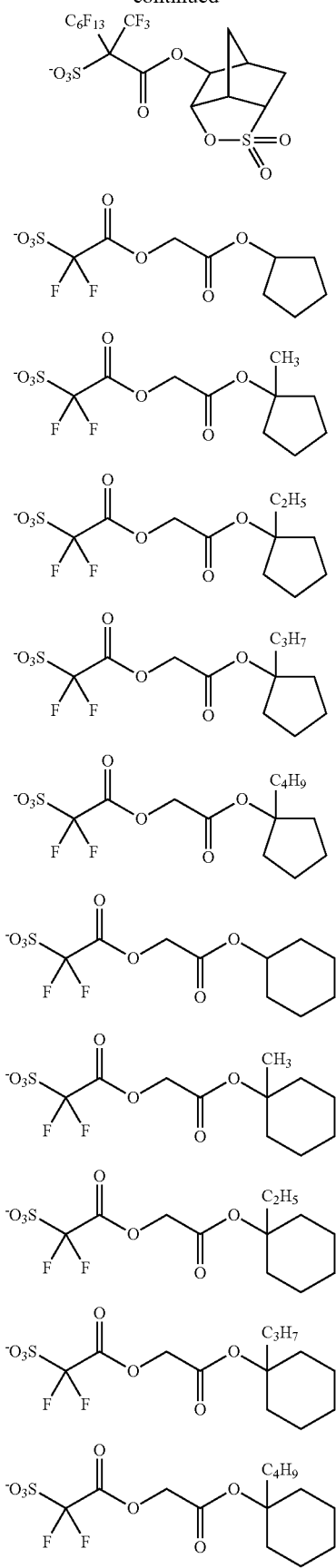
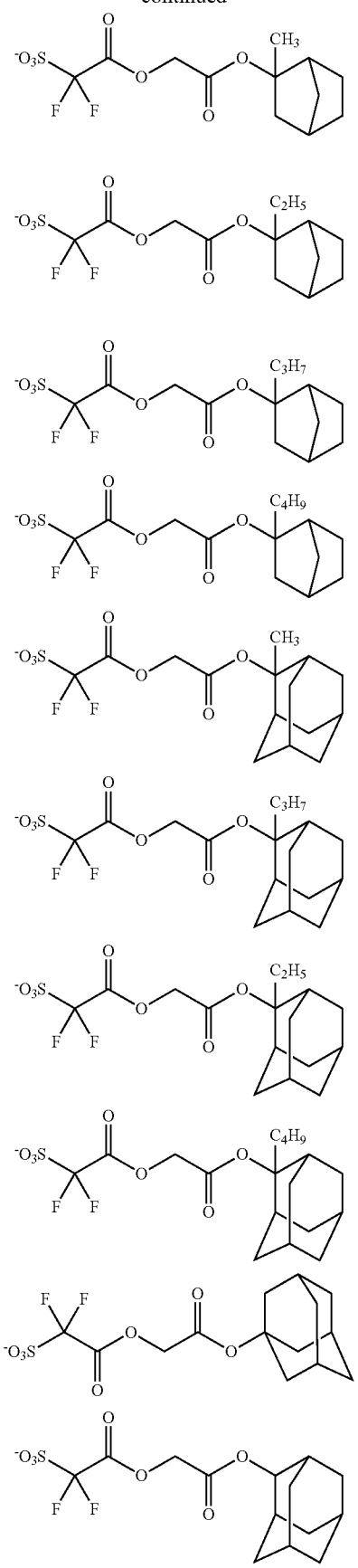

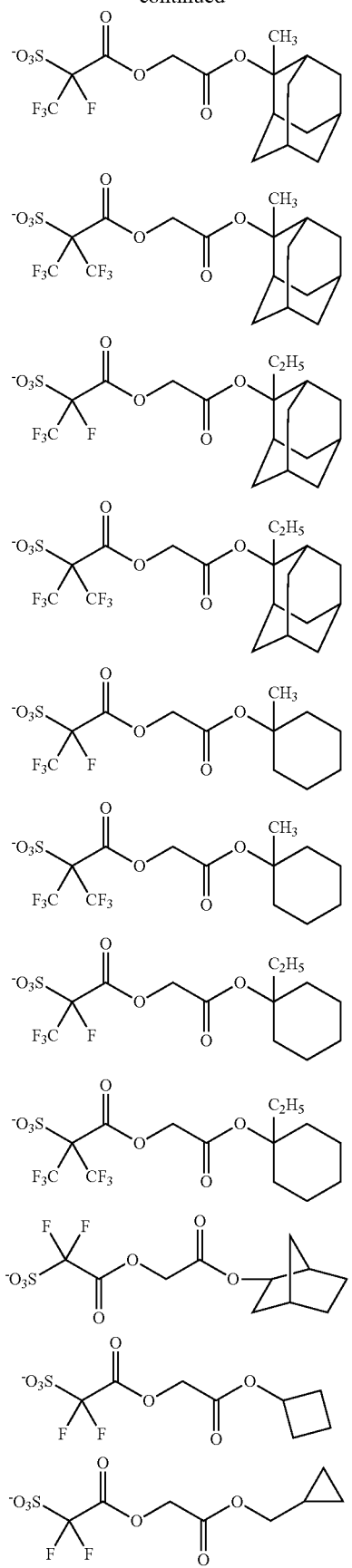
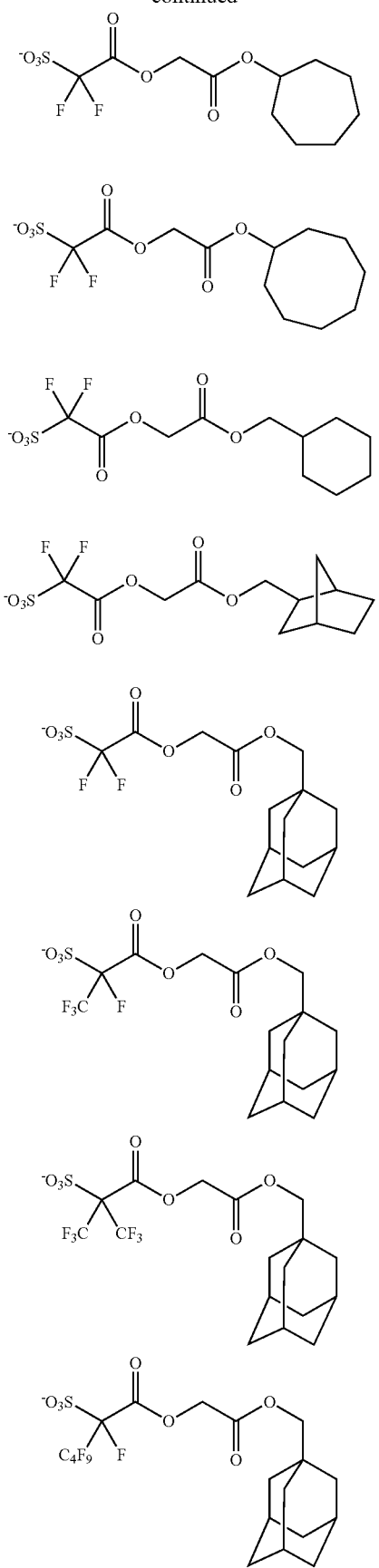

29
-continued
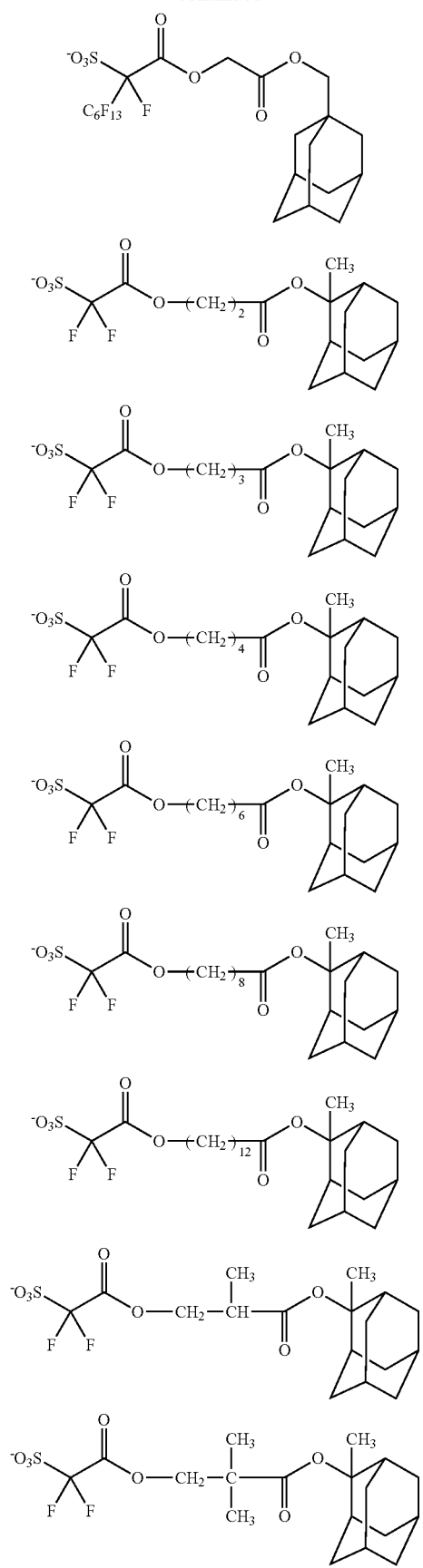
30
-continued
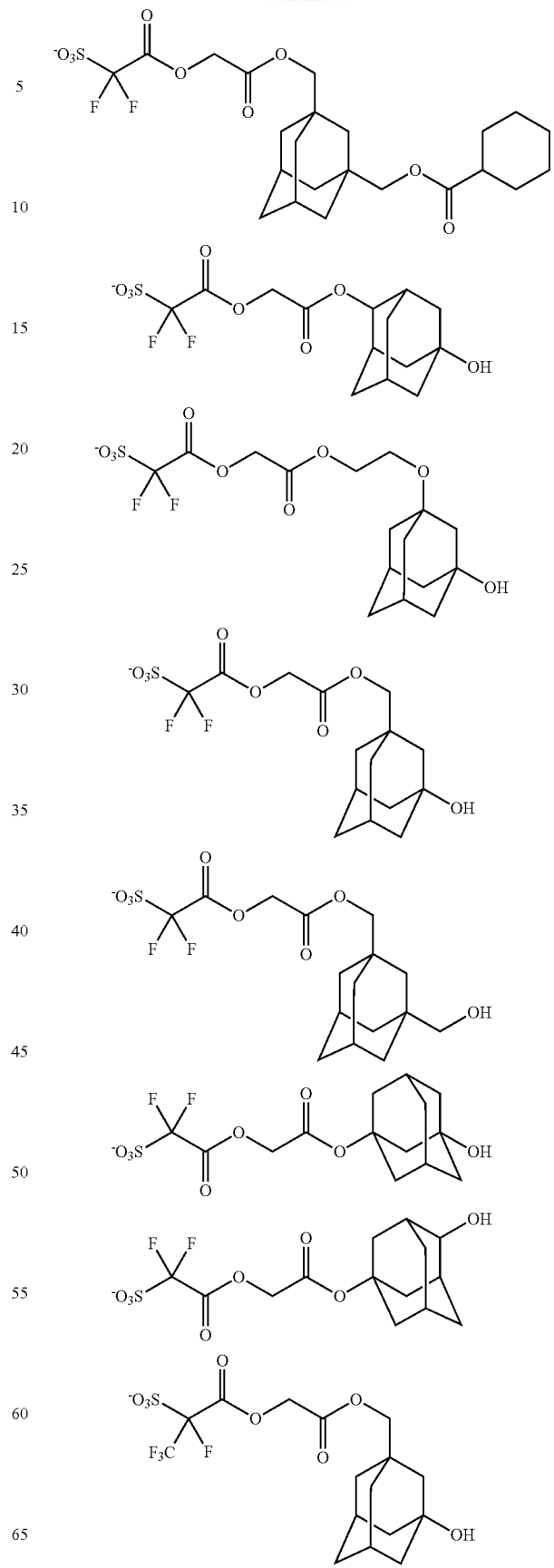

31
-continued
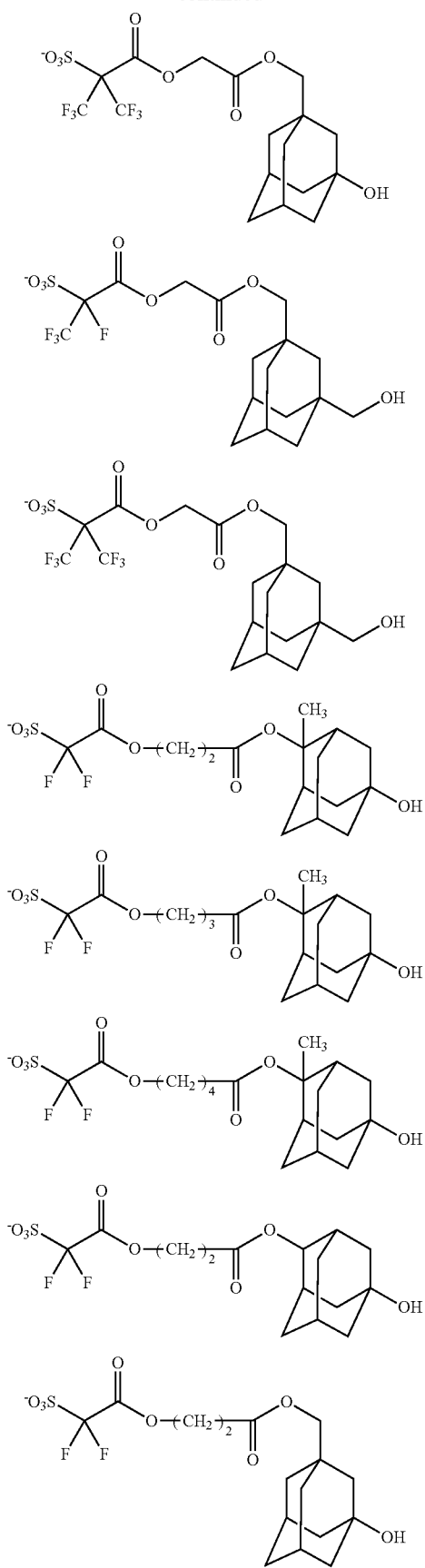
32
-continued
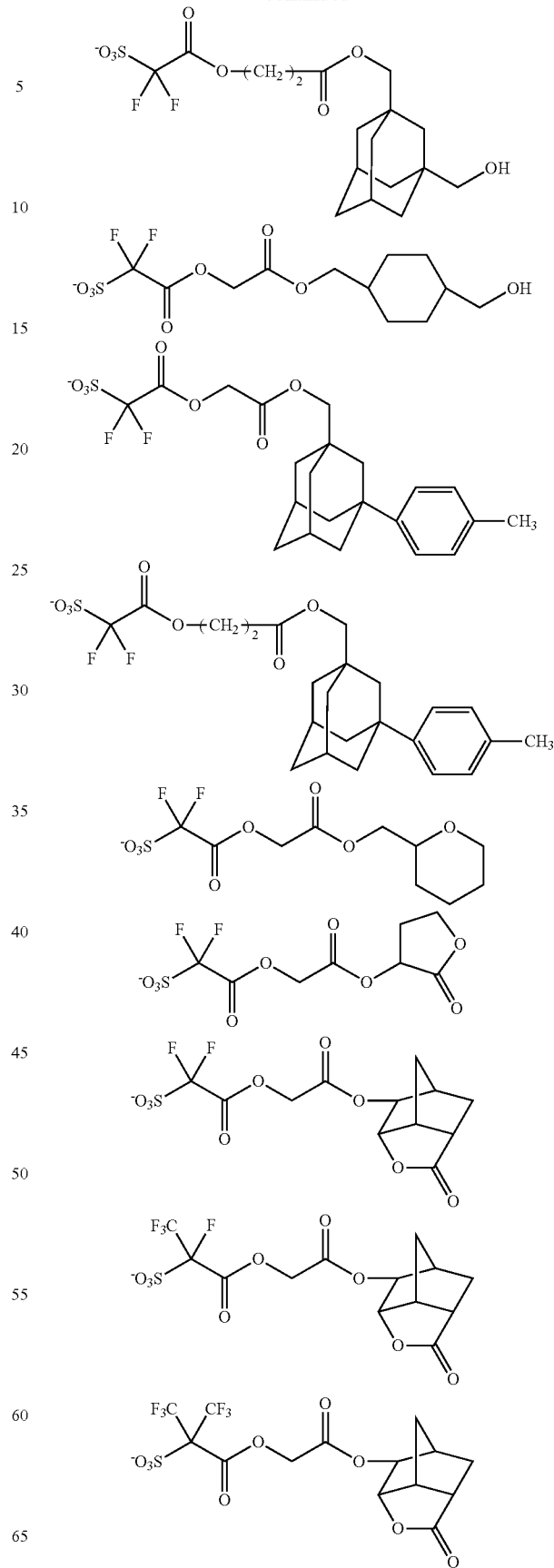

33
-continued
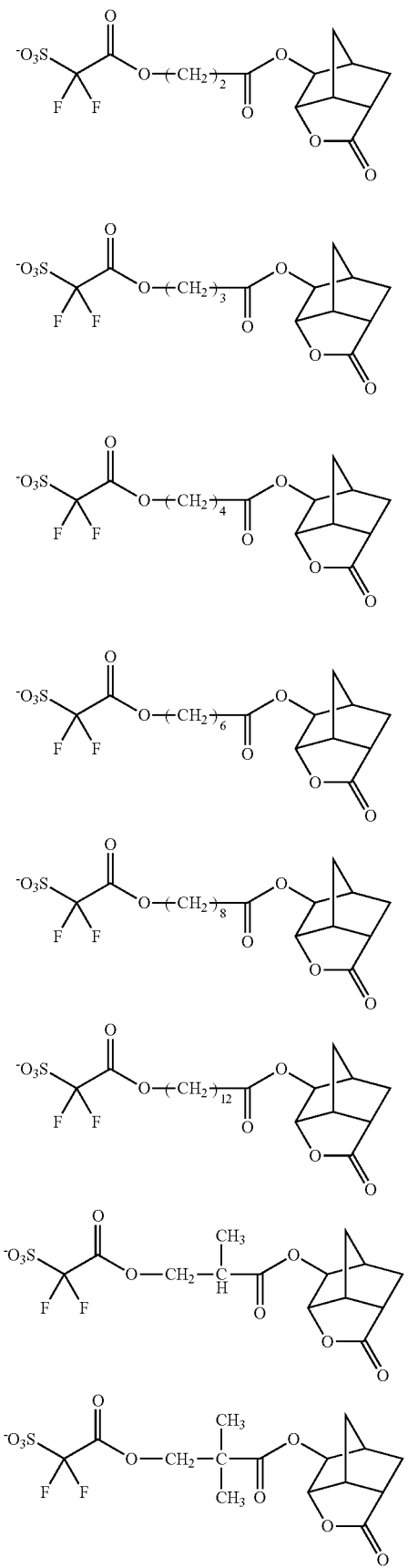
34
-continued
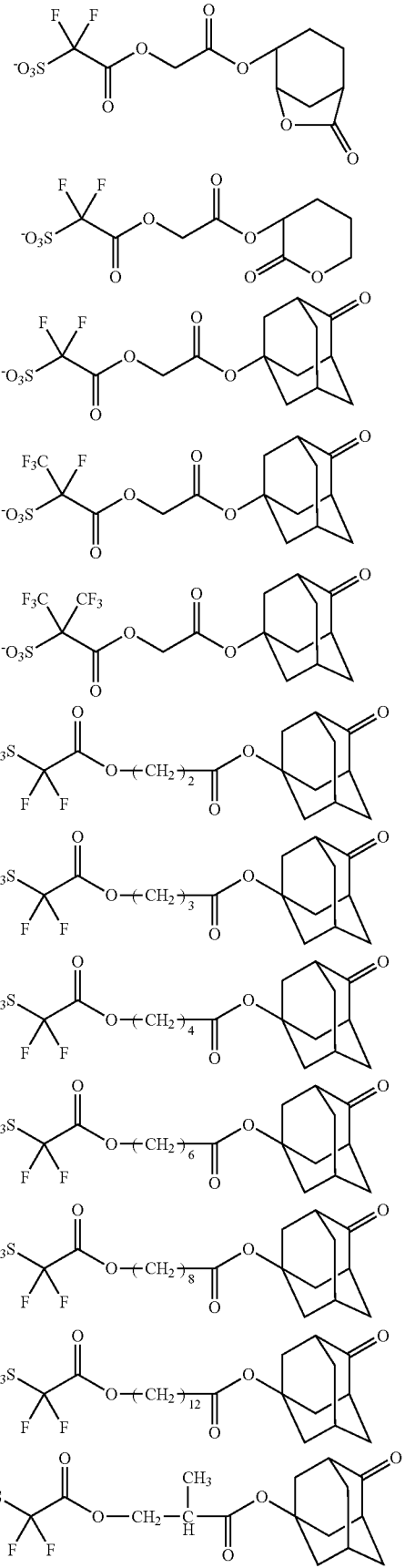

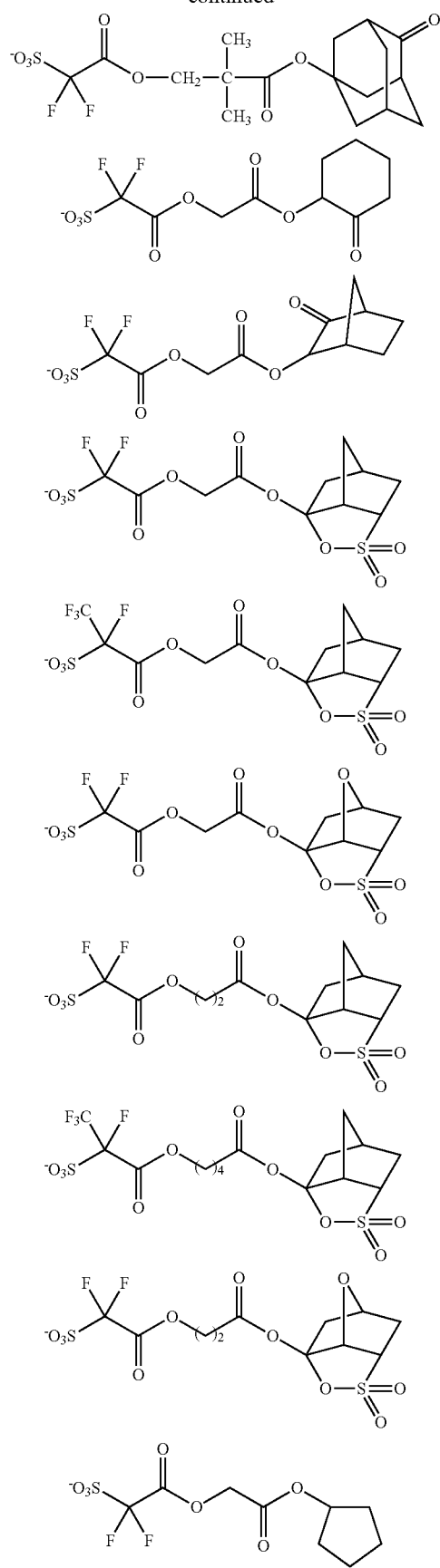
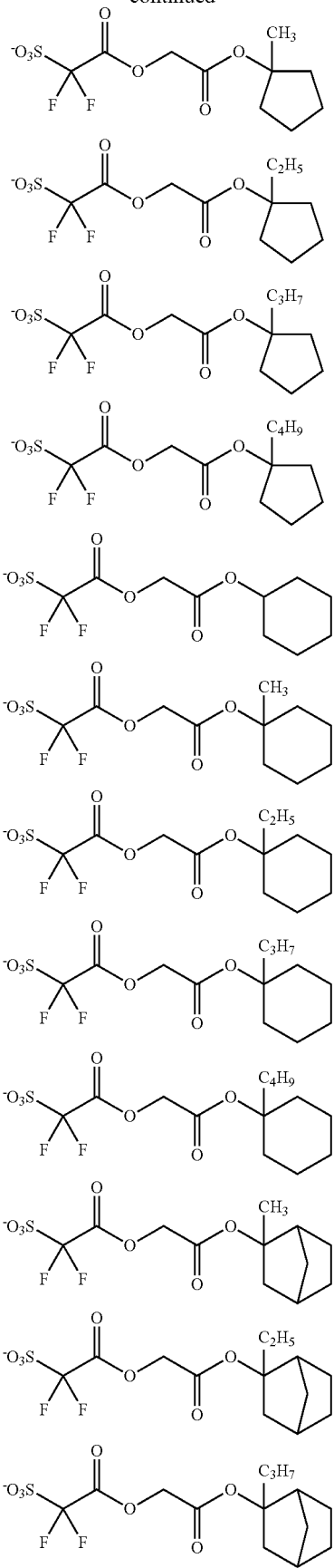

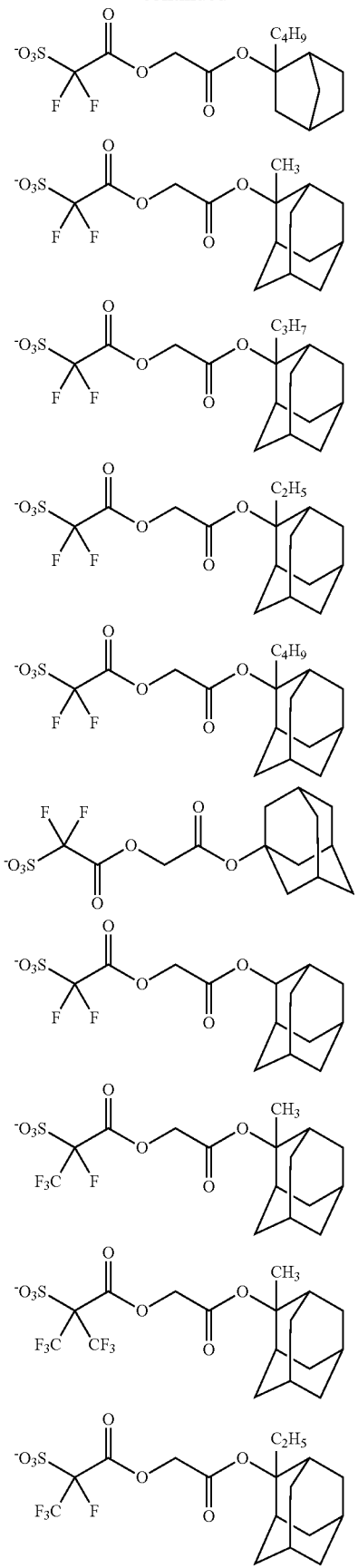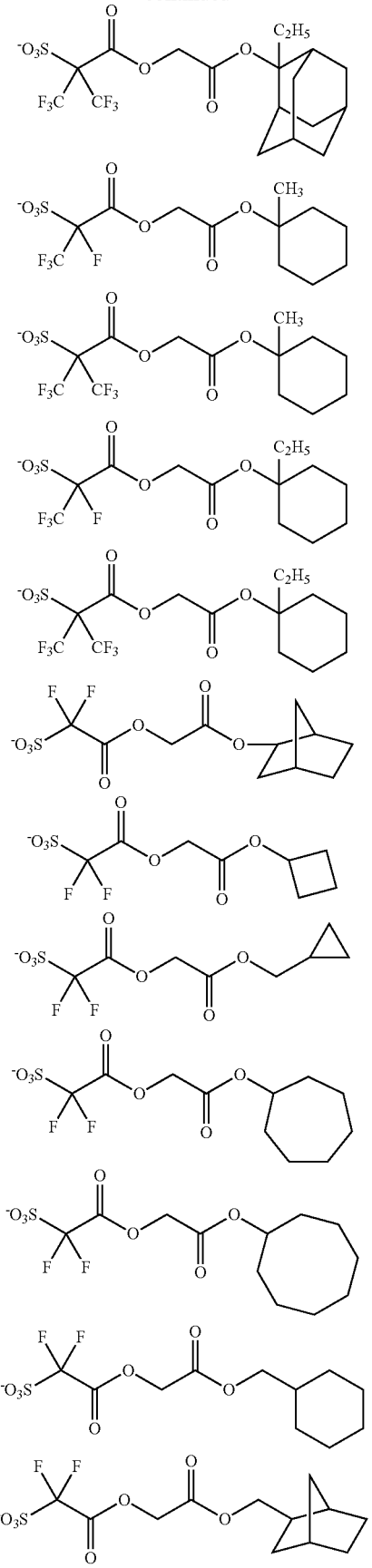

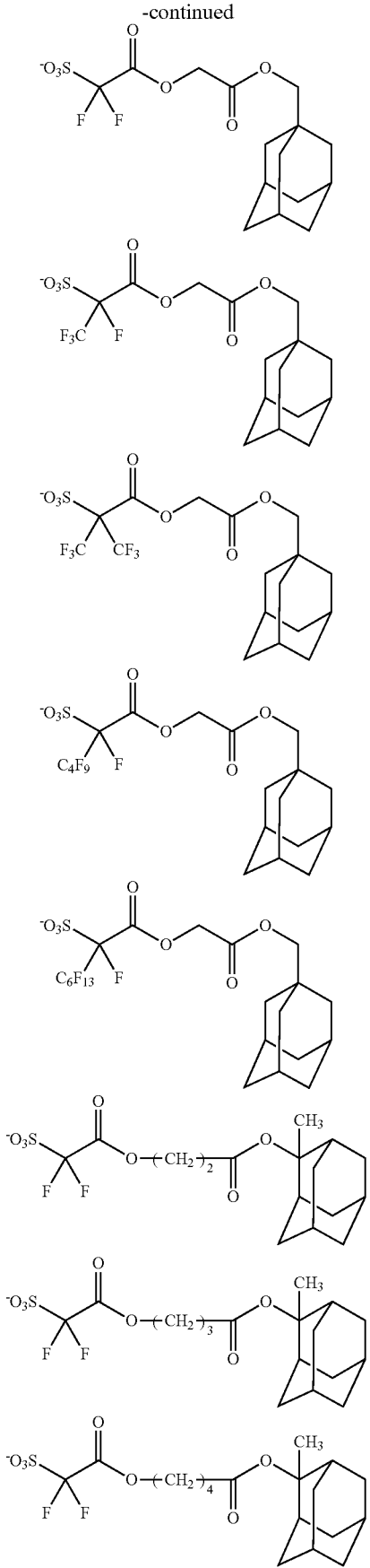
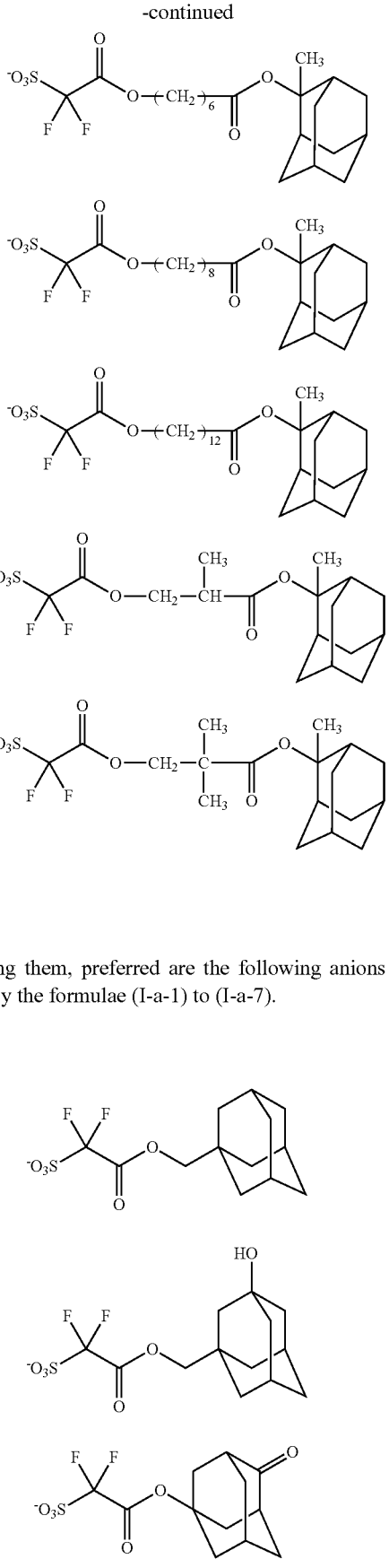
Among them, preferred are the following anions represented by the formulae (I-a-1) to (I-a-7).

-continued

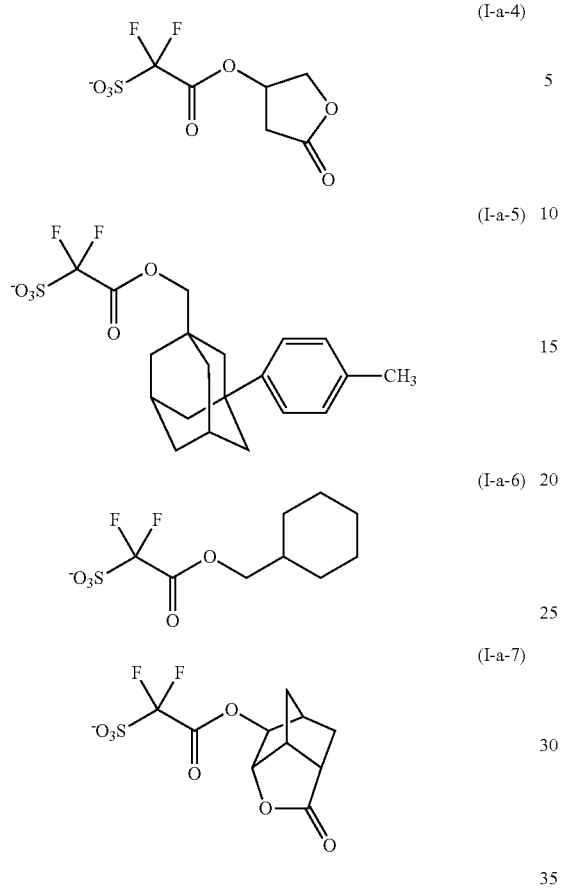

(I-a-4)
(I-a-5)
(I-a-6)
(I-a-7)

Examples of the C1-C6 alkyl group represented by $R^3$, $R^4$, $R^5$, $R^6$ and $R^7$ include a methyl group, an ethyl group, a propyl group and a butyl group. Examples of the C1-C6 alkoxy group include a methoxy group, an ethoxy group, a propoxy group and a butoxy group.

Examples of the C2-C7 alkoxycarbonyl group include a methoxycarbonyl group and a tert-butoxycarbonyl group. Examples of the C2-C12 acyloxy group include an acetyl group and a benzoyloxy group. One or more —$CH_2$— in the alicycle containing $S^+$ can be replaced by —O— or —CO—, n represents an integer of 1 to 3, s represents an integer of 0 to 3.

Examples of the C1-C6 alkyl group represented by $R^8$ include a methyl group, an ethyl group, a propyl group, a butyl group, a pentyl group and a hexyl group.

Examples of the organic counter ion of SALT (I) include the following cations represented by the formulae (I-c-1) to (I-c-24).

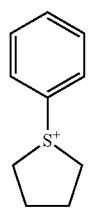

(I-c-1)

-continued

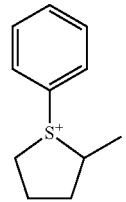

(I-c-2)

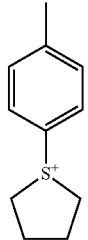

(I-c-3)

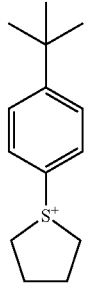

(I-c-4)

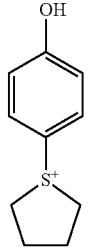

(I-c-5)

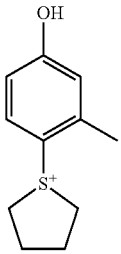

(I-c-6)

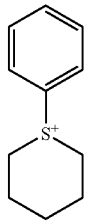

(I-c-7)

(I-c-8)
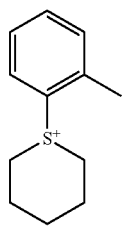
(I-c-9)
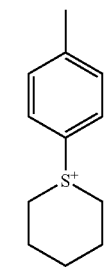
(I-c-10)
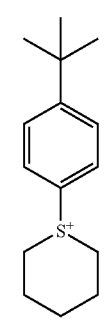
(I-c-11)
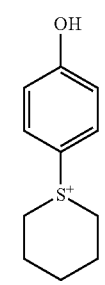
(I-c-12)
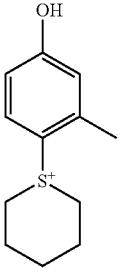
(I-c-13)
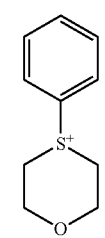
(I-c-14)
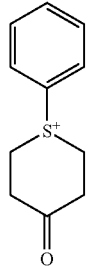
(I-c-15)
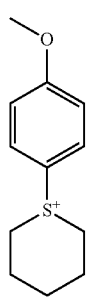
(I-c-16)
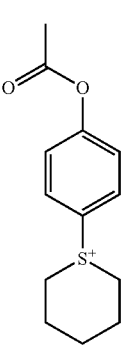
(I-c-17)
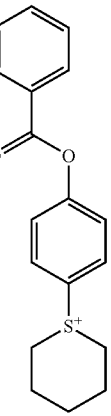

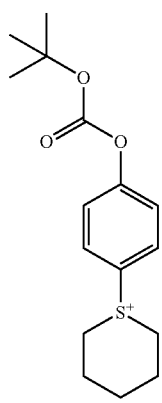
(I-c-18)
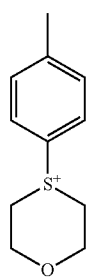
(I-c-19)
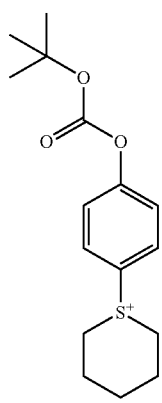
(I-c-20)
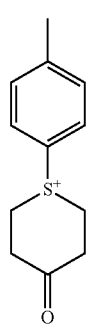
(I-c-21)
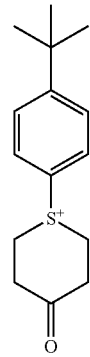
(I-c-22)
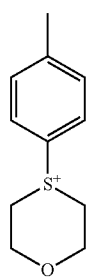
(I-c-23)
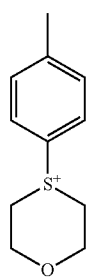
(I-c-24)
Examples of SALT (I) include those shown in Tables 1 to 5.
TABLE 1
| SALT (I) | Anion | Organic Cation |
|---|---|---|
| (I-1) | (I-a-2) | (I-c-7) |
| (I-2) | (I-a-2) | (I-c-13) |
| (I-3) | (I-a-2) | (I-c-20) |
| (I-4) | (I-a-3) | (I-c-13) |
| (I-5) | (I-a-2) | (I-c-10) |
| (I-6) | (I-a-2) | (I-c-4) |
| (I-7) | (I-a-3) | (I-c-20) |
| (I-8) | (I-a-3) | (I-c-19) |
| (I-9) | (I-a-3) | (I-c-23) |
| (I-10) | (I-a-2) | (I-c-19) |
| (I-11) | (I-a-2) | (I-c-23) |
| (I-12) | (I-a-1) | (I-c-1) |
| (I-13) | (I-a-2) | (I-c-1) |
| (I-14) | (I-a-3) | (I-c-1) |
| (I-15) | (I-a-4) | (I-c-1) |
| (I-16) | (I-a-5) | (I-c-1) |
| (I-17) | (I-a-6) | (I-c-1) |
| (I-18) | (I-a-7) | (I-c-1) |
| (I-19) | (I-a-1) | (I-c-2) |
| (I-20) | (I-a-2) | (I-c-2) |
| (I-21) | (I-a-3) | (I-c-2) |
| (I-22) | (I-a-5) | (I-c-2) |
| (I-23) | (I-a-7) | (I-c-2) |
| (I-24) | (I-a-1) | (I-c-3) |
| (I-25) | (I-a-2) | (I-c-3) |

TABLE 1-continued

| SALT (I) | Anion | Organic Cation |
|---|---|---|
| (I-26) | (I-a-3) | (I-c-3) |
| (I-27) | (I-a-5) | (I-c-3) |
| (I-28) | (I-a-7) | (I-c-3) |

TABLE 2

| SALT (I) | Anion | Organic Cation |
|---|---|---|
| (I-29) | (I-a-1) | (I-c-4) |
| (I-30) | (I-a-3) | (I-c-4) |
| (I-31) | (I-a-4) | (I-c-4) |
| (I-32) | (I-a-5) | (I-c-4) |
| (I-33) | (I-a-6) | (I-c-4) |
| (I-34) | (I-a-7) | (I-c-4) |
| (I-35) | (I-a-1) | (I-c-5) |
| (I-36) | (I-a-2) | (I-c-5) |
| (I-37) | (I-a-3) | (I-c-5) |
| (I-38) | (I-a-5) | (I-c-5) |
| (I-39) | (I-a-7) | (I-c-5)) |
| (I-40) | (I-a-1) | (I-c-6) |
| (I-41) | (I-a-2) | (I-c-6) |
| (I-42) | (I-a-3) | (I-c-6) |
| (I-43) | (I-a-5) | (I-c-6) |
| (I-44) | (I-a-7) | (I-c-6) |
| (I-45) | (I-a-1) | (I-c-7) |
| (I-46) | (I-a-3) | (I-c-7) |
| (I-47) | (I-a-4) | (I-c-7) |
| (I-48) | (I-a-5) | (I-c-7) |
| (I-49) | (I-a-6) | (I-c-7) |
| (I-50) | (I-a-7) | (I-c-7) |
| (I-51) | (I-a-1) | (I-c-8) |
| (I-52) | (I-a-2) | (I-c-8) |
| (I-53) | (I-a-3) | (I-c-8) |
| (I-54) | (I-a-5) | (I-c-8) |
| (I-55) | (I-a-7) | (I-c-8) |
| (I-56) | (I-a-1) | (I-c-9) |
| (I-57) | (I-a-2) | (I-c-9) |
| (I-58) | (I-a-3) | (I-c-9) |

TABLE 3

| SALT (I) | Anion | Organic Cation |
|---|---|---|
| (I-59) | (I-a-5) | (I-c-9) |
| (I-60) | (I-a-7) | (I-c-9) |
| (I-61) | (I-a-1) | (I-c-10) |
| (I-62) | (I-a-3) | (I-c-10) |
| (I-63) | (I-a-4) | (I-c-10) |
| (I-64) | (I-a-5) | (I-c-10) |
| (I-65) | (I-a-6) | (I-c-10) |
| (I-66) | (I-a-7) | (I-c-10) |
| (I-67) | (I-a-1) | (I-c-11) |
| (I-68) | (I-a-2) | (I-c-11) |
| (I-69) | (I-a-3) | (I-c-11) |
| (I-70) | (I-a-5) | (I-c-11) |
| (I-71) | (I-a-7) | (I-c-11) |
| (I-72) | (I-a-1) | (I-c-12) |
| (I-73) | (I-a-2) | (I-c-12) |
| (I-74) | (I-a-3) | (I-c-12) |
| (I-75) | (I-a-5) | (I-c-12) |
| (I-76) | (I-a-7) | (I-c-12) |
| (I-77) | (I-a-1) | (I-c-13) |
| (I-78) | (I-a-4) | (I-c-13) |
| (I-79) | (I-a-5) | (I-c-13) |
| (I-80) | (I-a-6) | (I-c-13) |
| (I-81) | (I-a-7) | (I-c-13) |
| (I-82) | (I-a-1) | (I-c-14) |
| (I-83) | (I-a-2) | (I-c-14) |
| (I-84) | (I-a-3) | (I-c-14) |
| (I-85) | (I-a-4) | (I-c-14) |
| (I-86) | (I-a-5) | (I-c-14) |
| (I-87) | (I-a-6) | (I-c-14) |
| (I-88) | (I-a-7) | (I-c-14) |

TABLE 4

| SALT (I) | Anion | Organic Cation |
|---|---|---|
| (I-89) | (I-a-1) | (I-c-15) |
| (I-90) | (I-a-2) | (I-c-15) |
| (I-91) | (I-a-3) | (I-c-15) |
| (I-92) | (I-a-5) | (I-c-15) |
| (I-93) | (I-a-7) | (I-c-15) |
| (I-94) | (I-a-1) | (I-c-16) |
| (I-95) | (I-a-2) | (I-c-16) |
| (I-96) | (I-a-3) | (I-c-16) |
| (I-97) | (I-a-5) | (I-c-16) |
| (I-98) | (I-a-7) | (I-c-16) |
| (I-99) | (I-a-1) | (I-c-17) |
| (I-100) | (I-a-2) | (I-c-17) |
| (I-101) | (I-a-3) | (I-c-17) |
| (I-102) | (I-a-5) | (I-c-17) |
| (I-103) | (I-a-7) | (I-c-17) |
| (I-104) | (I-a-1) | (I-c-18) |
| (I-105) | (I-a-2) | (I-c-18) |
| (I-106) | (I-a-3) | (I-c-18) |
| (I-107) | (I-a-5) | (I-c-18) |
| (I-108) | (I-a-7) | (I-c-18) |
| (I-109) | (I-a-1) | (I-c-19) |
| (I-110) | (I-a-5) | (I-c-19) |
| (I-111) | (I-a-7) | (I-c-19) |
| (I-112) | (I-a-1) | (I-c-20) |
| (I-113) | (I-a-4) | (I-c-20) |
| (I-114) | (I-a-5) | (I-c-20) |
| (I-115) | (I-a-6) | (I-c-20) |
| (I-116) | (I-a-7) | (I-c-20) |
| (I-117) | (I-a-1) | (I-c-21) |
| (I-118) | (I-a-2) | (I-c-21) |

TABLE 5

| SALT (I) | Anion | Organic Cation |
|---|---|---|
| (I-119) | (I-a-3) | (I-c-21) |
| (I-120) | (I-a-5) | (I-c-21) |
| (I-121) | (I-a-7) | (I-c-21) |
| (I-122) | (I-a-1) | (I-c-22) |
| (I-123) | (I-a-2) | (I-c-22) |
| (I-124) | (I-a-3) | (I-c-22) |
| (I-125) | (I-a-5) | (I-c-22) |
| (I-126) | (I-a-7) | (I-c-22) |
| (I-127) | (I-a-1) | (I-c-23) |
| (I-128) | (I-a-5) | (I-c-23) |
| (I-129) | (I-a-7) | (I-c-23) |
| (I-130) | (I-a-1) | (I-c-24) |
| (I-131) | (I-a-2) | (I-c-24) |
| (I-132) | (I-a-3) | (I-c-24) |
| (I-133) | (I-a-5) | (I-c-24) |
| (I-134) | (I-a-7) | (I-c-24) |

Among them, Preferred are the following salts.

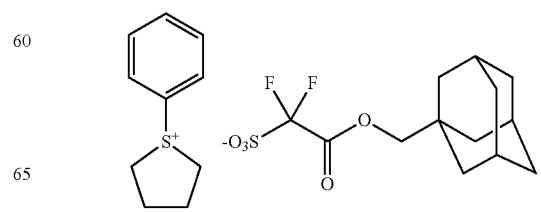

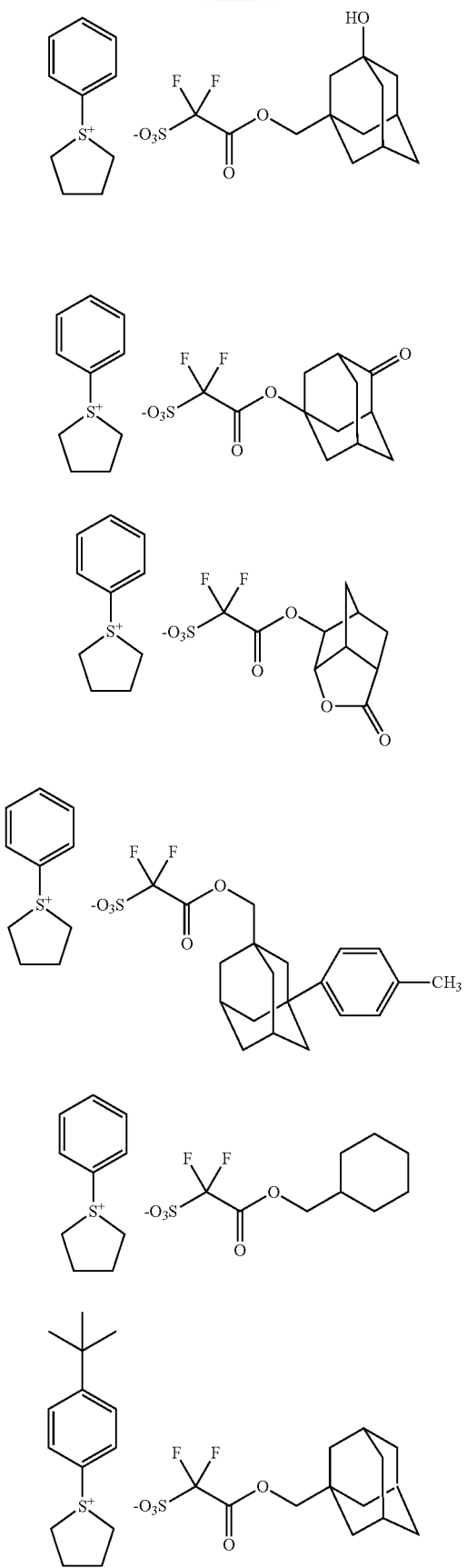

51
-continued
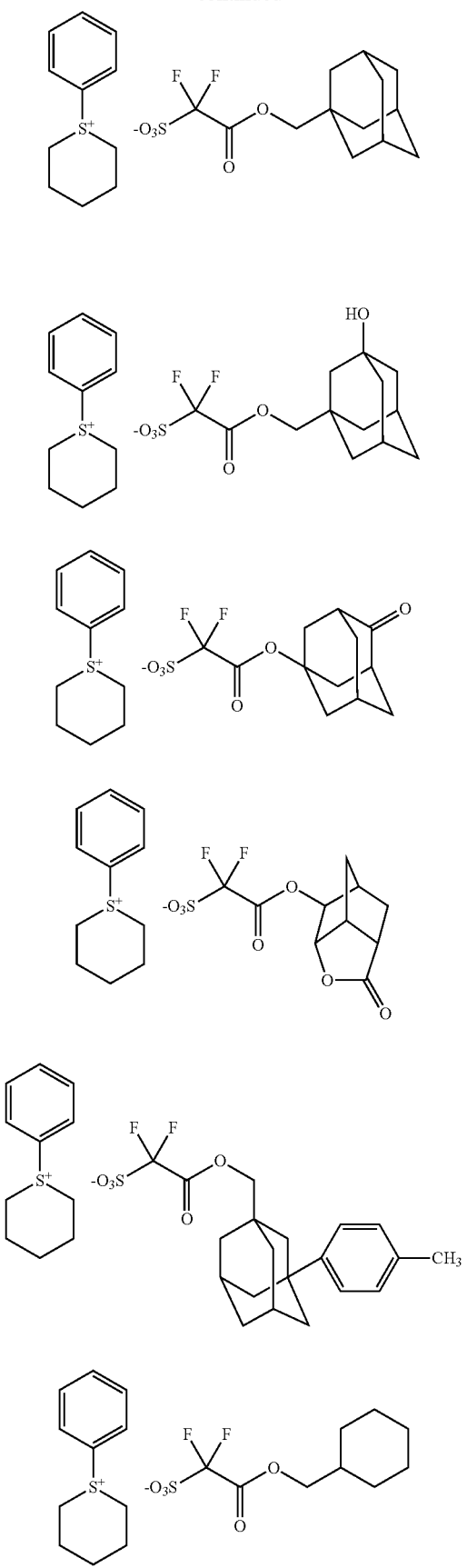
52
-continued
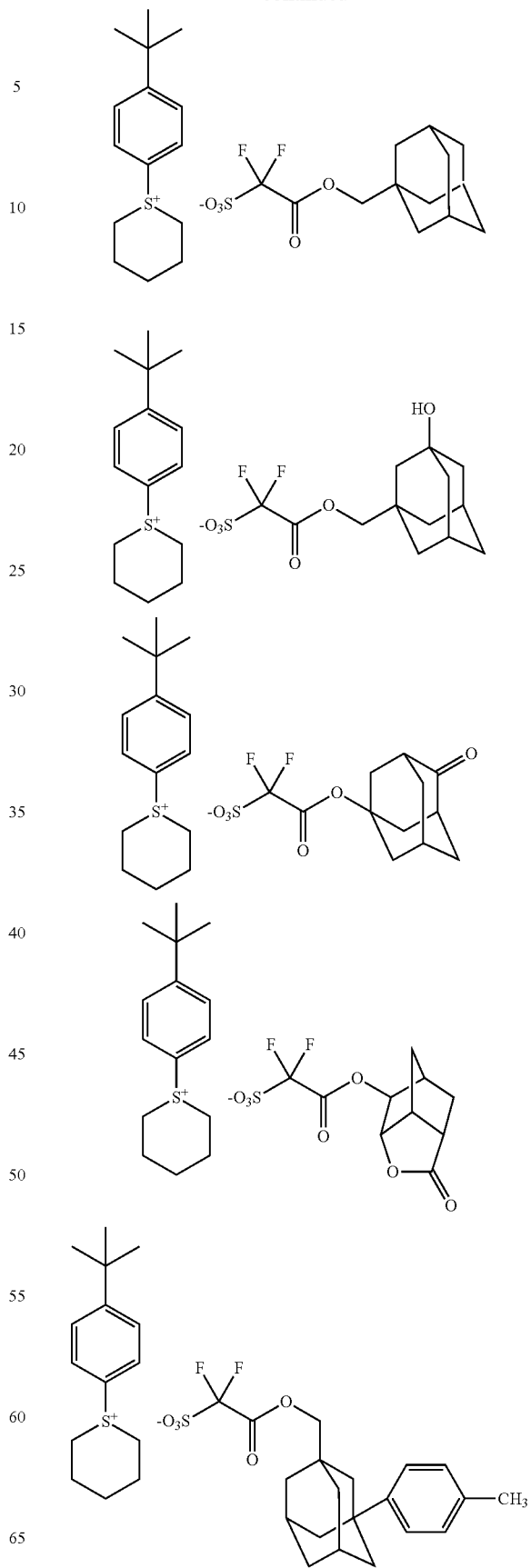

53
-continued
54
-continued
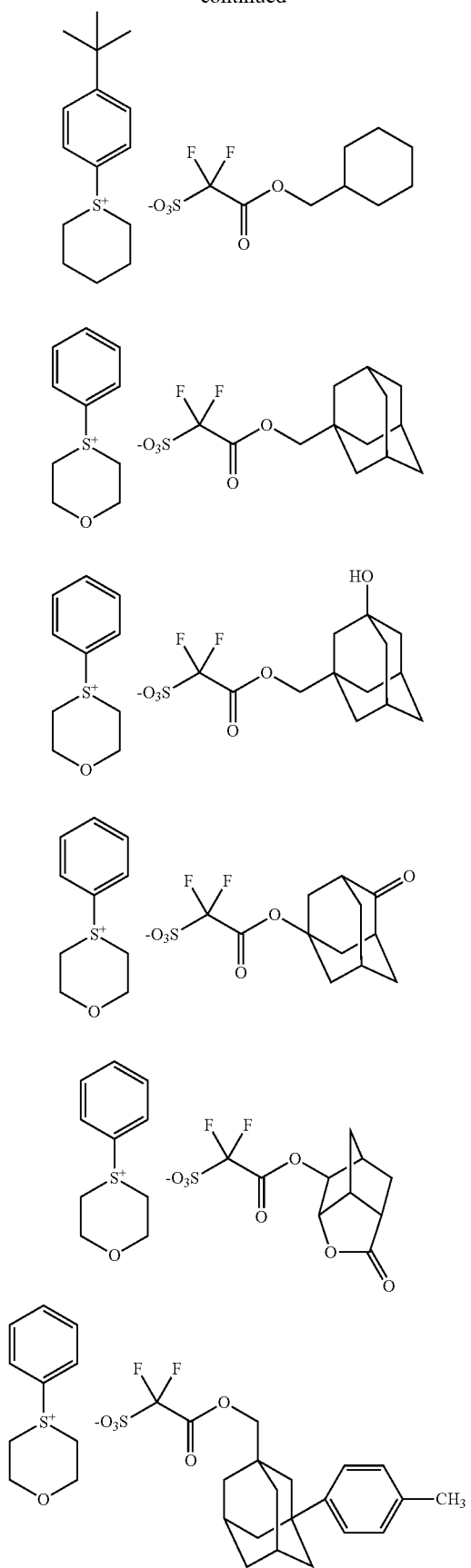
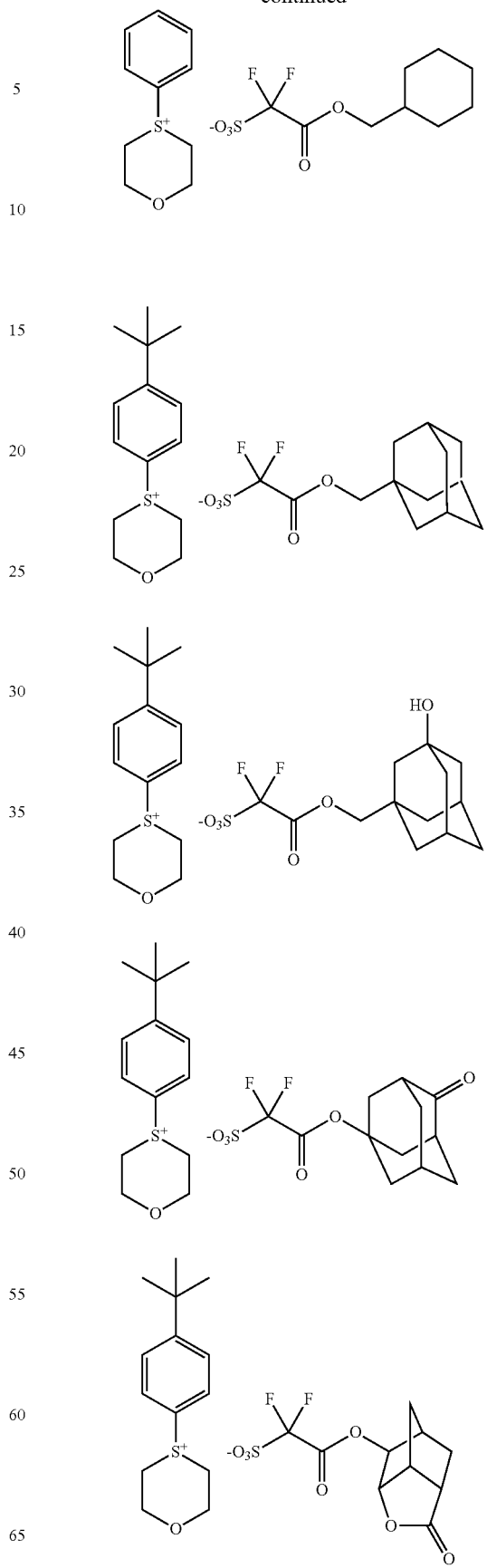

55
-continued
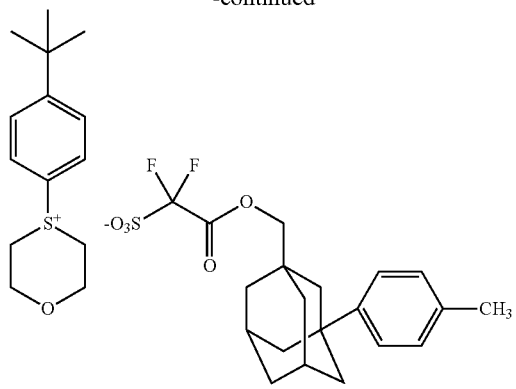
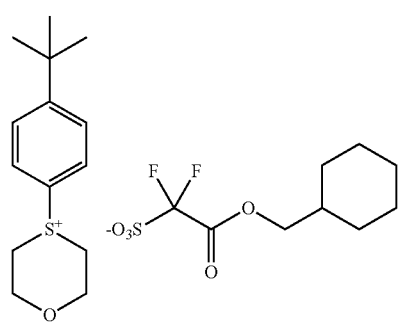
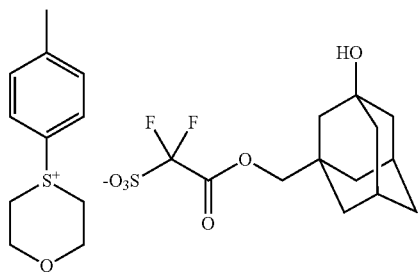
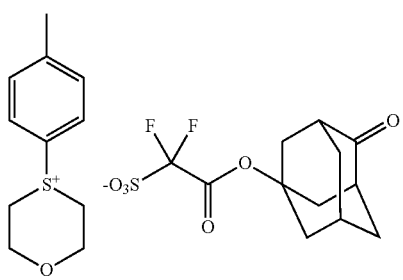
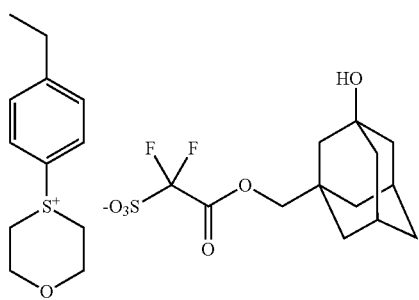
56
-continued
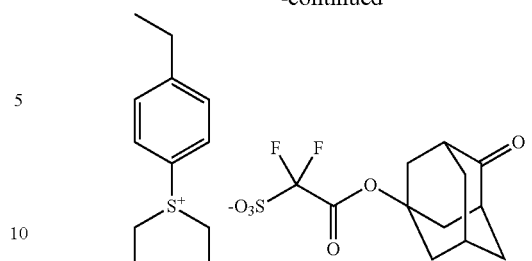
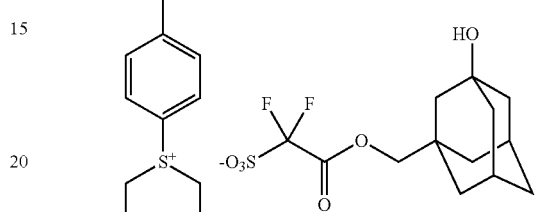
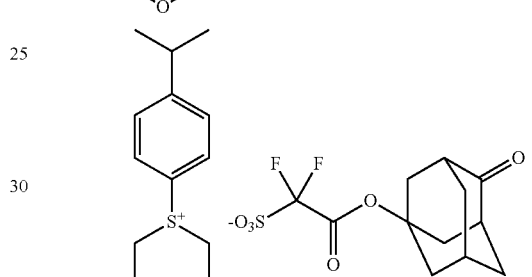
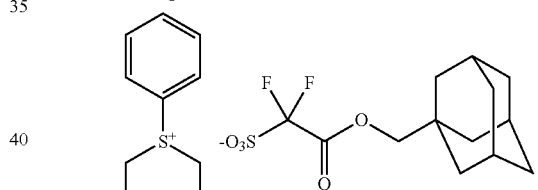
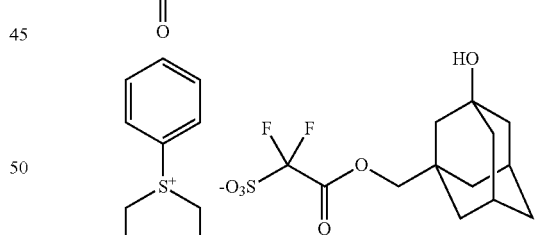
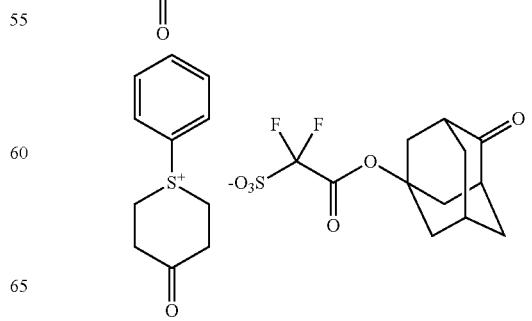

-continued

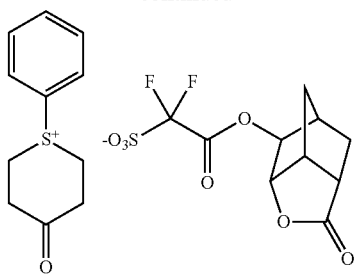

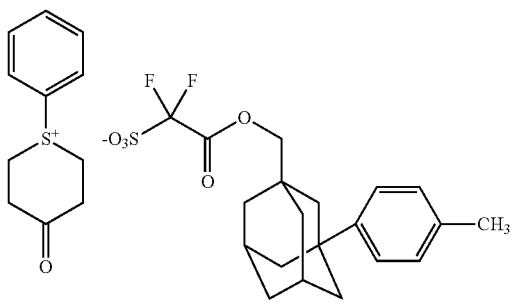

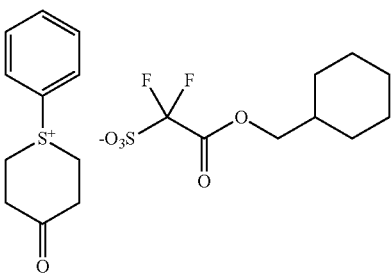

SALT (I) can be produced by reacting a salt represented by the formula (I-a) with a salt represented by the formula (I-b) in a solvent such as chloroform.

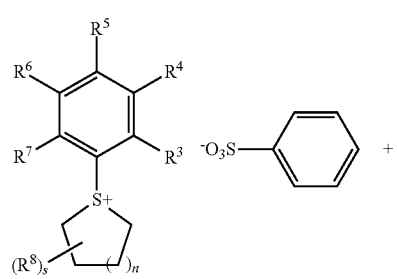

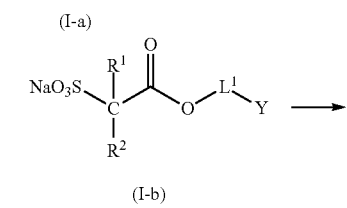

-continued

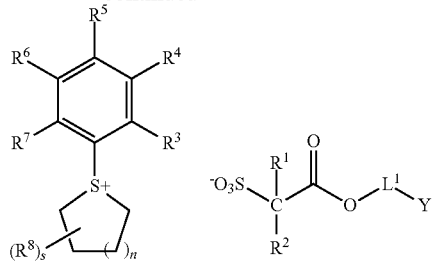

(I)

wherein $R^1$, $R^2$, $R^3$, $R^4$, $R^5$, $R^6$, $R^7$, $R^8$, $L^1$, s, n and Y are the same as defined above.

The salt represented by the formula (I-b) can be produced according to the method described in JP 2008-209917 A.

The salt represented by the formula (I-a) can be produced by reacting a salt represented by the formula (I-c) with a compound represented by the formula (I-d) in a solvent such as monochlorobenzene in the presence of a catalyst such as copper (II) dibenzoate.

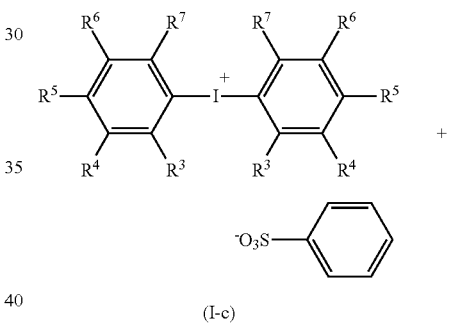

(I-c)

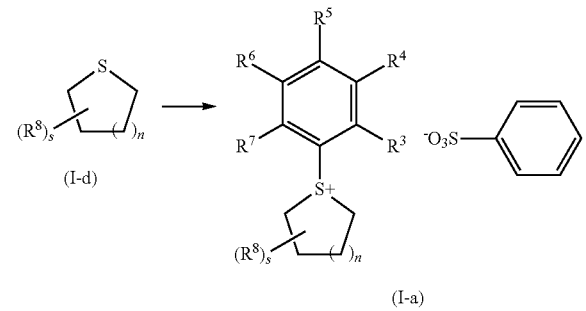

(I-a)

wherein $R^3$, $R^4$, $R^5$, $R^6$, $R^7$, $R^8$, s and n are the same as defined above.

Examples of the salt represented by the formula (I-c) include diphenyliodonium benzenesulfonate. Examples of the compound represented by the formula (I-d) include pentamethylenesulfide, 1,4-thioxane and tetrahydrothiophene.

SALT (I) can also be produced by reacting a salt represented by the formula (I-a') with a compound represented by the formula (I-b') in a solvent such as monochlorobenzene in the presence of a catalyst such as copper (II) dibenzoate.

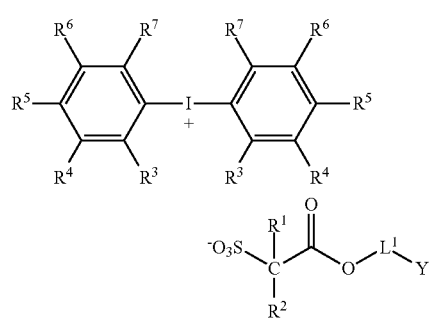

(I-a')

+

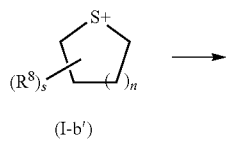

(I-b')

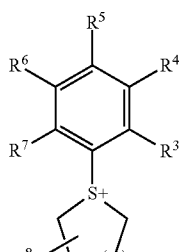

(I)

wherein $R^1$, $R^2$, $R^3$, $R^4$, $R^5$, $R^6$, $R^7$, $R^8$, $L^1$, s, n and Y are the same as defined above.

Examples of the compound represented by the formula (I-b') include pentamethylenesulfide, 1,4-thioxane and tetrahydrothiophene.

The salt represented by the formula (I-a') can be produced by reacting a salt represented by the formula (I-c') with a compound represented by the formula (I-d') in a solvent such as chloroform and water.

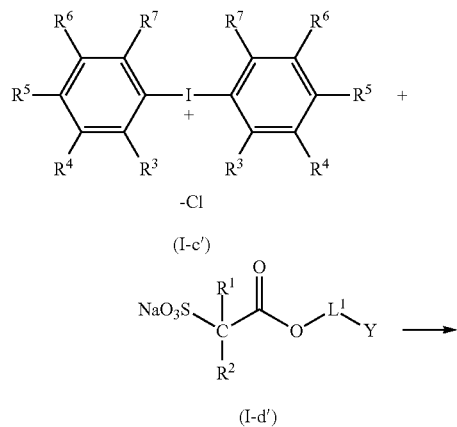

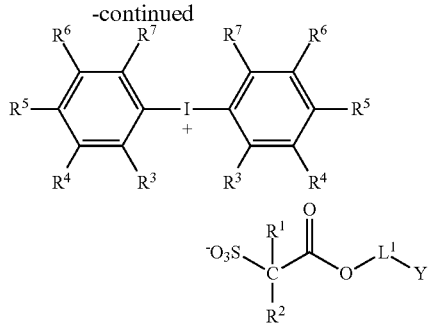

(I-a')

wherein $R^1$, $R^2$, $R^3$, $R^4$, $R^5$, $R^6$, $R^7$, $L^1$ and Y are the same as defined above.

Examples of the salt represented by the formula (I-c') include diphenyliodonium chloride. The salt represented by the formula (I-d') can be produced according to the method described in JP 2008-209917 A.

The acid generator of the present invention comprises SALT (I). The acid generator of the present invention can contain two or more kinds of SALT (I). The acid generator of the present invention can contain one or more known acid generators other than SALT (I) in addition to SALT (I). Examples of the known acid generators other than SALT (I) include a salt consisting of the above-mentioned organic cation of SALT (I) and a known anion other than the above-mentioned anion of SALT (I), and a salt consisting of the above-mentioned anion of SALT (I) and a known organic cation other than the above-mentioned anion of SALT (I).

Examples of the known acid generators other than SALT (I) include a salt consisting of the anion of SALT (I) and triarylsulfonium cation. Specific examples thereof include the following salts represented by the formulae (B1-1) to (B1-17), and the salt containing a triphenylsulfonium cation or a tritolysulfonium cation is more preferable, and the salts represented by the formulae (B1-1), (B1-2), (B1-3), (B1-6), (B1-11), (B1-12), (B1-13) and (B1-14) are especially preferable.

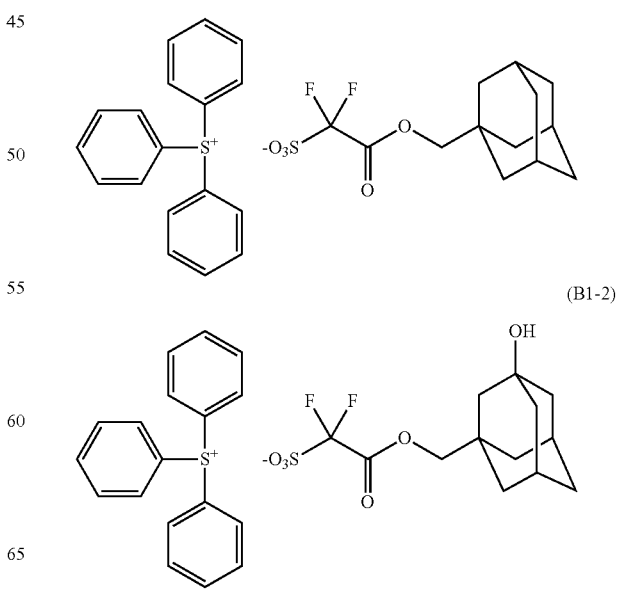

(B1-3)
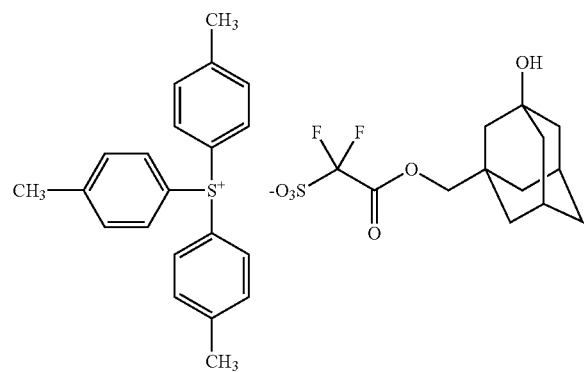
(B1-7)
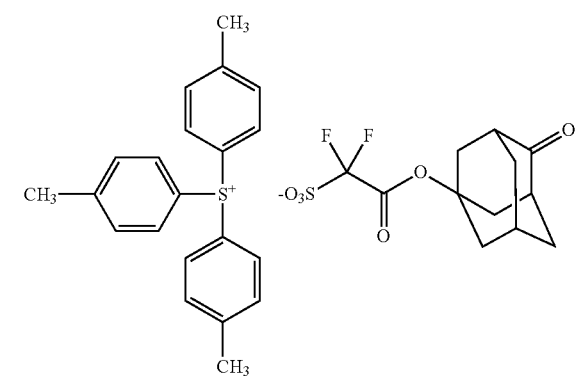
(B1-4)
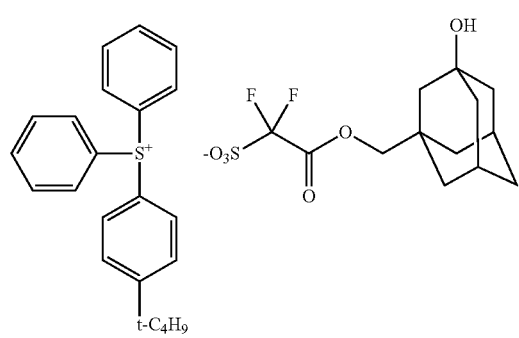
(B1-8)
(B1-5)
(B1-9)
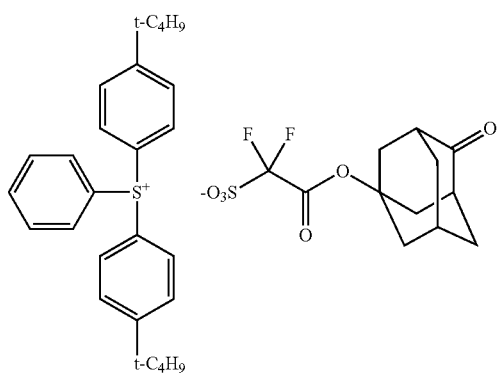
(B1-6)
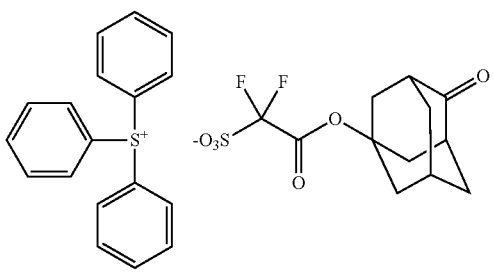
(B1-10)
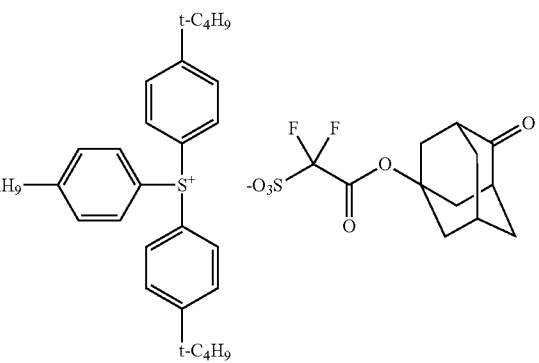

-continued (B1-11)
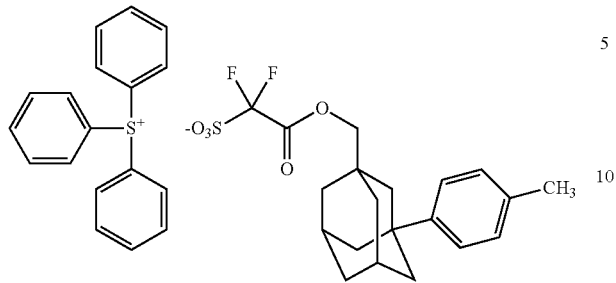

(B1-12)
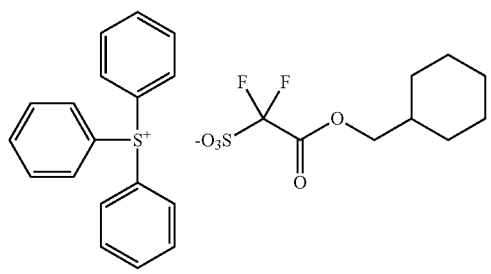

(B1-13)
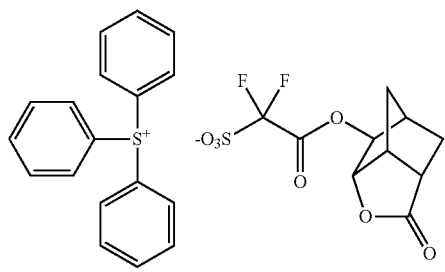

(B1-14)
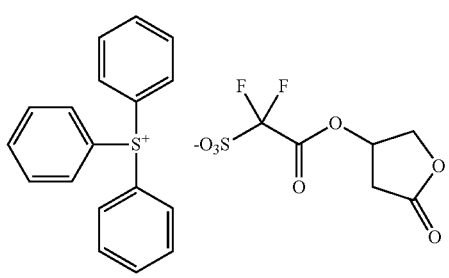

(B1-15)
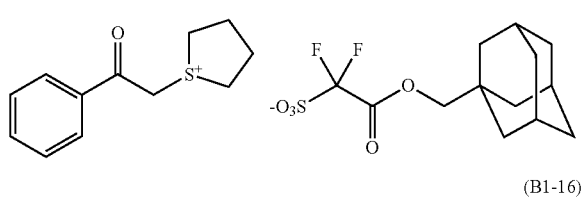

(B1-16)
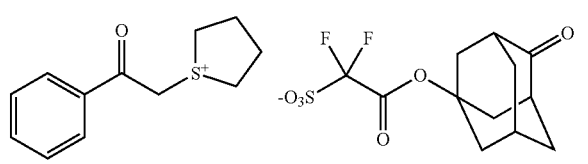

-continued (B1-17)
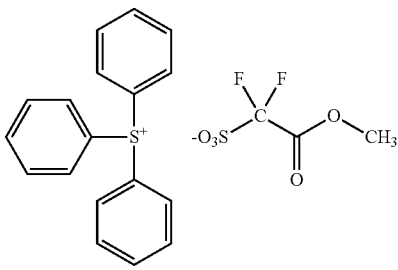

The acid generator of the present invention may consist of SALT (I). When the acid generator of the present invention contains SALT (I) and the acid generator other than SALT (I), the content of SALT (I) is preferably 10 parts by mass or more and more preferably 30 parts by mass or more per 100 parts by masst of the acid generator of the present invention, and the content of SALT (I) is preferably 90 parts by mass or less and more preferably 70 parts by mass or less per 100 parts by mass of the acid generator of the present invention.

Next, the photoresist composition of the present invention will be illustrated.

The photoresist composition of the present invention comprises the acid generator of the present invention and a resin having an acid-labile group, being insoluble or poorly soluble in an aqueous alkali solution but becoming soluble in an aqueous alkali solution by the action of an acid.

The resin is insoluble or poorly soluble in an alkali aqueous solution but becomes soluble in an alkali aqueous solution by the action of an acid. The resin has one or more acid-labile groups. In this specification, "an acid-labile group" means a group capable of being eliminated by the action of an acid.

Examples of the acid-labile group include a group represented by the formula (1):

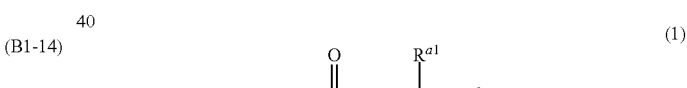

(1)

wherein $R^{a1}$, $R^{a2}$ and $R^{a3}$ independently each represent a C1-C8 aliphatic hydrocarbon group or a C3-C20 alicyclic hydrocarbon group, and $R^{a1}$ and $R^{a2}$ can be bonded each other to form a C3-C20 ring together with a carbon atom to which $R^{a1}$ and $R^{a2}$ are bonded, and one or more —CH$_2$— in the aliphatic hydrocarbon group, the alicyclic hydrocarbon group and the ring can be replaced by —O—, —S— or —CO—.

Examples of the aliphatic hydrocarbon group include a C1-C8 alkyl group. Specific examples of the C1-C8 alkyl group include a methyl group, an ethyl group, a propyl group, an isopropyl group, a butyl group, a pentyl group, a hexyl group, a heptyl group and an octyl group. The alicyclic hydrocarbon group may be monocyclic or polycyclic. Examples of the alicyclic hydrocarbon group include a monocyclic alicyclic hydrocarbon group such as a C3-C20 cycloalkyl group (e.g. a cyclopentyl group, a cyclohexyl group, a methylcyclohexyl group, a dimethylcyclohexyl group, a cycloheptyl group and a cyclooctyl group) and a polycyclic alicyclic hydrocarbon group such as a decahydronaphthyl group, an adamantyl group, a norbornyl group, a methylnorbornyl group, and the followings:

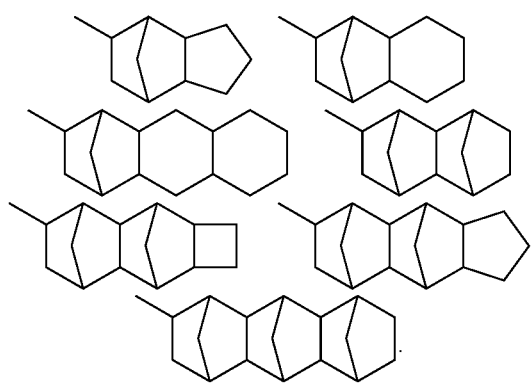

The alicyclic hydrocarbon group preferably has 3 to 16 carbon atoms.

Examples of the ring formed by bonding $R^{a1}$ and $R^{a2}$ each other include the following groups and the ring preferably has 3 to 12 carbon atoms.

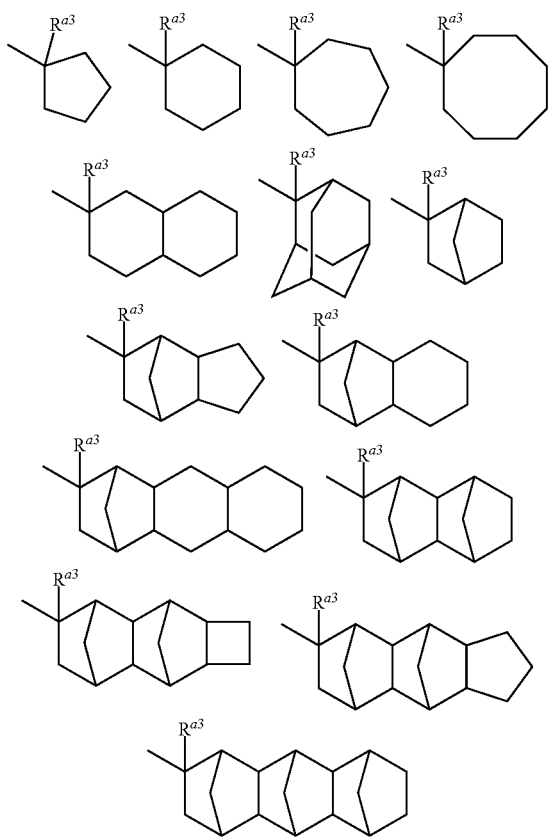

wherein $R^{a3}$ is the same as defined above.

The group represented by the formula (I) wherein $R^{a1}$, $R^{a2}$ and $R^{a3}$ independently each represent a C1-C8 alkyl group such as a tert-butyl group, the group represented by the formula (1) wherein $R^{a1}$ and $R^{a2}$ are bonded each other to form an adamantyl ring and $R^{a3}$ is a C1-C8 alkyl group such as a 2-alkyl-2-adamantyl group, and the group represented by the formula (1) wherein $R^{a1}$ and $R^{a2}$ are C1-C8 alkyl groups and $R^{a3}$ is an adamantyl group such as a 1-(1-adamantyl)-1-alkylalkoxycarbonyl group are preferable.

Examples of the acid-labile group include a group represented by the formula (20):

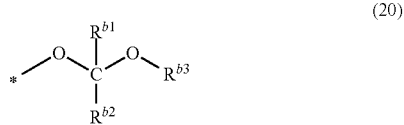

(20)

wherein $R^{b1}$ and $R^{b2}$ independently each represent a hydrogen atom or a C1-C12 hydrocarbon group, and $R^{b3}$ represents a C1-C20 hydrocarbon group, and $R^{b2}$ and $R^{b3}$ can be bonded each other to form a C3-C20 ring together with the carbon atom and the oxygen atom to which they are bonded, and one or more —$CH_2$— in the hydrocarbon group and the ring can be replaced by —O—, —S— or —CO—.

The group represented by the formula (20) has an acetal structure.

Examples of the hydrocarbon group include an aliphatic hydrocarbon group, an alicyclic hydrocarbon group and an aromatic hydrocarbon group. Examples of the aliphatic hydrocarbon group and the alicyclic hydrocarbon group include the same as described above. Examples of the aromatic hydrocarbon group include an aryl group such as a phenyl group, a naphthyl group, a p-methylphenyl group, a p-tert-butylphenyl group, a p-adamantylphenyl group, a tolyl group, a xylyl group, a cumyl group, a mesityl group, a biphenyl group, an anthryl group, a phenanthryl group, a 2,6-diethylphenyl group and a 2-methyl-6-ethylphenyl group.

It is preferred that at least one of $R^{b1}$ and $R^{b2}$ is a hydrogen atom.

Examples of the group represented by the formula (20) include the following.

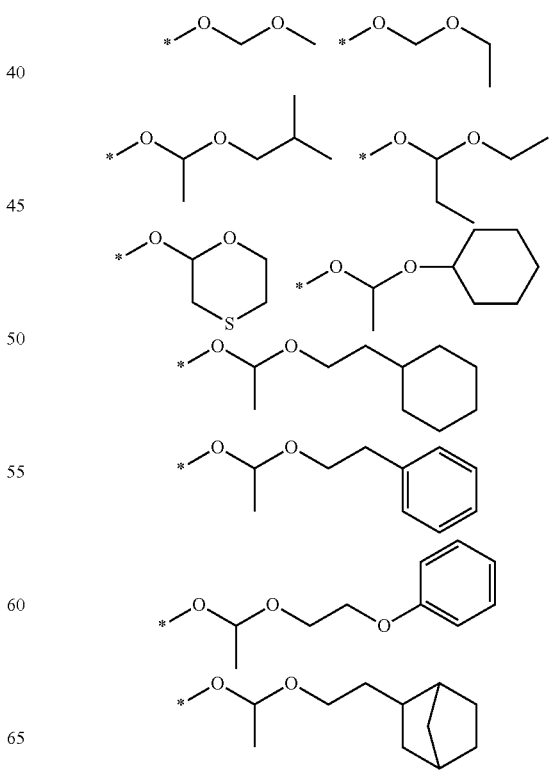

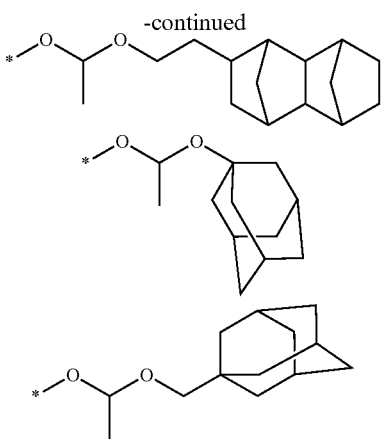

The compound having an acid-labile group is preferably a monomer having an acid-labile group in its side chain and a carbon-carbon double bond, and is more preferably an acrylate monomer having an acid-labile group in its side chain or a methacryalte monomer having an acid-labile group in its side chain.

A monomer having the group represented by the formula (10) or (20) in its side chain and a carbon-carbon double bond is preferable, and an acrylate monomer having the group represented by the formula (10) in its side chain or a methacryalte monomer having the group represented by the formula (10) in its side chain is more preferable.

An acrylate monomer having the group represented by the formula (10) in which $R^{a1}$ and $R^{a2}$ are bonded each other to form a C5-C20 alicycle together with the carbon atom to which they are bonded in its side chain or a methacryalte monomer having the group represented by the formula (10) in which $R^{a1}$ and $R^{a2}$ are bonded each other to form a C5-C20 alicycle together with the carbon atom to which they are bonded in its side chain is especially preferable.

Preferable examples of the compound having an acid-labile group include monomers represented by the formulae (a1-1) and (a1-2):

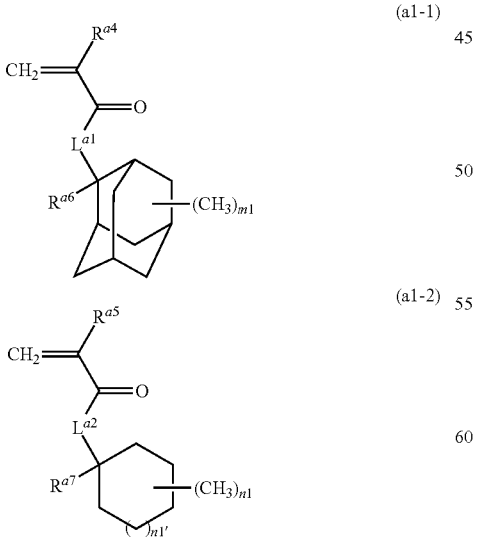

wherein $R^{a4}$ and $R^{a5}$ each independently represents a hydrogen atom or a methyl group, $R^{a6}$ and $R^{a7}$ each independently represents a C1-C8 aliphatic hydrocarbon group or a C3-C10 alicyclic hydrocarbon group, $L^{a1}$ and $L^{a2}$ each independently represents *—O— or *—O—$(CH_2)_{k1}$—CO—O— in which * represents a binding position to —CO—, and k1 represents an integer of 1 to 7, and m1 represents an integer of 0 to 14, n1 represents an integer of 0 to 10, and n1' represents 0 or 1.

The aliphatic hydrocarbon group preferably has 1 to 6 carbon atoms, and the alicyclic hydrocarbon group preferably has 3 to 8 carbon atoms and more preferably 3 to 6 carbon atoms. The alicyclic hydrocarbon group is preferably a saturated aliphatic cyclic hydrocarbon group.

Examples of the aliphatic hydrocarbon group include a C1-C8 alkyl group such as a methyl group, an ethyl group, a propyl group, an isopropyl group, a butyl group, a tert-butyl group, a 2,2-dimethylethyl group, a 1-methylpropyl group, a 2,2-dimethylpropyl group, a 1-ethylpropyl group, a 1-methylbutyl group, a 2-methylbutyl group, a 3-methylbutyl group, a 1-propylbutyl group, a pentyl group, a 1-methylpentyl group, a hexyl group, a 1,4-dimethylhexyl group, a heptyl group, a 1-methylheptyl group and an octyl group. Examples of the alicyclic hydrocarbon group include a monocyclic alicyclic hydrocarbon group such as a cyclohexyl group, a methylcyclohexyl group, a dimethylcyclohexyl group, a cycloheptyl group and a methylcycloheptyl group, and a polycyclic alicyclic hydrocarbon group such as a decahydronaphthyl group, an adamantyl group, a norbornyl group, a methylnorbornyl group and the following.

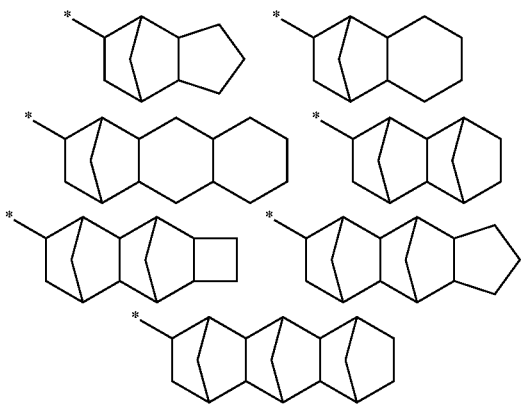

$L^{a1}$ is preferably *—O— or *—O—$(CH_2)_{f1}$—CO—O— in which * represents a binding position to —CO—, and f1 represents an integer of 1 to 4, and is more preferably *—O— or *—O—$CH_2$—CO—O—, and is especially preferably *—O—. $L^{a2}$ is preferably *—O— or *—O—$(CH_2)_{f1}$—CO—O— in which * represents a binding position to —CO—, and f1 is the same as defined above, and is more preferably *—O— or *—O—$CH_2$—CO—O—, and is especially preferably *—O—.

In the formula (a1-1), m1 is preferably an integer of 0 to 3, and is more preferably 0 or 1. In the formula (a1-2), n1 is preferably an integer of 0 to 3, and is more preferably 0 or 1, and n1' is preferably 0 or 1.

$R^{a4}$ and $R^{a5}$ are preferably methyl groups.

Examples of the monomer represented by the formula (a1-1) include the monomers described in JP 2010-204646 A, and the following monomers represented by the formulae (a1-1-1) to (a1-1-6) are preferable and the following monomers represented by the formulae (a1-1-1) to (a1-1-3) are more preferable.

(a1-1-1)
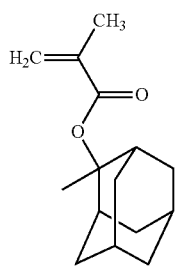

(a1-1-2)
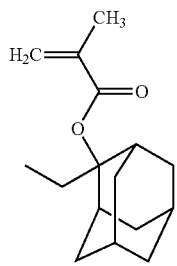

(a1-1-3)
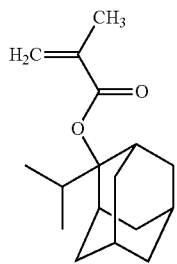

(a1-1-4)
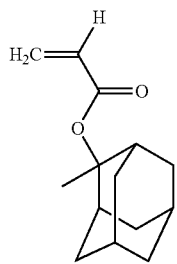

(a1-1-5)
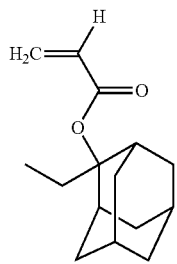

(a1-1-6)
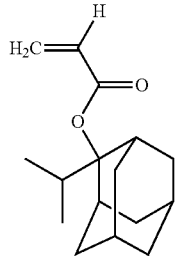

Examples of the monomer represented by the formula (a1-2) include 1-ethylcyclopentan-1-yl acrylate, 1-ethylcyclopentan-1-yl methacrylate, 1-ethylcyclohexan-1-yl acrylate, 1-ethylcyclohexan-1-yl methacrylate, 1-ethylcycloheptan-1-yl acrylate, 1-ethylcycloheptan-1-yl methacrylate, 1-methylcyclopentan-1-yl acrylate, 1-methylcyclopentan-1-yl methacrylate, 1-isopropylcyclopentan-1-yl acrylate and 1-isopropylcyclopentan-1-yl methacrylate, and the monomers represented by the formulae (a1-2-1) to (a1-2-6) are preferable and the following monomers represented by the formulae (a1-2-3) to (a1-2-4) are more preferable.

(a1-2-1)
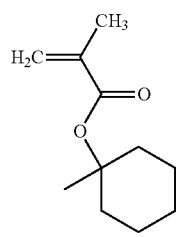

(a1-2-2)
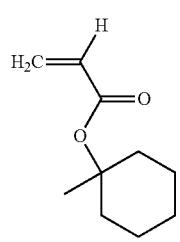

(a1-2-3)
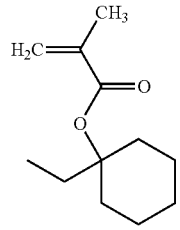

(a1-2-4)
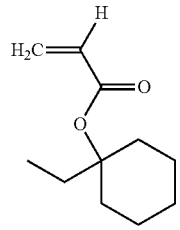

(a1-2-5)
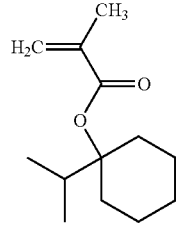

(a1-2-6)

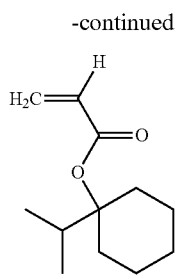

The content of the structural unit derived from a monomer having an acid-labile group in the resin is usually 10 to 95% by mole, preferably 15 to 90% by mole and more preferably 20 to 85% by mole based on 100% by mole of all the structural units of the resin. The content of the structural unit derived from a monomer having an acid-labile group in the resin can be adjusted by adjusting the amount of the monomer having an acid-labile group based on the total amount of the monomers used for producing the resin.

When the resin contains the structural unit derived from the monomer represented by the formula (a1-1) or (a1-2), the content of the structural unit derived from the monomer represented by the formula (a1-1) or (a1-2) in the resin is usually 10 to 95% by mole, preferably 15 to 90% by mole and more preferably 20 to 85% by mole and especially preferably 25 to 60% by mole based on 100% by mole of all the structural units of the resin.

Other examples of the monomer having an acid-labile group include a monomer represented by the formula (a1-3):

(a1-3)

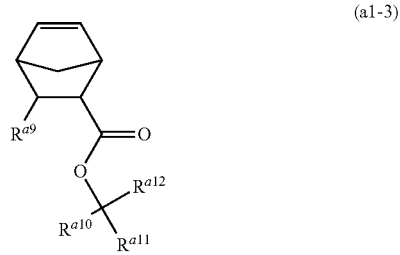

wherein $R^{a9}$ represents a hydrogen atom, a C1-C3 alkyl group which can have one or more hydroxyl groups, a carboxyl group, a cyano group or a —COOR$^{a13}$ group in which $R^{a13}$ represents a C1-C8 alkyl group or a C3-C20 alicyclic hydrocarbon group, and a group composed of a C1-C8 alkyl group and a C3-C20 alicyclic hydrocarbon group, and the alkyl group and the alicyclic hydrocarbon group can have one or more hydroxyl groups, and one or more —CH$_2$— in the alkyl group and the alicyclic hydrocarbon group can be replaced by —O— or —CO—, $R^{a10}$, $R^{a11}$ and $R^{a12}$ each independently represent a C1-C12 alkyl group or a C3-C20 alicyclic hydrocarbon group, and $R^{a10}$ and $R^{a11}$ can be bonded each other to form a C3-C20 ring together with the carbon atom to which $R^{a10}$ and $R^{a11}$ are bonded, and the alkyl group and the alicyclic hydrocarbon group can have one or more hydroxyl groups, and one or more —CH$_2$— in alkyl group and the alicyclic hydrocarbon group can be replaced by —O— or —CO—.

Examples of the C1-C3 alkyl group which can have one or more hydroxyl groups include a methyl group, an ethyl group, a propyl group, a hydroxymethyl group and a 2-hydroxyethyl group. Examples of $R^{a13}$ include a methyl group, an ethyl group, a propyl group, a 2-oxo-oxolan-3-yl group and a 2-oxo-oxolan-4-yl group. Examples of $R^{a10}$, $R^{a11}$ and $R^{a12}$ include a methyl group, an ethyl group, a cyclohexyl group, a methylcyclohexyl group, a hydroxycyclohexyl group, an oxocyclohexyl group and an adamantyl group, and examples of the C3-C20 ring formed by bonding $R^{a10}$ and $R^{a11}$ each other together with the carbon atom to which $R^{a10}$ and $R^{a11}$ are bonded include a cyclohexane ring and an adamantane ring.

Examples of the monomer represented by the formula (a1-3) include tert-butyl 5-norbornene-2-carboxylate, 1-cyclohexyl-1-methylethyl 5-norbornene-2-carboxylate, 1-methylcyclohexyl 5-norbornene-2-carboxylate, 2-methyl-2-adamantyl 5-norbornene-2-carboxylate, 2-ethyl-2-adamantyl 5-norbornene-2-carboxylate, 1-(4-methylcyclohexyl)-1-methylethyl 5-norbornene-2-carboxylate, 1-(4-hydroxylcyclohexyl)-1-methylethyl 5-norbornene-2-carboxylate, 1-methyl-1-(4-oxocyclohexyl)ethyl 5-norbornene-2-carboxylate and 1-(1-adamantyl)-1-methylethyl 5-norbornene-2-carboxylate.

When the resin has a structural unit derived from the monomer represented by the formula (a1-3), the photoresist composition having excellent resolution and higher dry-etching resistance tends to be obtained.

When the resin contains the structural unit derived form the monomer represented by the formula (a1-3), the content of the structural unit derived from the monomer represented by the formula (a1-3) is usually 10 to 9.5% by mole and preferably 15 to 90% by mole and more preferably 20 to 85% by mole based on total molar of all the structural units of the resin.

Other examples of the compound having an acid-labile group include a monomer represented by the formula (a1-4):

(a1-4)

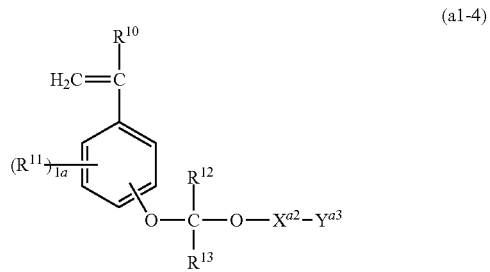

wherein $R^{10}$ represents a hydrogen atom, a halogen atom, a C1-C6 alkyl group or a C1-C6 halogenated alkyl group, $R^{11}$ is independently in each occurrence a halogen atom, a hydroxyl group, a C1-C6 alkyl group, a C1-C6 alkoxy group, a C2-C4 acyl group, a C2-C4 acyloxy group, an acryloyl group or a methacryloyl group, 1a represents an integer of 0 to 4, $R^{12}$ and $R^{13}$ each independently represent a hydrogen atom or a C1-C12 hydrocarbon group, $X^{a2}$ represents a single bond or a C1-C17 divalent saturated hydrocarbon group in which one or more —CH$_2$— can be replaced by —O—, —CO—, —S—, —SO$_2$— or —N(R$^c$)— wherein R$^c$ represents a hydrogen atom or a C1-C6 alkyl group, and $Y^{a3}$ represents a C1-C12 alkyl group, a C3-C18 alicyclic hydrocarbon group or a C6-C18 aromatic hydrocarbon group, and the C1-C17 divalent saturated hydrocarbon group , the C1-C12 alkyl group, the C3-C18 alicyclic hydrocarbon group and the C6-C18 aromatic hydrocarbon group can have one or more substituents selected from the group consisting of a halogen atom, a hydroxyl group, a C1-C6 alkyl group, a C1-C6 alkoxy group, a C2-C4 acyl group and a C2-C4 acyloxy group.

Examples of the halogen atom include a fluorine atom, a chlorine atom, a bromine atom and an iodine atom.

Examples of the C1-C6 alkyl group include a methyl group, an ethyl group, a propyl group, an isopropyl group, a butyl group, an isobutyl group, a sec-butyl group, a tert-butyl group, a pentyl group and a hexyl group, and a C1-C4 alkyl group is preferable and a C1-C2 alkyl group is more preferable and a methyl group is especially preferable.

Examples of the C1-C6 halogenated alkyl group include a trifluoromethyl group, a pentafluoroethyl group, a heptafluoropropyl group, a heptafluoroisopropyl group, a nonafluorobutyl group, a nonafluoro-sec-butyl group, a nonafluoro-tert-butyl group, a perfluoropentyl group, a perfluorohexyl group, a perchloromethyl group, a perbromomethyl group and a periodomethyl group.

Examples of the C1-C6 alkoxy group include a methoxy group, an ethoxy group, a propoxy group, an isopropoxy group, a butoxy group, an isobutoxy group, a sec-butoxy group, a tert-butoxy group, a pentyloxy group and a hexyloxy group, and a C1-C4 alkoxy group is preferable and a C1-C2 alkoxy group is more preferable and a methoxy group is especially preferable.

Examples of the C2-C4 acyl group include an acetyl group, a propionyl group and a butyryl group, and examples of the C2-C4 acyloxy group include an acetyloxy group, a propionyloxy group and a butyryloxy group.

Examples of the C1-C12 hydrocarbon group include a C1-C12 alkyl group such as a methyl group, an ethyl group, a propyl group, an isopropyl group, a butyl group, an isobutyl group, a sec-butyl group, a tert-butyl group, a pentyl group, a hexyl group, a heptyl group, an octyl group, a 2-ethylhexyl group, a nonyl group, a decyl group, an undecyl group and a dodecyl group, a C3-C12 alicyclic hydrocarbon group such as a cyclohexyl group, an adamantyl group, a 2-alkyl-2-adamantyl group, a 1-(1-adamantyl)-1-alkyl group and an isobornyl group, an C6-C12 aromatic hydrocarbon group and a group formed by combining one or more above-mentioned groups.

Examples of the C1-C17 divalent saturated hydrocarbon group include a C1-C17 alkanediyl group such as a methylene group, an ethylene group, a propane-1,3-diyl group, a butane-1,4-diyl group, a pentane-1,5-diyl group, a hexane-1,6-diyl group, a heptane-1,7-diyl group, an octane-1,8-diyl group, a nonane-1,9-diyl group, a decane-1,10-diyl group, a undecane-1,11-diyl group, a dodecane-1,12-diyl group, a tridecane-1,13-diyl group, a tetradecane-1,14-diyl group, a pentadecane-1,15-diyl group, a hexadecane-1,16-diyl group and a heptadecane-1,17-diyl group.

Examples of the C1-C12 alkyl group include a methyl group, an ethyl group, a propyl group, an isopropyl group, a butyl group, an isobutyl group, a sec-butyl group, a tert-butyl group, a pentyl group, a hexyl group, a heptyl group, an octyl group, a 2-ethylhexyl group, a nonyl group, a decyl group, an undecyl group and a dodecyl group. Examples of the C3-C18 alicyclic hydrocarbon group include a cyclopropyl group, a cyclobutyl group, a cyclopentyl group, a cyclohexyl group, a cycloheptyl group, a cyclooctyl group, a cyclononyl group, a cyclodecyl group, a norbornyl group, a 1-adamantyl group, a 2-adamantyl group, an isobornyl group and the following groups:

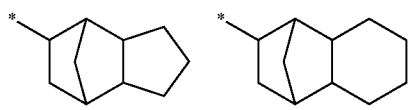

-continued

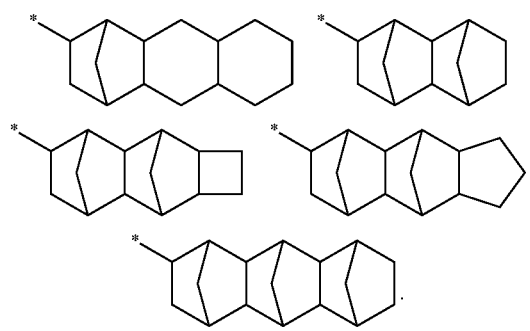

Examples of the C6-C18 aromatic hydrocarbon group include a phenyl group, a naphthyl group, an anthryl group, a p-methylphenyl group, a p-tert-butylphenyl group and a p-adamantylphenyl group.

Preferred substituents of $X^{a2}$ and $Y^{a3}$ is a hydroxyl group.

$R^{10}$ is preferably a C1-C4 alkyl group, more preferably a methyl group or an ethyl group, and still more preferably a methyl group. $R^{11}$ is preferably a C1-C4 alkyl group or a C1-C4 alkoxy group, more preferably a methyl group, an ethyl group, a methoxy group or an ethoxy group, and still more preferably a methyl group or a methoxy group.

$R^{12}$ is preferably an isopropyl group, a butyl group, a sec-butyl group, a tert-butyl group, a pentyl group, a hexyl group, an octyl group, a 2-ethylhexyl group, a cyclohexyl group, an adamantyl group, a 2-alkyl-2-adamantyl group, a 1-(1-adamantyl)-1-alkyl group and an isobornyl group. $R^{13}$ is preferably an isopropyl group, a butyl group, a sec-butyl group, a tert-butyl group, a pentyl group, a hexyl group, an octyl group, a 2-ethylhexyl group, a cyclohexyl group, an adamantyl group, a 2-alkyl-2-adamantyl group, a 1-(1-adamantyl)-1-alkyl group and an isobornyl group.

Examples of the monomer represented by the formula (a1-4) include the followings.

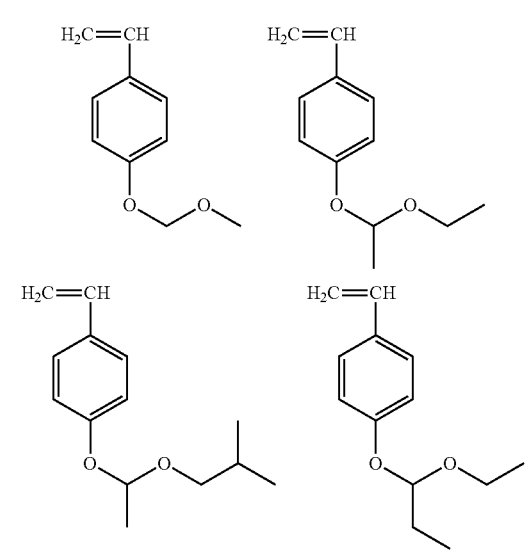

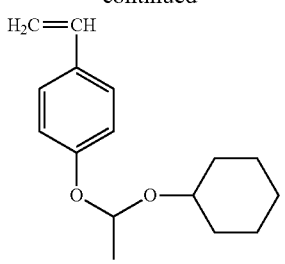
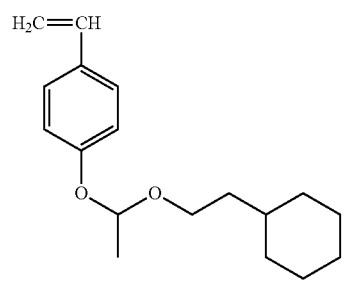
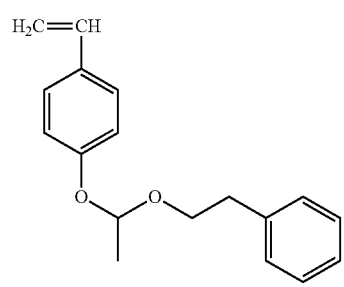
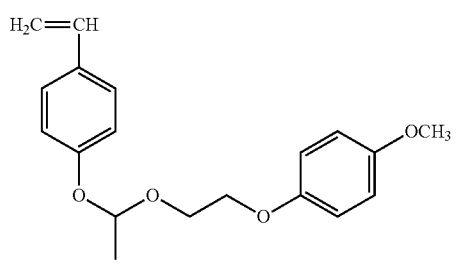
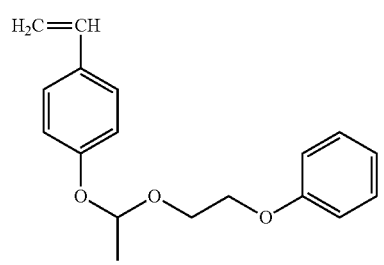
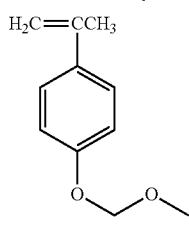
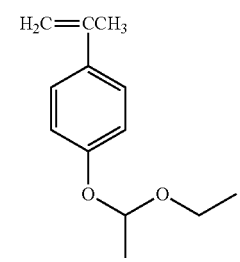
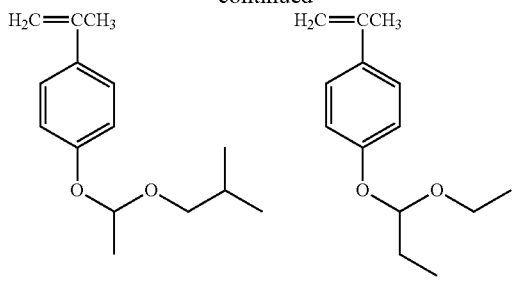
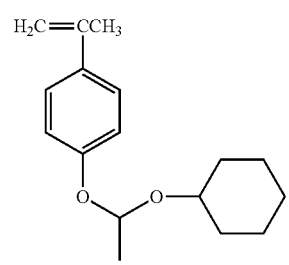
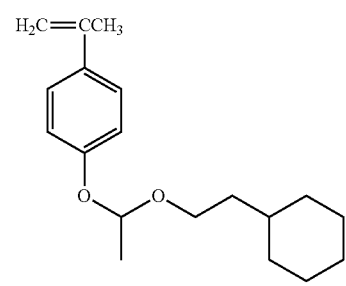
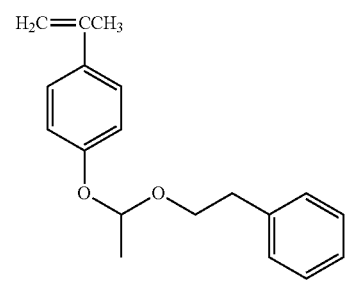
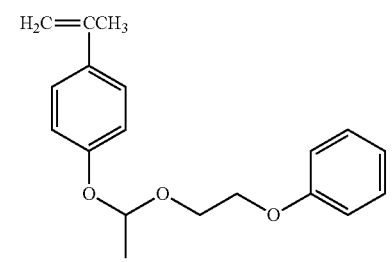
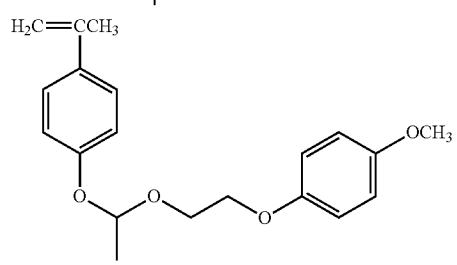

77
-continued
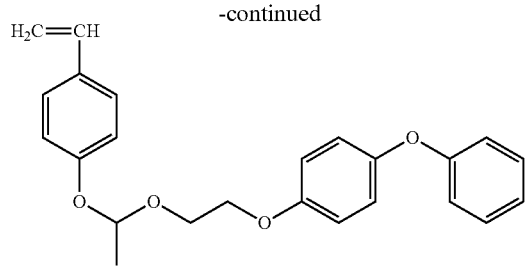
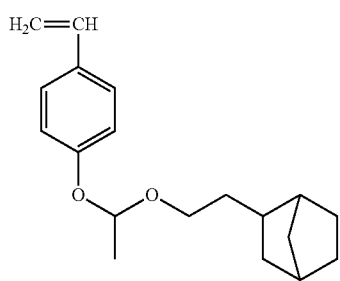
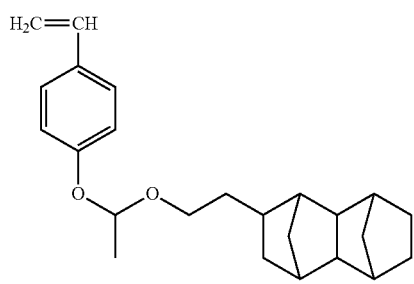
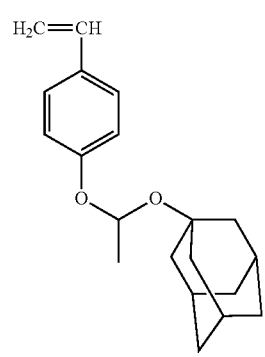
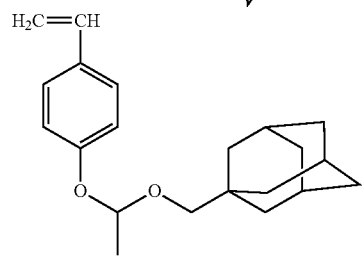
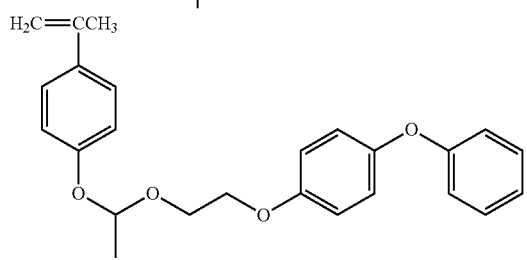
78
-continued
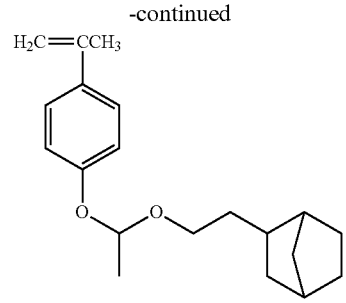
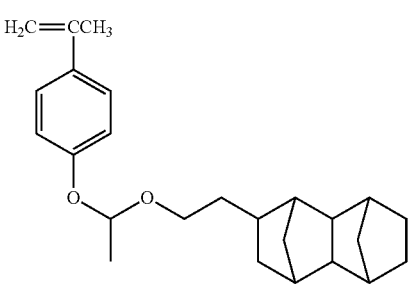
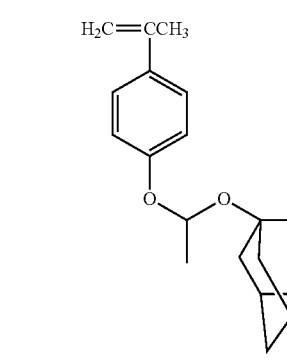
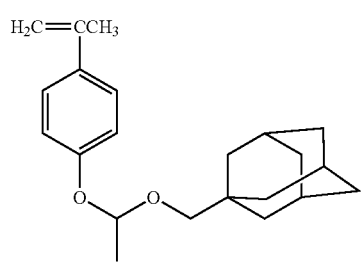
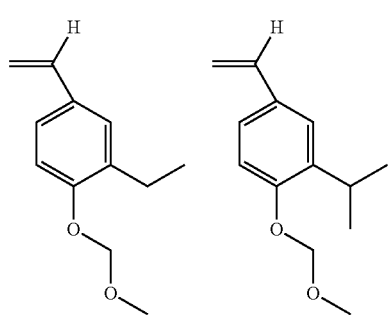

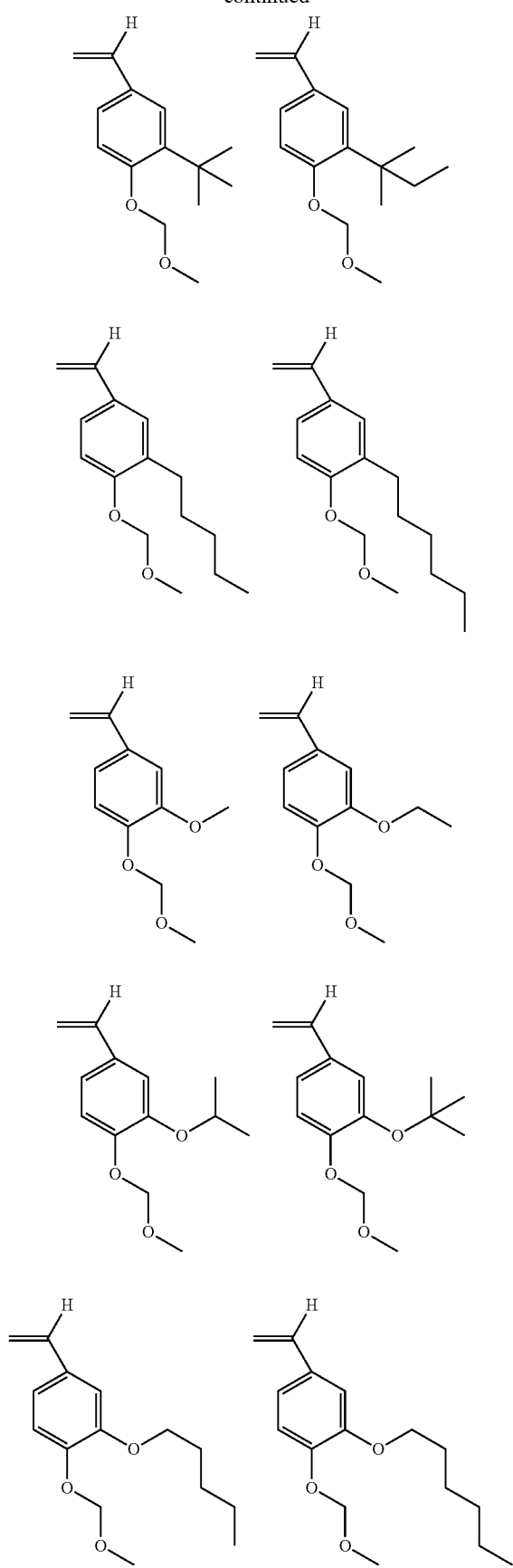

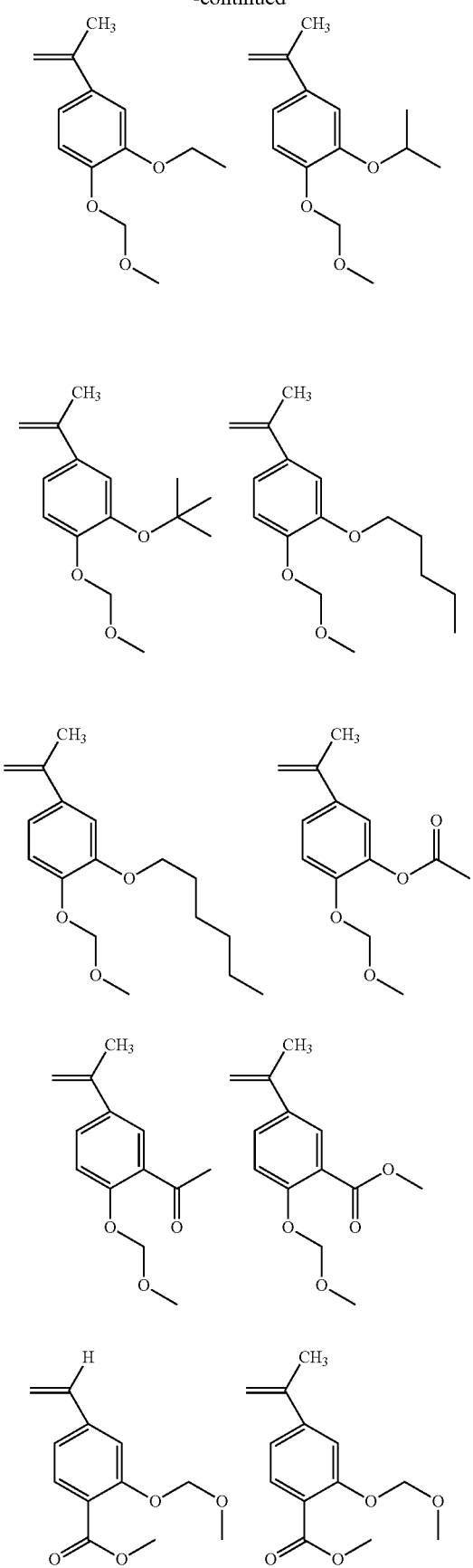

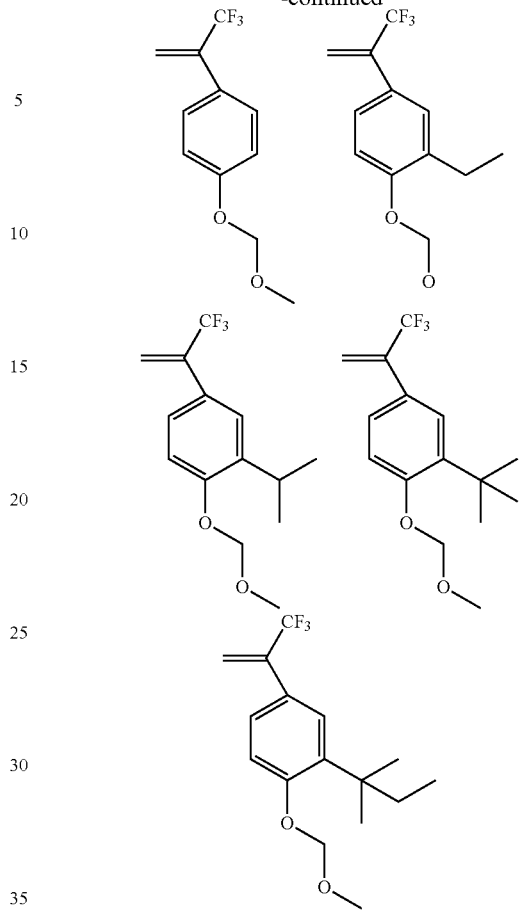

When the resin contains the structural unit derived form the monomer represented by the formula (a1-4), the content of the structural unit derived from the monomer represented by the formula (a1-4) is usually 10 to 95% by mole and preferably 15 to 90% by mole and more preferably 20 to 85% by mole based on total molar of all the structural units of the resin.

Other examples of the compound having an acid-labile group include a monomer represented by the formula (a1-5):

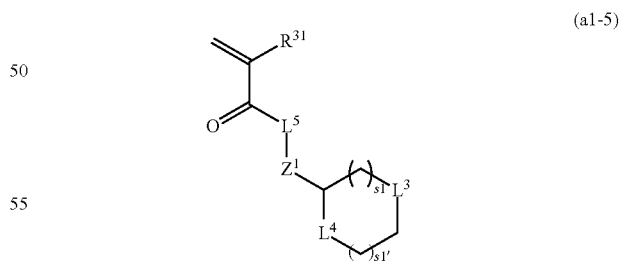

(a1-5)

wherein $R^{31}$ represents a hydrogen atom, a halogen atom, a C1-C4 alkyl group which may be substituted with a halogen atom, $L^5$ represents —O—, —S— or *—O—$(CH_2)_{k1}$—CO—O—, k1 represents an integer of 1 to 7, * represents a binding position to —CO—, $L^3$ and $L^4$ independently each represent —O— or —S—, $Z^1$ represents a single bond or a C1-C6 alkylene group in which one or more —$CH_2$— may be replaced by —O— or —CO—, s1 and s1' independently each represent an integer of 0 to 4.

$R^{31}$ is preferably a hydrogen atom or a methyl group.
$L^5$ is preferably —O—.
It is preferred that one of $L^3$ and $L^4$ is —O— and the other is —S—.
In the formula (a1-5), s1 is preferably 1 and s1' is preferably 0, 1 or 2.
$Z^1$ is preferably a single bond or —$CH_2$—CO—O—.
Examples of the monomer represented by the formula (a1-5) include the following.
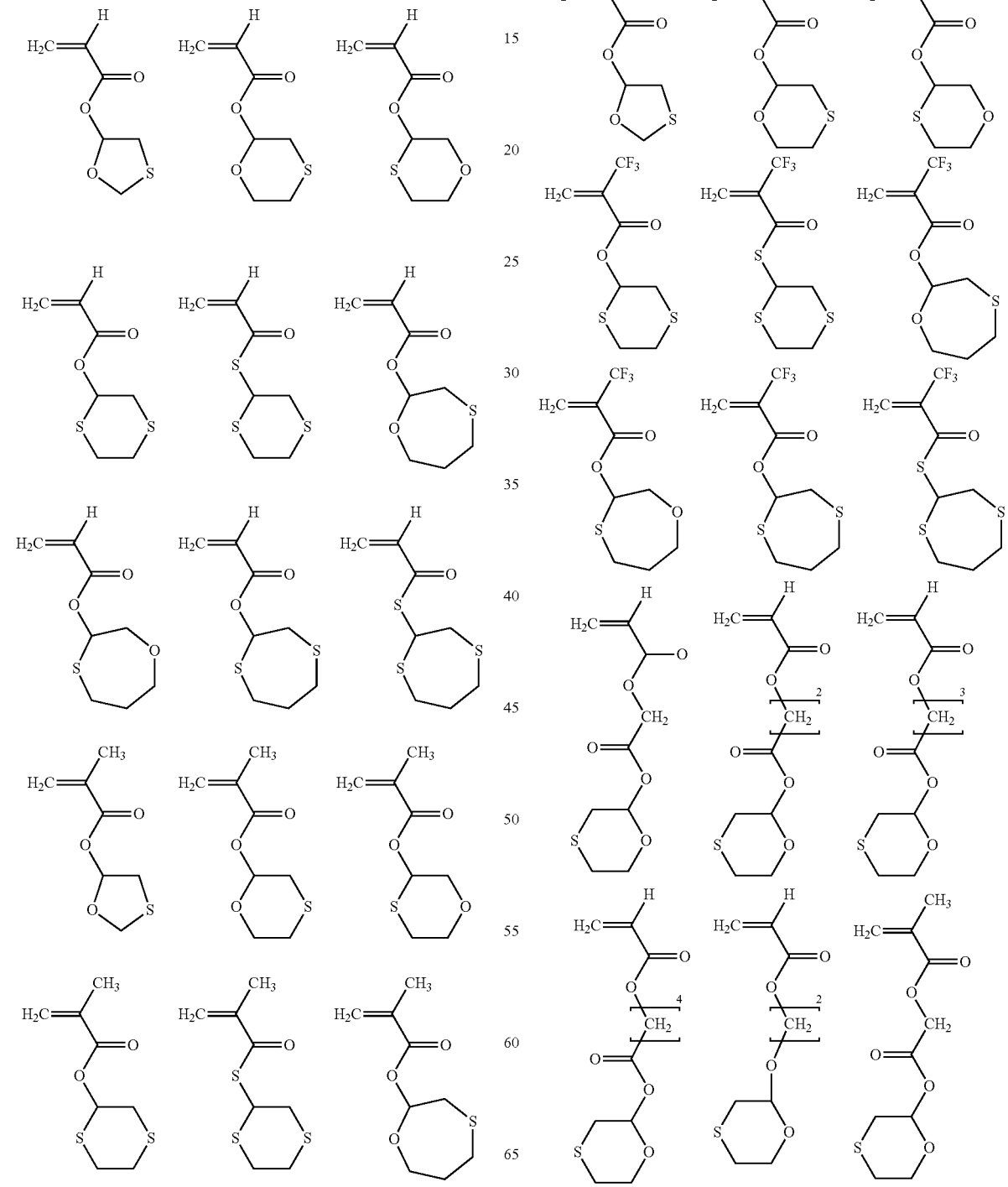

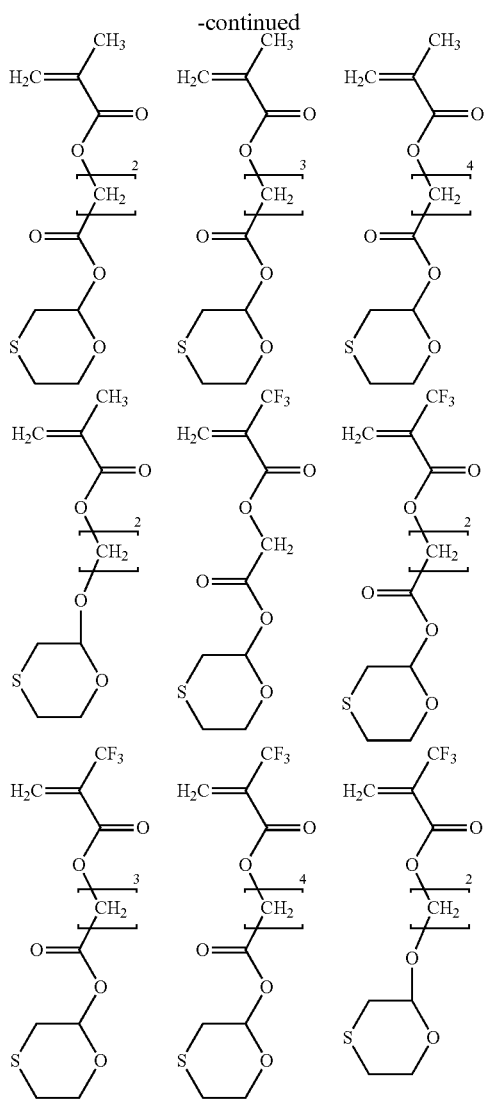

When the resin contains the structural unit derived form the monomer represented by the formula (a1-5), the content of the structural unit derived from the monomer represented by the formula (a1-5) is usually 10 to 95% by mole and preferably 15 to 90% by mole and more preferably 20 to 85% by mole based on total molar of all the structural units of the resin.

The resin can have two or more kinds of structural units derived from the monomers having an acid-labile group.

The resin preferably contains the structural unit derived from the monomer having an acid-labile group and a structural unit derived from the monomer having no acid-labile group. The resin can have two or more kinds of structural units derived from the monomers having no acid-labile group. When the resin contains the structural unit derived from the monomer having an acid-labile group and the structural unit derived from the monomer having no acid-labile group, the content of the structural unit derived from the monomer having an acid-labile group is usually 10 to 80% by mole and preferably 20 to 60% by mole based on total molar of all the structural units of the resin. The content of the structural unit derived from a monomer having an adamantyl group, especially the monomer represented by the formula (a1-1) in the structural unit derived from the compound having no acid-labile group is preferably 15% by mole or more from the viewpoint of dry-etching resistance of the photoresist composition.

The monomer having no acid-labile group preferably contains one or more hydroxyl groups or a lactone ring. When the resin contains the structural unit derived from the monomer having no acid-labile group and having one or more hydroxyl groups or a lactone ring, a photoresist composition having good resolution and adhesiveness of photoresist to a substrate tends to be obtained.

Examples of the monomer having no acid-labile group and having one or more hydroxyl groups include a monomer represented by the formula (a2-0):

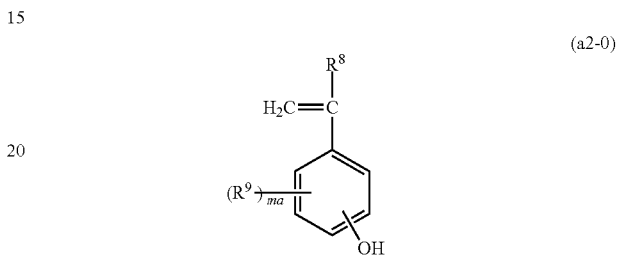

wherein $R^8$ represents a hydrogen atom, a halogen atom, a C1-C6 alkyl group or a C1-C6 halogenated alkyl group, $R^9$ is independently in each occurrence a halogen atom, a hydroxyl group, a C1-C6 alkyl group, a C1-C6 alkoxy group, a C2-C4 acyl group, a C2-C4 acyloxy group, an acryloyl group or a methacryloyl group, ma represents an integer of 0 to 4, and a monomer represented by the formula (a2-1):

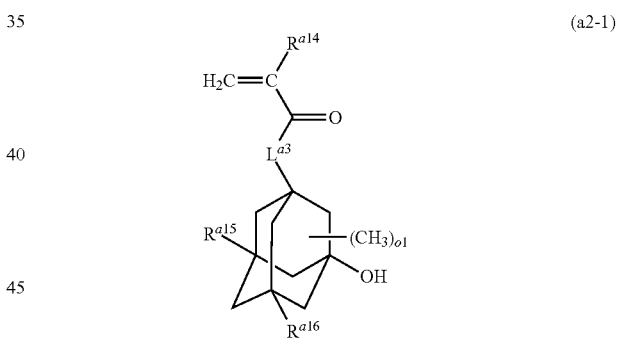

wherein $R^{a14}$ represents a hydrogen atom or a methyl group, $R^{a15}$ and $R^{a16}$ each independently represent a hydrogen atom, a methyl group or a hydroxyl group, $L^{a3}$ represents *—O— or *—O—$(CH_2)_{k2}$—CO—O— in which * represents a binding position to —CO—, and k2 represents an integer of 1 to 7, and of represents an integer of 0 to 10.

When KrF excimer laser (wavelength: 248 nm) lithography system, or a high energy laser such as electron beam and extreme ultraviolet is used as an exposure system, the resin containing the structural unit derived from the monomer represented by the formula (a2-0) is preferable, and when ArF excimer laser (wavelength: 193 nm) is used as an exposure system, the resin containing the structural unit derived from the monomer represented by the formula (a2-1) is preferable.

In the formula (a2-0), examples of the halogen atom include a fluorine atom, examples of the C1-C6 alkyl group include a methyl group, an ethyl group, a propyl group, an isopropyl group, a butyl group, an isobutyl group, a sec-butyl group, a tert-butyl group, a pentyl group and a hexyl group, and a C1-C4 alkyl group is preferable and a C1-C2 alkyl group is more preferable and a methyl group is especially preferable. Examples of the C1-C6 halogenated alkyl group include a trifluoromethyl group, a pentafluoroethyl group, a heptafluoropropyl group, a heptafluoroisopropyl group, a nonafluorobutyl group, a nonafluoro-sec-butyl group, a non-afluoro-tert-butyl group, a perfluoropentyl group and a perfluorohexyl group. Examples of the C1-C6 alkoxy group include a methoxy group, an ethoxy group, a propoxy group, an isopropoxy group, a butoxy group, an isobutoxy group, a sec-butoxy group, a tert-butoxy group, a pentyloxy group and a hexyloxy group, and a C1-C4 alkoxy group is preferable and a C1-C2 alkoxy group is more preferable and a methoxy group is especially preferable. Examples of the C2-C4 acyl group include an acetyl group, a propionyl group and a butyryl group, and examples of the C2-C4 acyloxy group include an acetyloxy group, a propionyloxy group and a butyryloxy group. In the formula (a2-0), ma is preferably 0, 1 or 2, and is more preferably 0 or 1, and especially preferably 0.

The resin containing the structural unit derived from the monomer represented by the formula (a2-0) can be produced, for example, by polymerizing a monomer obtained by protecting a hydroxyl group of the monomer represented by the formula (a2-0) with a protecting group such as an acetyl group followed by conducting deprotection of the obtained polymer with an acid or a base.

Examples of the monomer represented by the formula (a2-0) include the monomers described in JP 2010-204646 A, and 4-hydroxystyrene and 4-hydroxy-α-methylstyrene are preferable.

When the resin contains the structural unit derived from the monomer represented by the formula (a2-0), the content of the structural unit derived from the monomer represented by the formula (a2-0) is usually 5 to 95% by mole and preferably 10 to 80% by mole and more preferably 15 to 80% by mole based on total molar of all the structural units of the resin.

In the formula (a2-1), $R^{a14}$ is preferably a methyl group, $R^{a15}$ is preferably a hydrogen atom, $R^{a16}$ is preferably a hydrogen atom or a hydroxyl group, $L^{a3}$ is preferably *—O— or *—O—$(CH_2)_{f2}$—CO—O— in which * represents a binding position to —CO—, and f2 represents an integer of 1 to 4, and is more preferably *—O—, and o1 is preferably 0, 1, 2 or 3 and is more preferably 0 or 1.

Examples of the monomer represented by the formula (a2-1) include the monomers described in JP 2010-204646 A, and the monomers represented by the formulae (a2-1-1) to (a2-1-6) are preferable, and the monomers represented by the formulae (a2-1-1) to (a2-1-4) are more preferable, and the monomers represented by the formulae (a2-1-1) and (a2-1-3) are still more preferable,

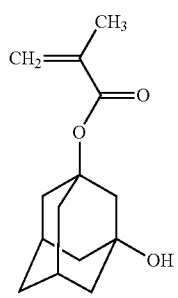

(a2-1-1)

-continued

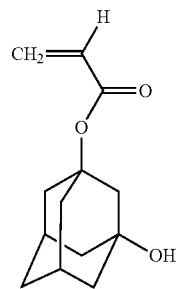

(a2-1-2)

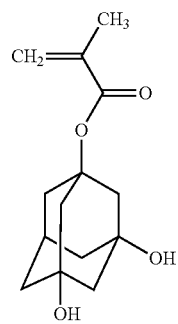

(a2-1-3)

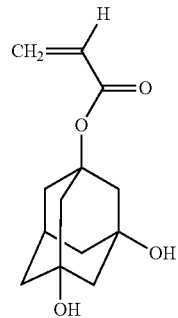

(a2-1-4)

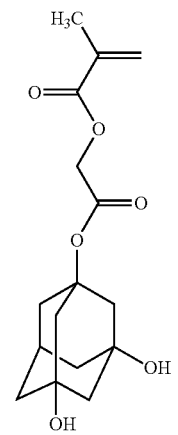

(a2-1-5)

(a2-1-6)

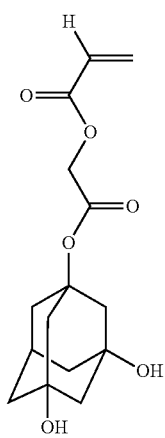

When the resin contains the structural unit derived from the monomer represented by the formula (a2-1), the content of the structural unit derived from the monomer represented by the formula (a2-1) is usually 3 to 45% by mole based on total molar of all the structural units of the resin, and preferably 5 to 40% by mole, and more preferably 5 to 35% by mole, and especially preferably 5 to 20% by mole.

Examples of the lactone ring of the monomer having no acid-labile group and a lactone ring include a monocyclic lactone ring such as β-propiolactone ring, γ-butyrolactone ring and γ-valerolactone ring, and a condensed ring formed from a monocyclic lactone ring and the other ring. Among them, preferred are γ-butyrolactone ring and a condensed lactone ring formed from γ-butyrolactone ring and the other ring.

Preferable examples of the monomer having no acid-labile group and a lactone ring include the monomers represented by the formulae (a3-1), (a3-2) and (a3-3):

(a3-1)

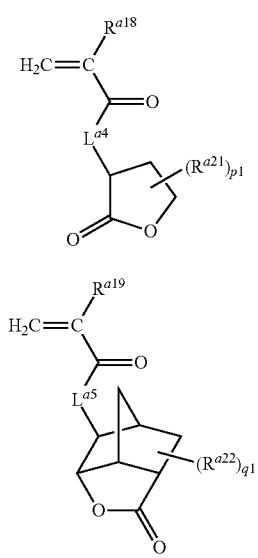

(a3-2)

(a3-3)

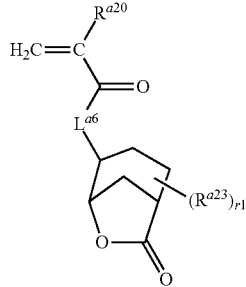

wherein $L^{a4}$, $L^{a5}$ and $L^{a6}$ each independently represent *—O— or *—O—$(CH_2)_{k3}$—CO—O— in which * represents a binding position to —CO— and k3 represents an integer of 1 to 7, $R^{a18}$, $R^{a19}$ and $R^{a20}$ each independently represent a hydrogen atom or a methyl group, $R^{a21}$ represents a C1-C4 aliphatic hydrocarbon group, $R^{a22}$ and $R^{a23}$ are independently in each occurrence a carboxyl group, a cyano group or a C1-C4 aliphatic hydrocarbon group, and p1 represents an integer of 0 to 5, q1 and r1 independently each represent an integer of 0 to 3.

It is preferred that $L^{a4}$, $L^{a5}$ and $L^{a6}$ each independently represent *—O— or *—O—$(CH_2)_{d1}$—CO—O— in which * represents a binding position to —CO— and d1 represents an integer of 1 to 4, and it is more preferred that $L^{a4}$, $L^{a5}$ and $L^{a6}$ are *—O—. $R^{a18}$, $R^{a19}$ and $R^{a20}$ are preferably methyl groups. $R^{a21}$ is preferably a methyl group. It is preferred that $R^{a22}$ and $R^{a23}$ are independently in each occurrence a carboxyl group, a cyano group or a methyl group. It is preferred that p1 is an integer of 0 to 2, and it is more preferred that p1 is 0 or 1. It is preferred that q1 and r1 independently each represent an integer of 0 to 2, and it is more preferred that q1 and r1 independently each represent 0 or 1.

Examples of the monomer represented by the formula (a3-1) include the monomers described in JP 2010-204646 A, and the monomers represented by the formulae (a3-1-1) to (a3-1-4), (a3-2-1) to (a3-2-4) and (a3-3-1) to (a3-3-4) are preferable, and the monomers represented by the formulae (a3-1-1) to (a3-1-2) and (a3-2-3) to (a3-2-4) are more preferable, and the monomers represented by the formulae (a3-1-1) and (a3-2-3) are still more preferable.

(a3-1-1)

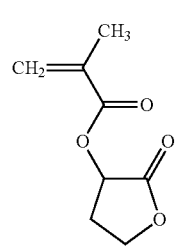

(a3-1-2)

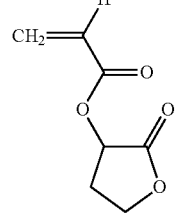

-continued
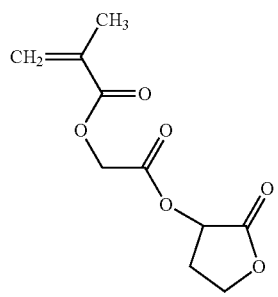 (a3-1-3)
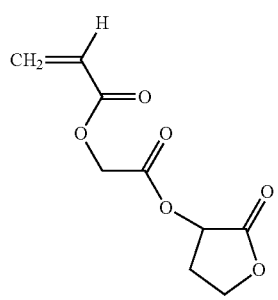 (a3-1-4)
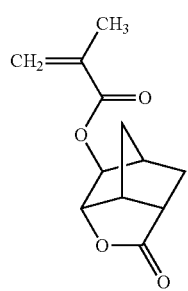 (a3-2-1)
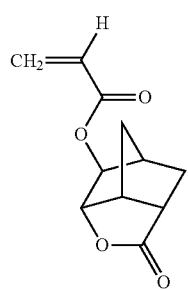 (a3-2-2)
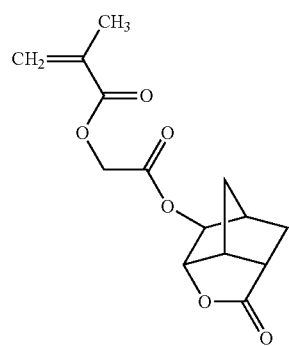 (a3-2-3)
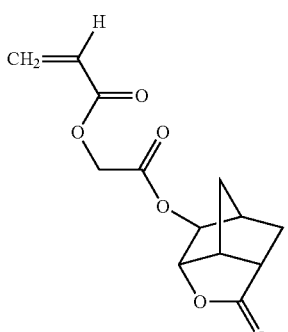 (a3-2-4)
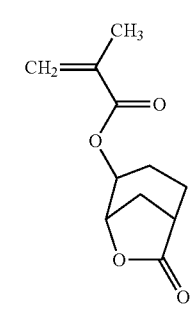 (a3-3-1)
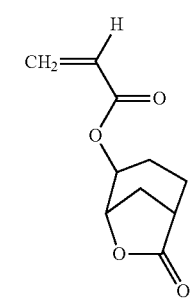 (a3-3-2)
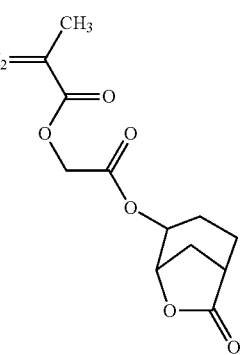 (a3-3-3)

-continued (a3-3-4)

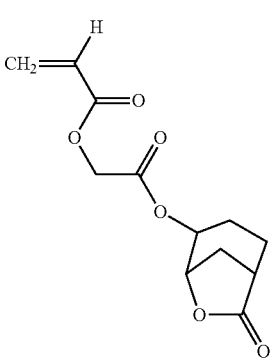

When the resin contains the structural unit derived from the monomer having no acid-labile group and having a lactone ring, the content thereof is usually 5 to 70% by mole based on total molar of all the structural units of the resin, and preferably 10 to 65% by mole and more preferably 10 to 60% by mole.

Examples of the other monomer having no acid-labile group include the monomers represented by the formulae (a-4-1), (a-4-2) and (a-4-3):

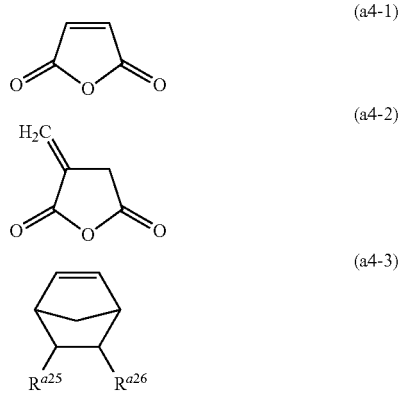

wherein $R^{a25}$ and $R^{a26}$ each independently represents a hydrogen atom, a C1-C3 aliphatic hydrocarbon group which can have one or more hydroxyl groups, a carboxyl group, a cyano group or a —COOR$^{a27}$ group in which R$^{a27}$ represents a C1-C18 aliphatic hydrocarbon group or a C3-C18 alicyclic hydrocarbon group, and one or more —CH$_2$— in the C1-C18 aliphatic hydrocarbon group and the C3-C18 alicyclic hydrocarbon group can be replaced by —O— or —CO—, with the proviso that the carbon atom bonded to —O— of —COO— of R$^{a27}$ is not a tertiary carbon atom, or R$^{a25}$ and R$^{a26}$ are bonded together to form a carboxylic anhydride residue represented by —C(=O)—O—C(=O)—.

Examples of the substituent of the C1-C3 aliphatic hydrocarbon group include a hydroxyl group. Examples of the C1-C3 aliphatic hydrocarbon group which can have one or more hydroxyl groups include a C1-C3 alkyl group such as a methyl group, an ethyl group and a propyl group, and a C1-C3 hydroxyalkyl group such a hydroxymethyl group and a 2-hydroxyethyl group. The C1-C18 aliphatic hydrocarbon group represented by R$^{a27}$ is preferably a C1-C8 aliphatic hydrocarbon group and is more preferably a C1-C6 aliphatic hydrocarbon group. The C3-C18 alicyclic hydrocarbon group represented by R$^{a27}$ is preferably a C4-C18 alicyclic hydrocarbon group, and is more preferably C4-C12 alicyclic hydrocarbon group. Examples of R$^{a27}$ include a methyl group, an ethyl group, a propyl group, a 2-oxo-oxolan-3-yl group and a 2-oxo-oxolan-4-yl group.

Examples of the monomer represented by the formula (a-4-3) include 2-norbornene, 2-hydroxy-5-norbornene, 5-norbornene-2-carboxylic acid, methyl 5-norbornene-2-carboxylate, 2-hydroxyethyl 5-norbornene-2-carboxylate, 5-norbornene-2-methanol and 5-norbornene-2,3-dicarboxylic anhydride.

When the resin contains a structural unit derived from a monomer represented by the formula (a-4-1), (a-4-2) or (a-4-3), the content thereof is usually 2 to 40% by mole and preferably 3 to 30% by mole and more preferably 5 to 20% by mole based on total molar of all the structural units of the resin.

Examples of the other monomer having no acid-labile group include a monomer represented by the formula (a-4-4):

(a4-4)

$$H_2C=C\begin{array}{c}R^{a28}\\|\\C=O\\|\\L^{a7}\\ \backslash\\W^{16}\end{array}$$

wherein $R^{a28}$ represents a hydrogen atom or a methyl group, $L^{a7}$ represents —O— or *—O—(CH$_2$)$_{k2}$—CO—O— in which * represents a binding position to —CO— and k2 represents an integer of 1 to 7, and $W^{16}$ represents a group containing a sultone ring which may have one or more substituents.

Examples of the sultone ring include the following.

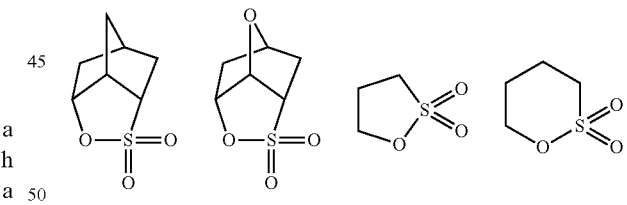

Examples of the group containing a sultone ring include groups formed by removing any one hydrogen atom from the above-mentioned sultone ring. Examples of the substituents include a hydroxyl group, a cyano group, a C1-C6 alkyl group, a C1-C6 fluorinated alkyl group, a C1-C6 hydroxyalkyl group, a C1-C6 alkoxy group, a C2-C7 alkoxycarbonyl group, a C2-C8 acyl group and a C2-C7 acyloxy group.

Examples of the fluorinated alkyl group include a difluoromethyl group, a trifluoromethyl group, a 1,1-difluoroethyl group, a 2,2-difluoroethyl group, a 2,2,2-trifluoroethyl group, a perfluoroethyl group, a 1,1,2,2-tetrafluoropropyl group, a 1,1,2,2,3,3-hexafluoropropyl group, a (perfluoroethyl)methyl group, a 1-(trifluoromethyl)-1,2,2,2-tetrafluoroethyl group, a perfluoropropyl group, a 1,1,2,2-tetrafluorobutyl group, a 1,1,2,2,3,3-hexafluorobutyl group, a 1,1,2,2,3,3,4,4-octafluorobutyl group, a perfluorobutyl group, a 1,1-bis(trifluoromethyl)-2,2,2-trifluoroethyl group, 2-(perfluoropropyl)ethyl group, a 1,1,2,2,3,3,4,4-octafluoropentyl group, a perfluoropentyl group, a 1,1,2,2,3,3,4,4,5,5-decafluoropentyl group, a 1,1-bis(trifluoromethyl)-2,2,3,3,3,-pentafluoropropyl group, a perfluoropentyl group, a 2-(perfluorobutyl)ethyl group, a 1,1,2,2,3,3,4,4,5,5-decafluorohexyl group, a 1,1,2,2,3,3,4,4,5,5,6,6-dodecafluorohexyl group, a (perfluoropentyl)methyl group and a perfluorohexyl group. Among them preferred is a C1-C4 fluorinated alkyl group, and more preferred are a trifluoromethyl group, a perfluoroethyl group and a perfluoropropyl group, and especially preferred is a trifluoromethyl group.

Examples of the hydroxyalkyl group include a hydroxymethyl group and a 2-hydroxyethyl group.

Examples of the monomer represented by the formula (a-4-4) include the following.

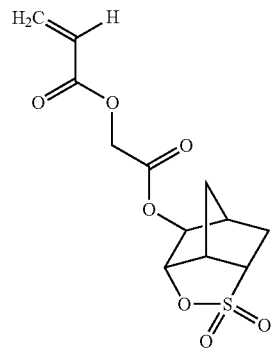
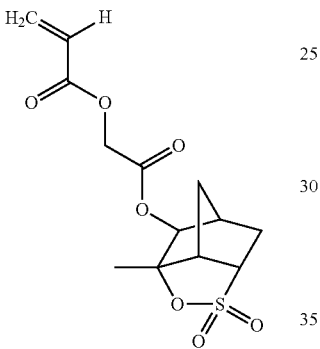

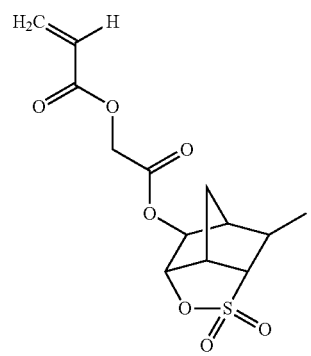
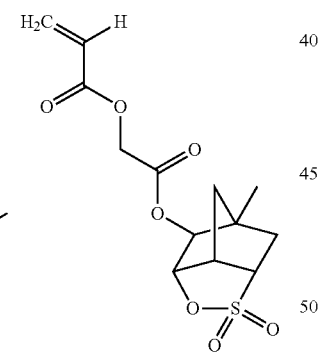

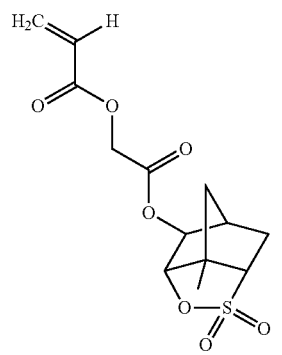
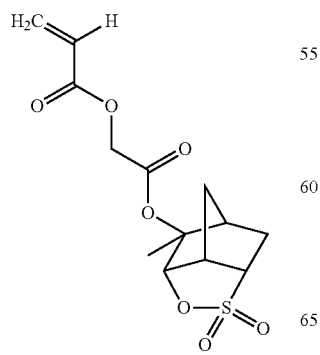

-continued

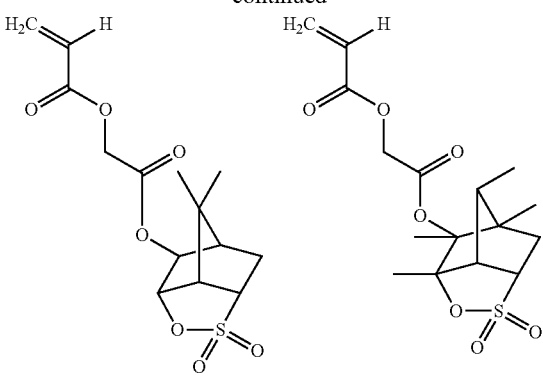

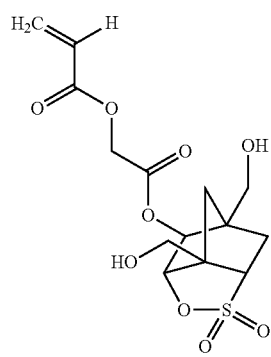

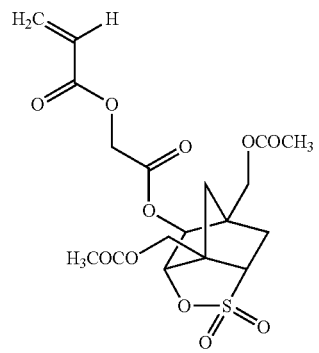

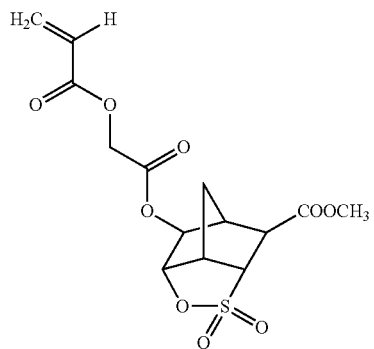

97
-continued
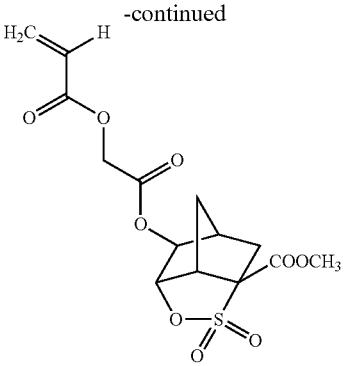
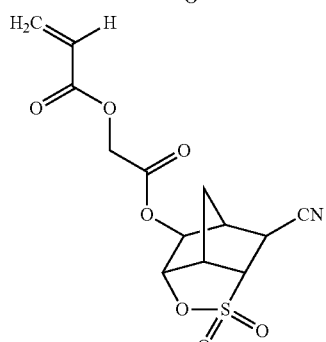
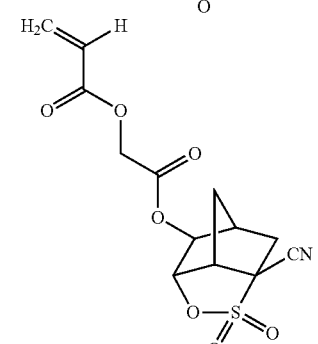
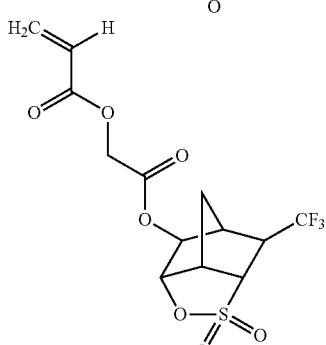
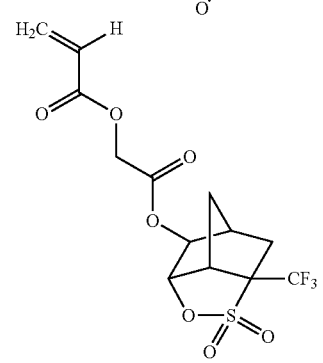
98
-continued
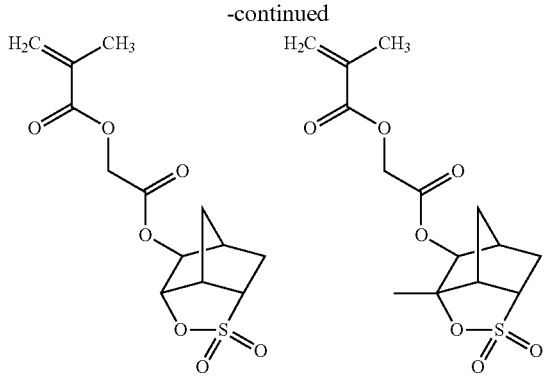
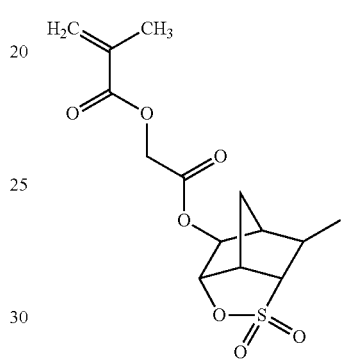
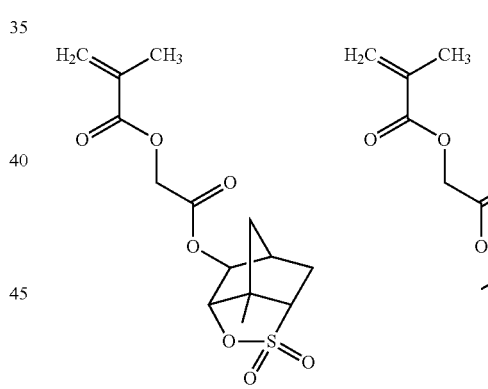
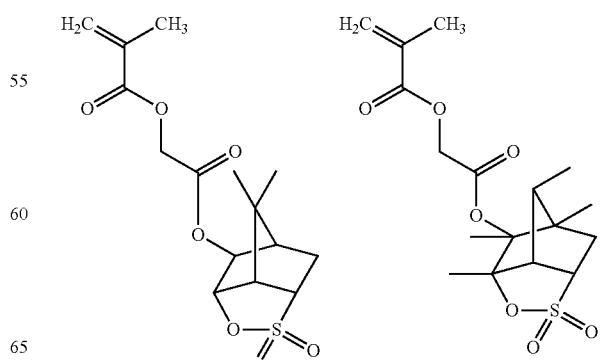

99
-continued
100
-continued
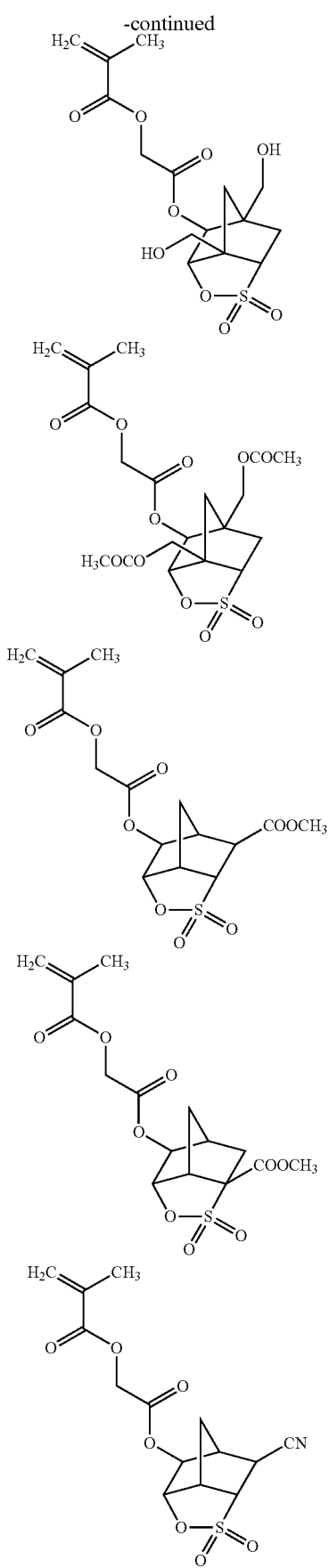
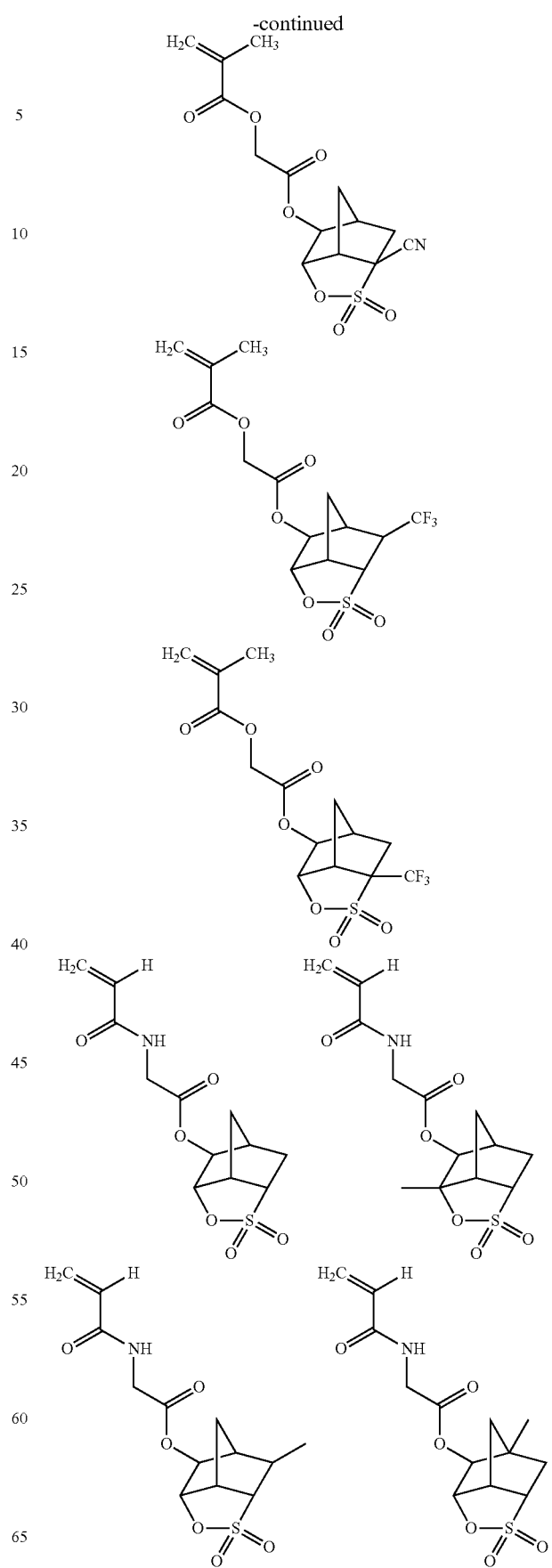

101
-continued
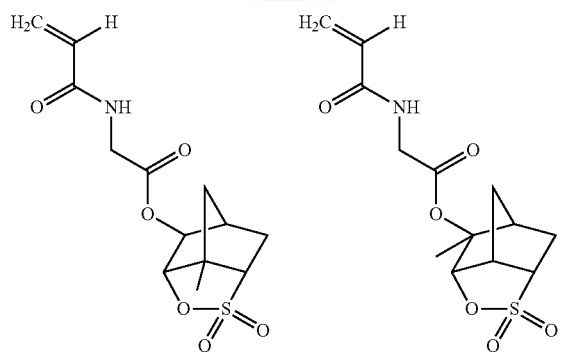
102
-continued
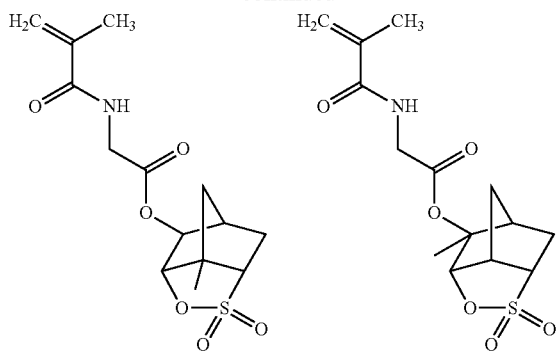

103
-continued
104
-continued
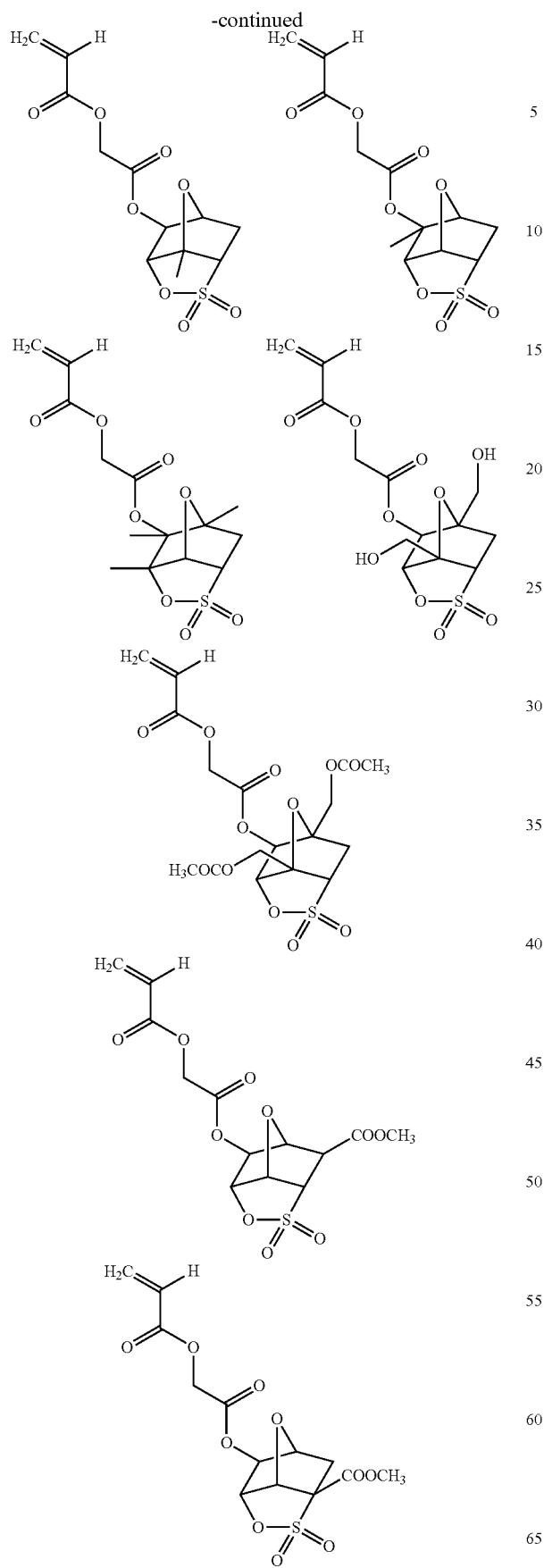
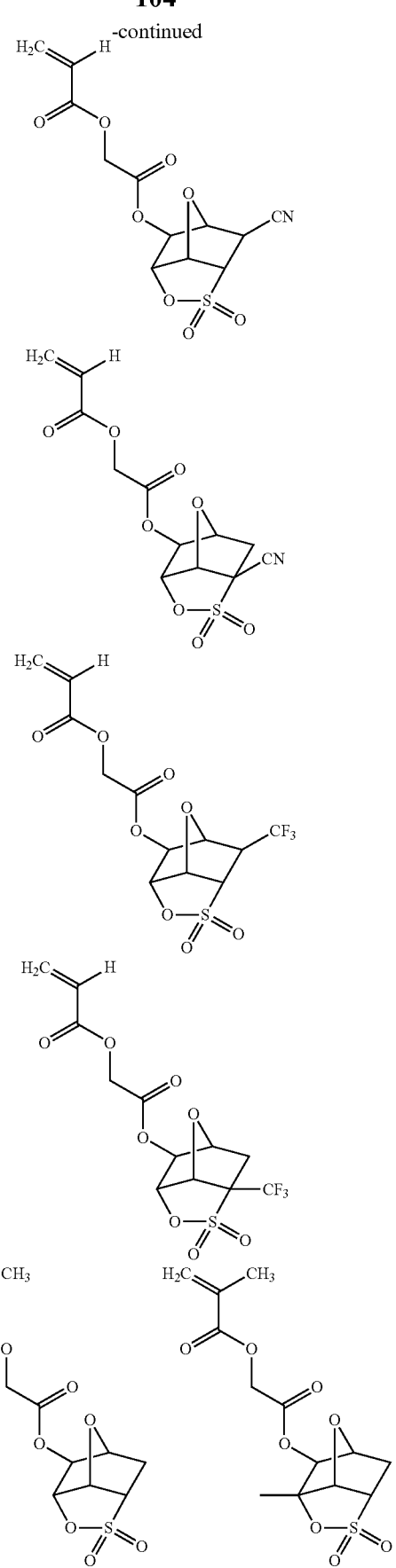

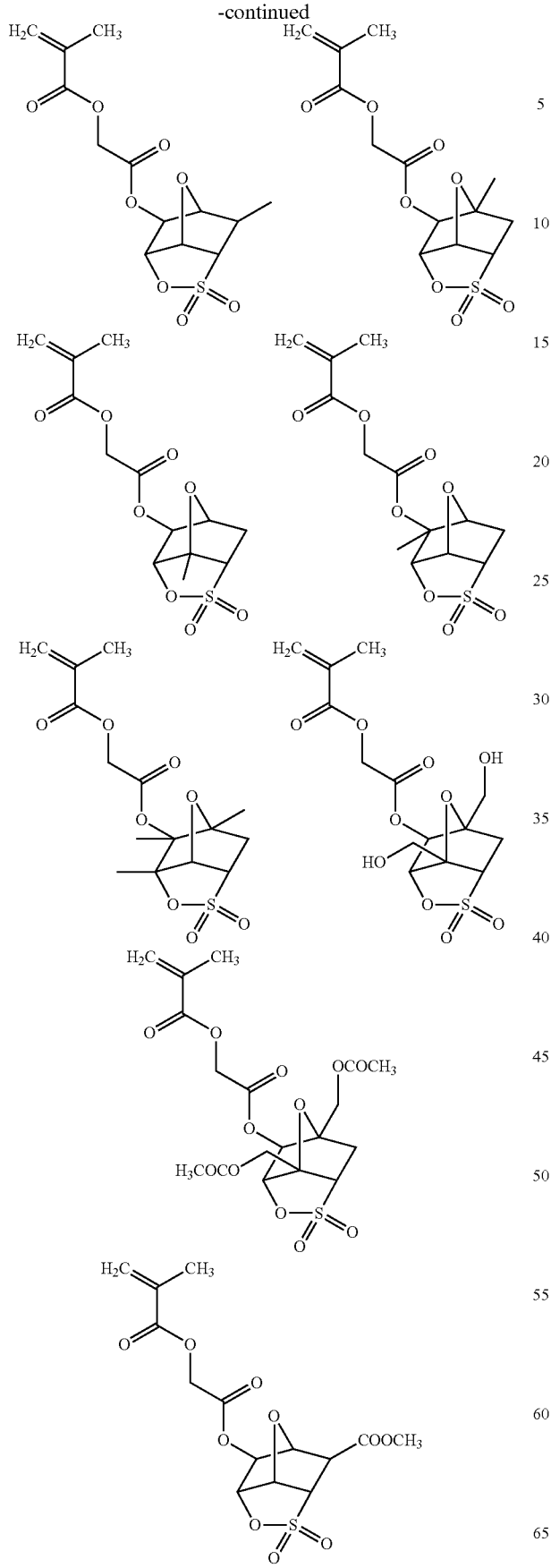
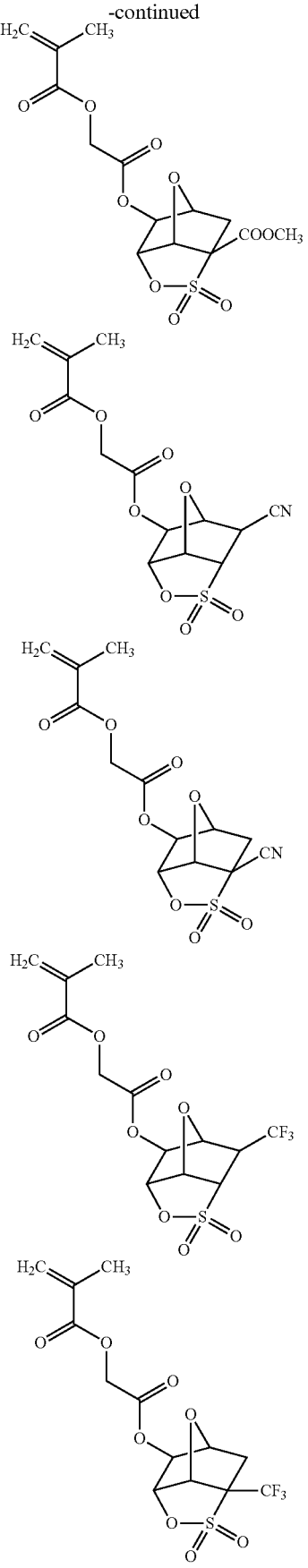

107
-continued
108
-continued
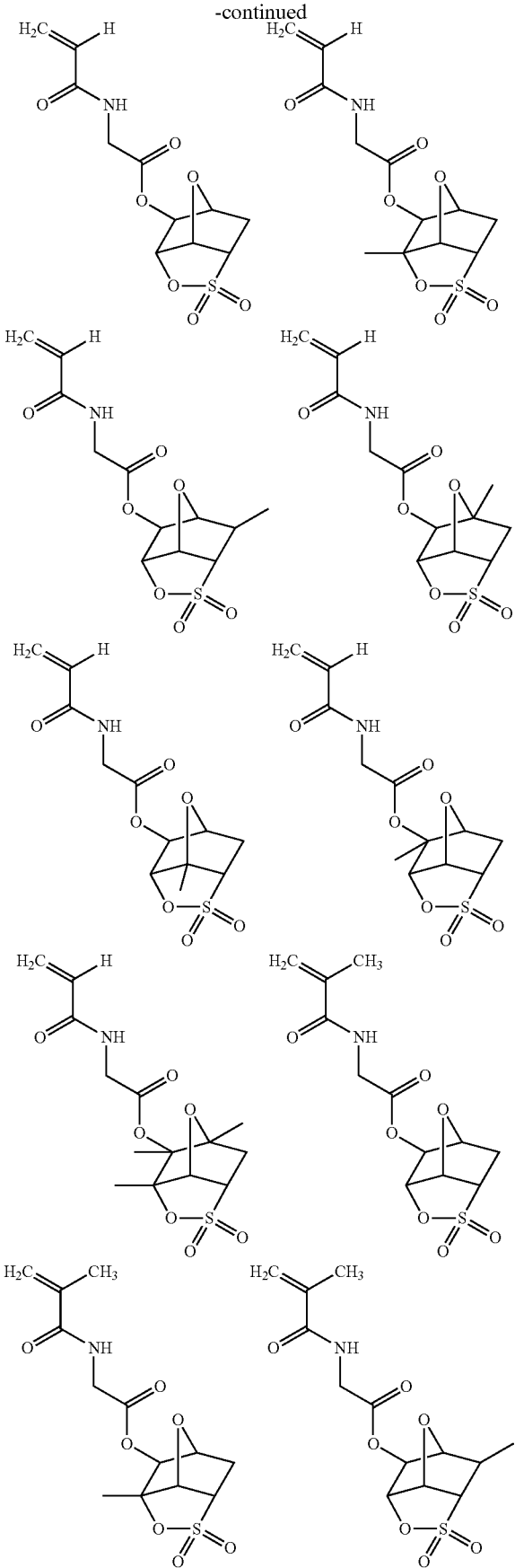
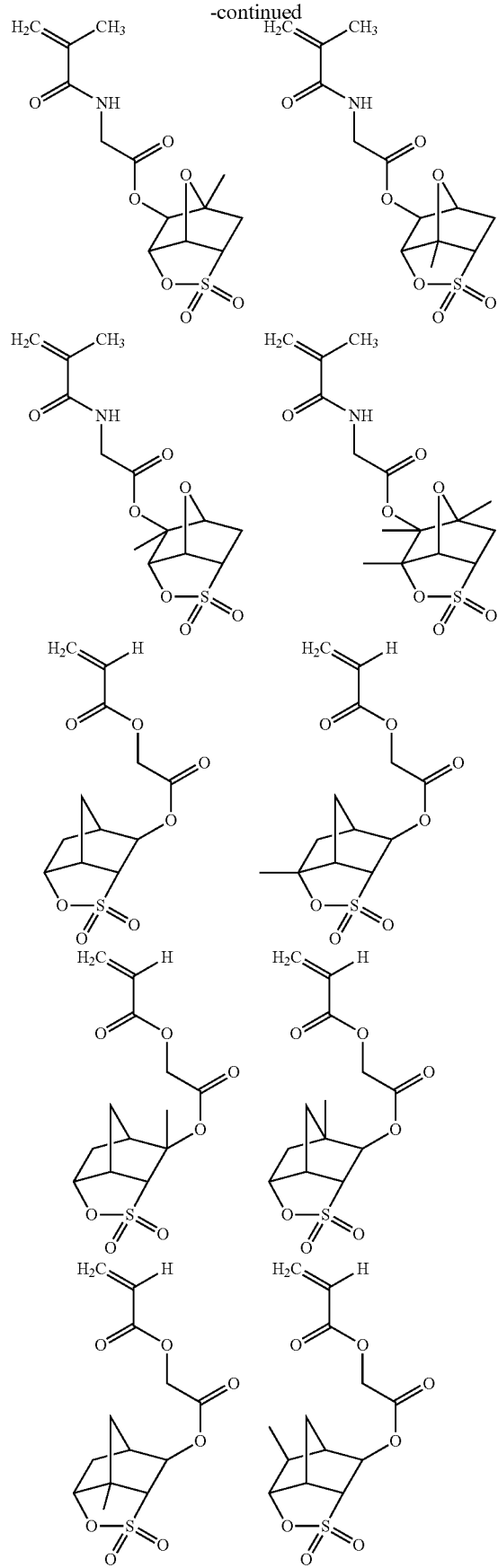

109
-continued
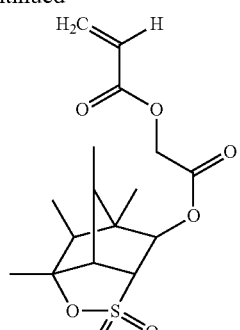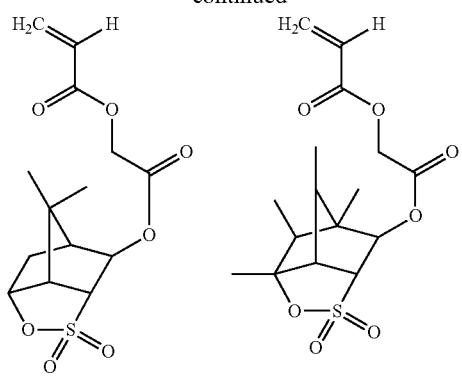
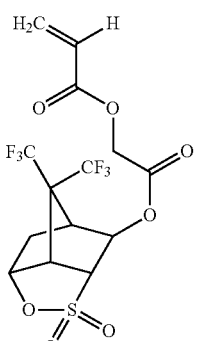
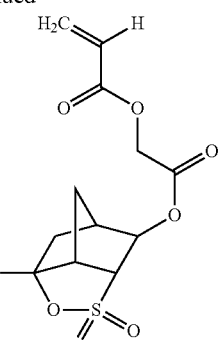
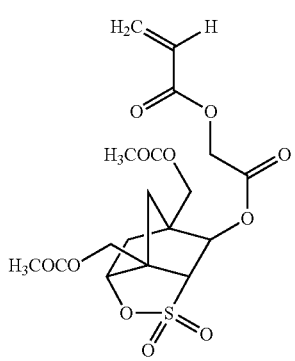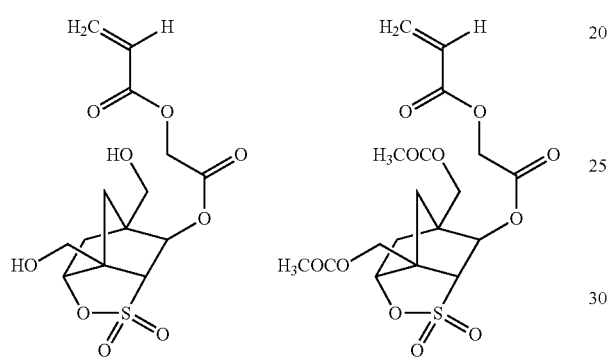
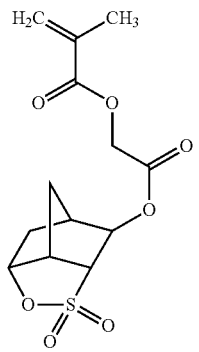
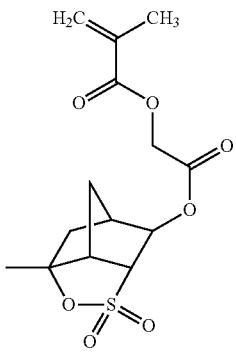
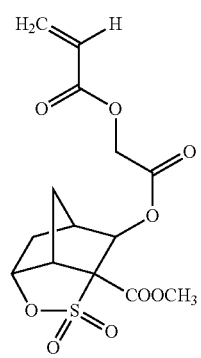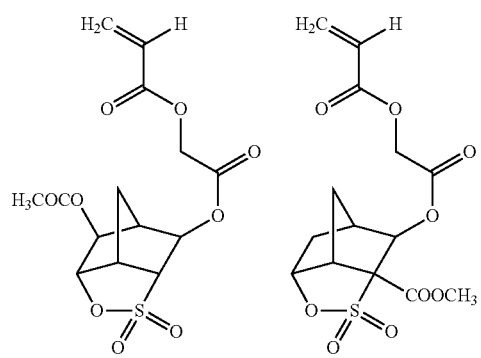
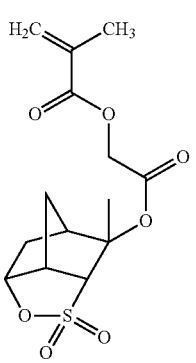
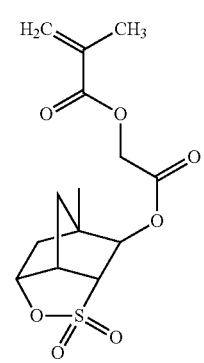
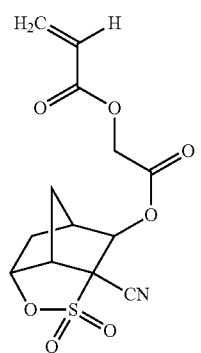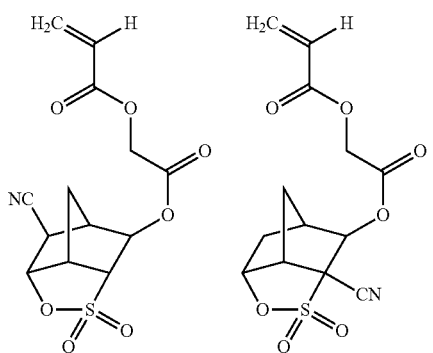
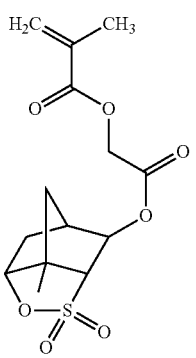
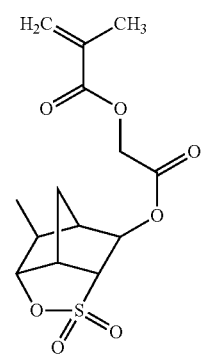
110
-continued 111
-continued
112
-continued
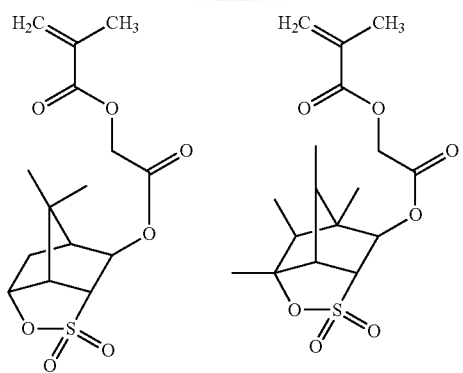
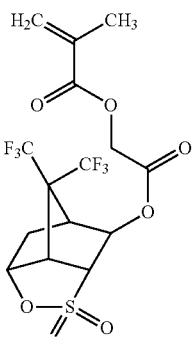
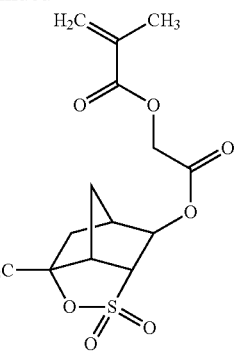
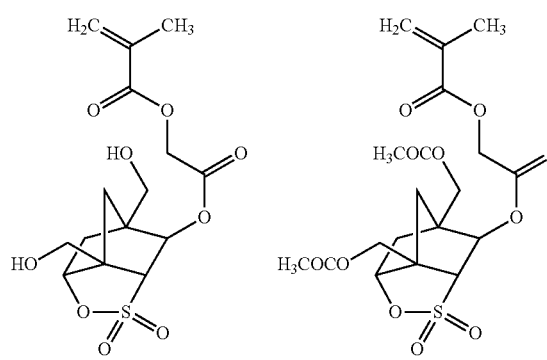
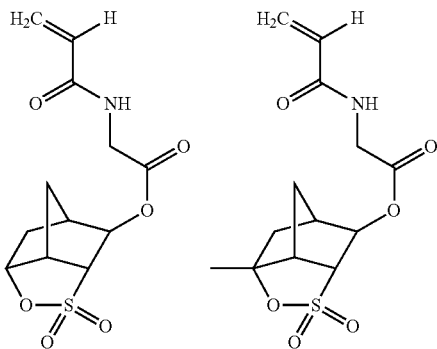
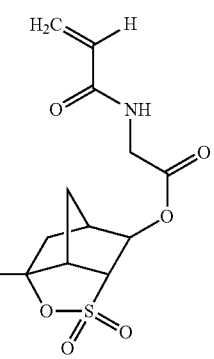
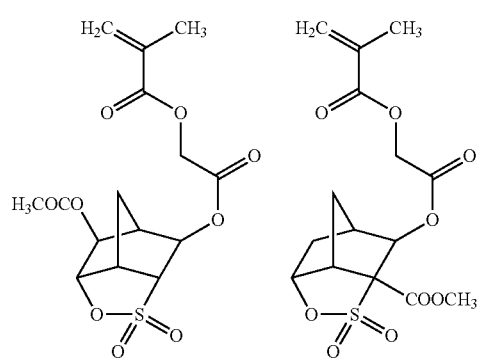
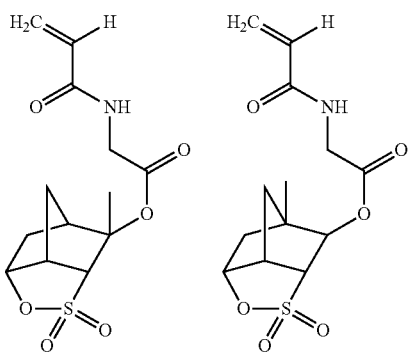
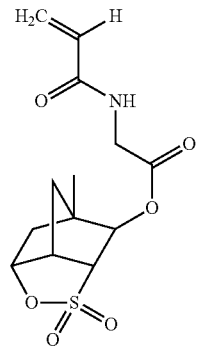
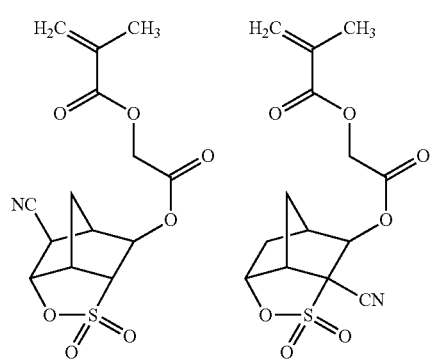
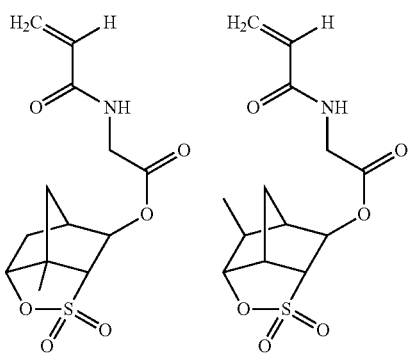
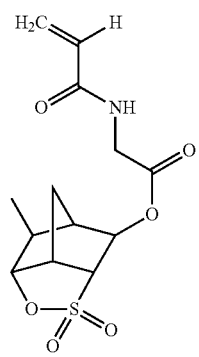

113
-continued
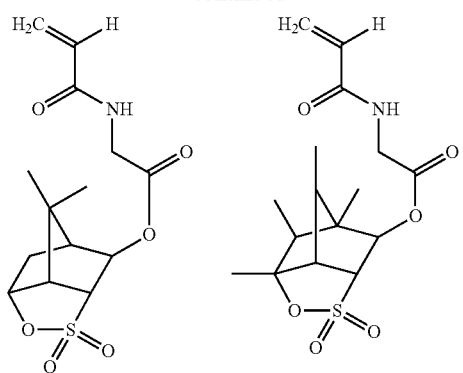
114
-continued
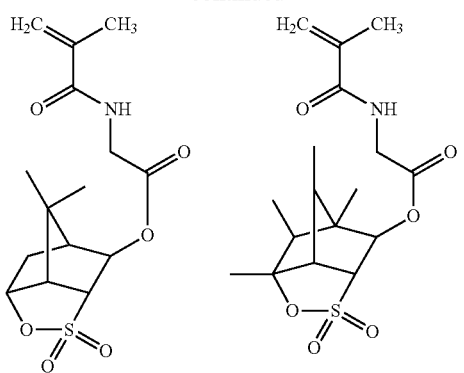
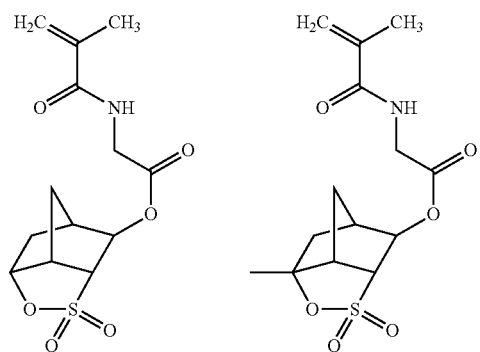
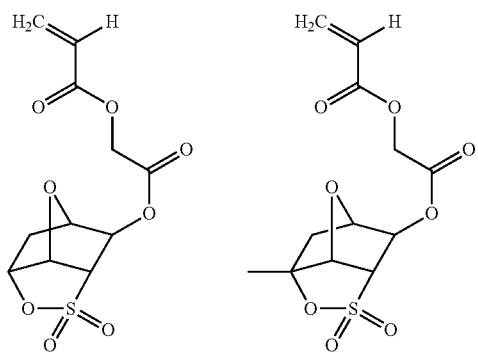
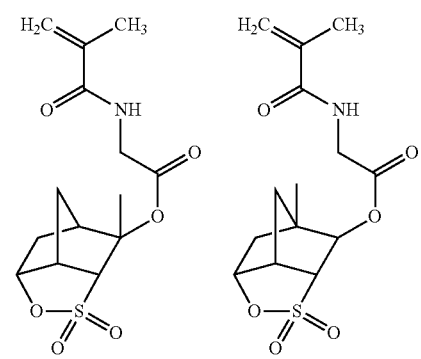
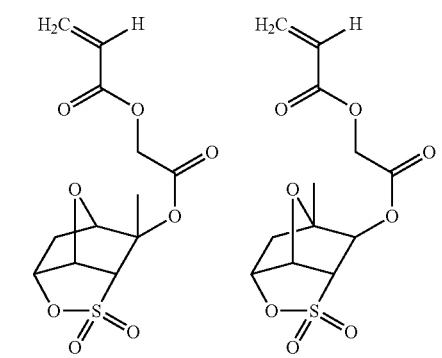
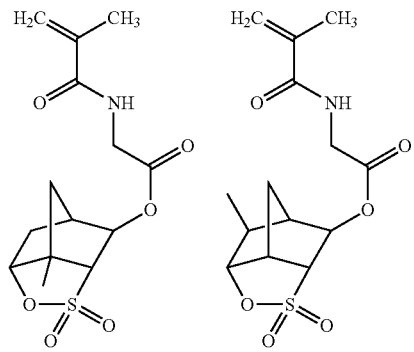
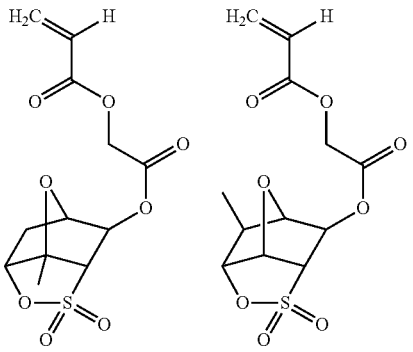

-continued
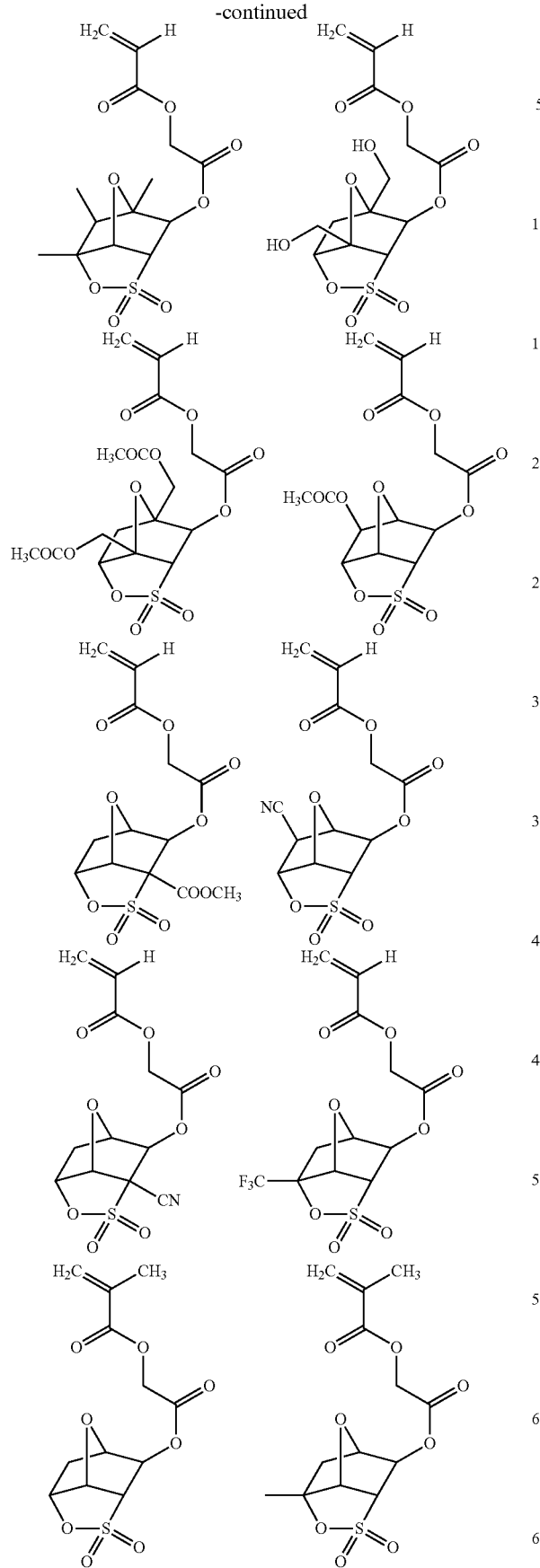
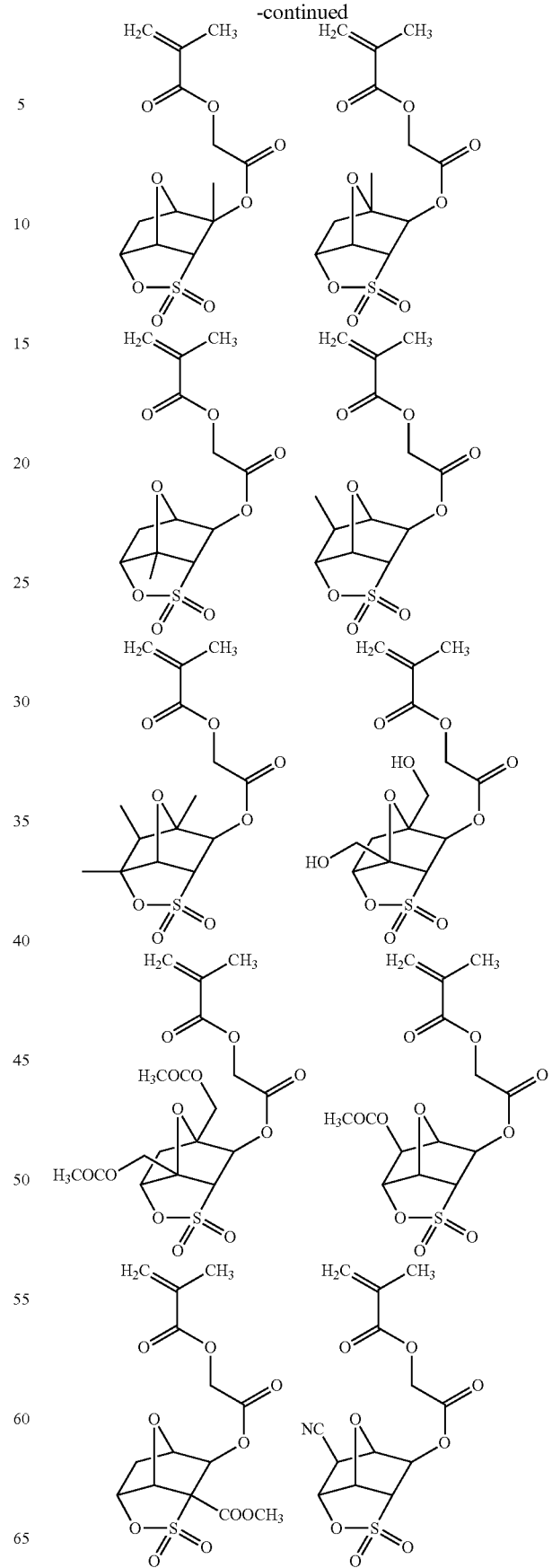

117
-continued

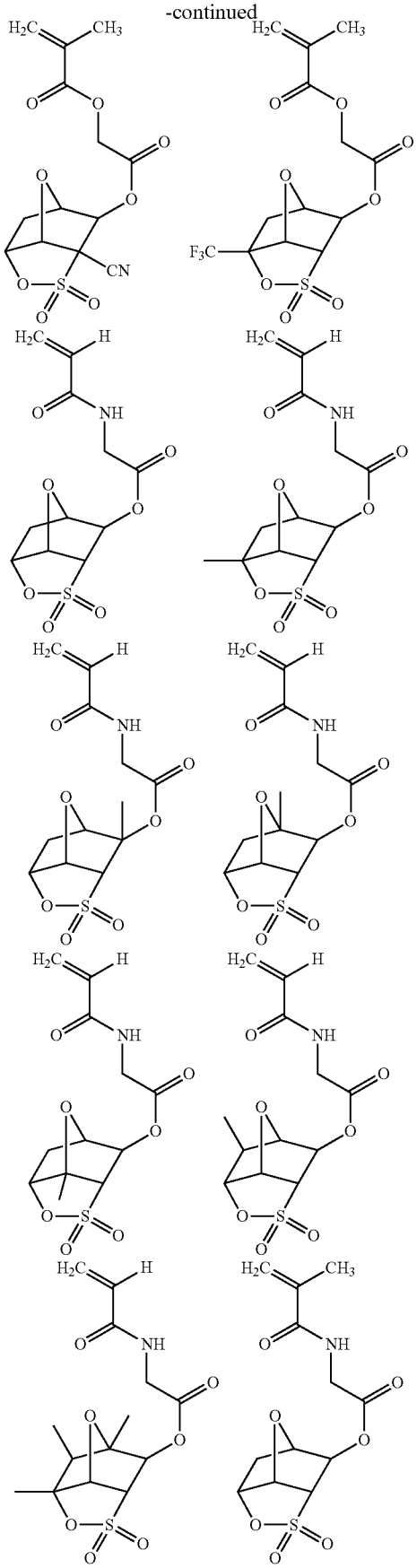

118
-continued

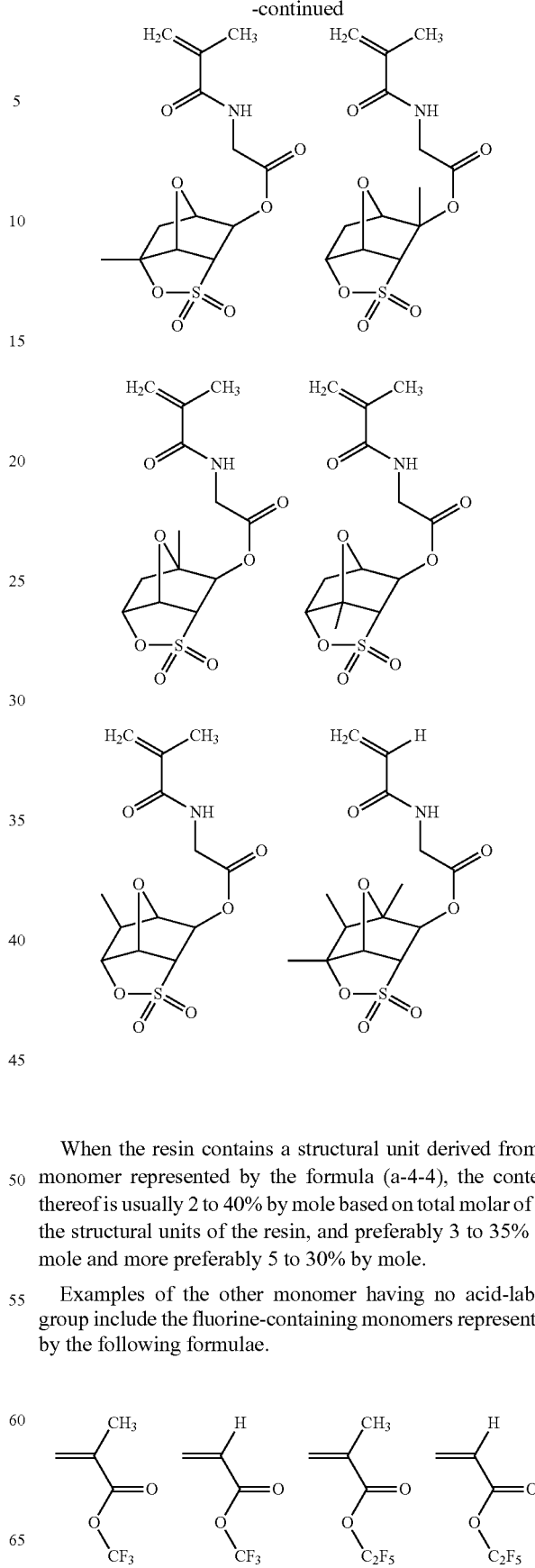

When the resin contains a structural unit derived from a monomer represented by the formula (a-4-4), the content thereof is usually 2 to 40% by mole based on total molar of all the structural units of the resin, and preferably 3 to 35% by mole and more preferably 5 to 30% by mole.

Examples of the other monomer having no acid-labile group include the fluorine-containing monomers represented by the following formulae.

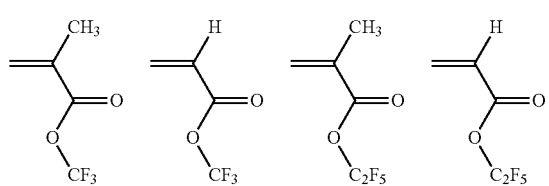

119
-continued
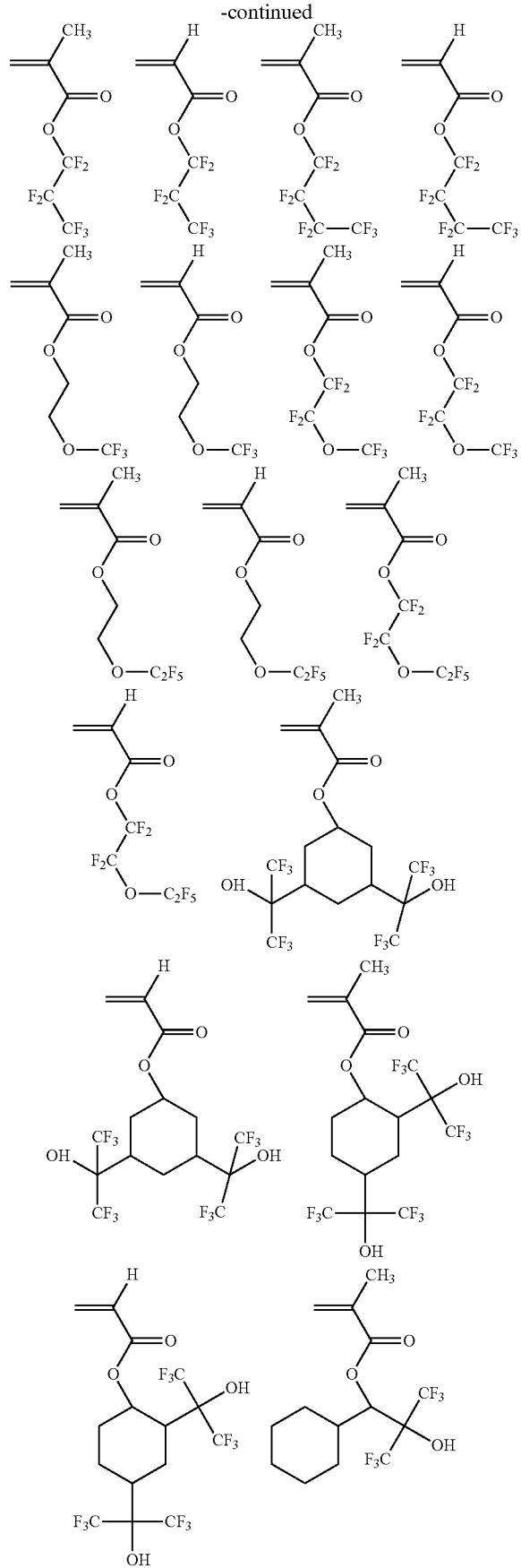
120
-continued
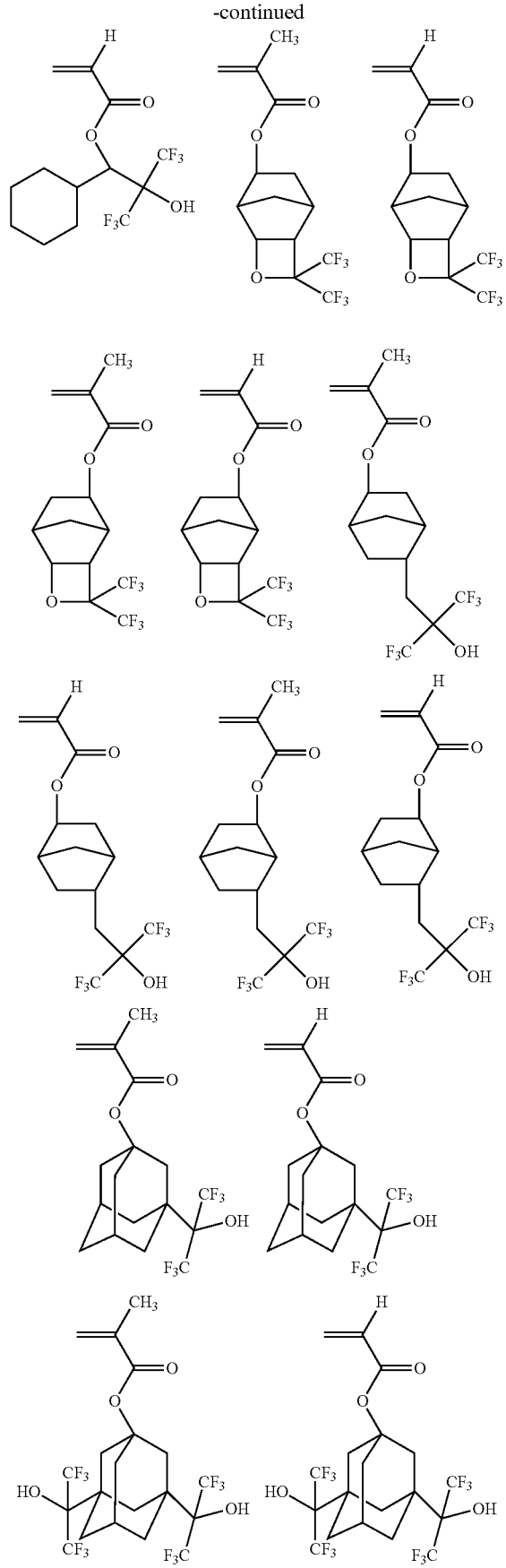

-continued

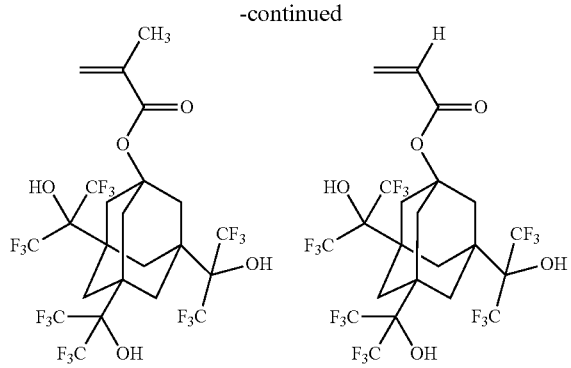

Among them, preferred are
5-(3,3,3-trifluoro-2-hydroxy-2-(trifluoromethyl)propyl)bicyclo[2.2.1]hept-2-yl acrylate,
5-(3,3,3-trifluoro-2-hydroxy-2-(trifluoromethyl)propyl)bicyclo[2.2.1]hept-2-yl methacrylate,
6-(3,3,3-trifluoro-2-hydroxy-2-(trifluoromethyl)propyl)bicyclo[2.2.1]hept-2-yl acrylate,
5-(3,3,3-trifluoro-2-hydroxy-2-(trifluoromethyl)propyl)bicyclo[2.2.1]hept-2-yl methacrylate,
4,4-bis(trifluoromethyl)-3-oxatricyclo[4.2.1.0$^{2,5}$]nonyl acrylate and 4,4-bis(trifluoromethyl)-3-oxatricyclo[4.2.1.0$^{2,5}$] nonyl methacrylate.

When the resin contains a structural unit derived from the above-mentioned fluorine-containing monomer, the content thereof is usually 1 to 20% by mole based on total molar of all the structural units of the resin, and preferably 2 to 15% by mole and more preferably 3 to 10% by mole.

Preferable resin is a resin containing the structural units derived from the monomer having an acid-labile group and the structural units derived from the monomer having no acid-labile group, and more preferable resin is a resin containing the structural units derived from the monomer having an acid-labile group and the structural units derived from the monomer having one or more hydroxyl groups and/or the monomer having a lactone ring. The monomer having an acid-labile group is preferably the monomer represented by the formula (a1-1) or the monomer represented by the formula (a1-2), and is more preferably the monomer represented by the formula (a1-1). The monomer having one or more hydroxyl groups is preferably the monomer represented by the formula (a2-1), and the monomer having a lactone ring is preferably the monomer represented by the formula (a3-1) or (a3-2).

The resin can be produced according to known polymerization methods such as radical polymerization.

The resin usually has 2,500 or more of the weight-average molecular weight, preferably 3,000 or more of the weight-average molecular weight. The resin usually has 50,000 or less of the weight-average molecular weight, preferably has 30,000 or less of the weight-average molecular weight. The weight-average molecular weight can be measured with gel permeation chromatography.

The content of the acid generator is usually 1 part by mass or more per 100 parts by mass of the resin, and preferably 3 parts by mass or more. The content of the acid generator is usually 30 parts by mass or less per 100 parts by mass of the resin, and preferably 25 parts by mass or less. The content of SALT (I) is usually 1 part by mass or more per 100 parts by mass of the resin, and preferably 3 parts by mass or more. The content of the acid generator is usually 30 parts by mass or less per 100 parts by mass of the resin, and preferably 25 parts by mass or less.

The content of the resin in the photoresist composition of the present invention is usually 80% by mass or more based on sum of solid component, and usually 99% by mass or less. In this specification, "solid component" means components other than solvent in the photoresist composition.

The photoresist compositions of the present invention can contain a basic compound as a quencher. The basic compound has the property that it can trap an acid, especially an acid generated from the acid generator by applying a radiation.

The basic compound is preferably a basic nitrogen-containing organic compound, and examples thereof include an amine compound such as an aliphatic amine and an aromatic amine and an ammonium salt. Examples of the aliphatic amine include a primary amine, a secondary amine and a tertiary amine. Examples of the aromatic amine include an aromatic amine in which aromatic ring has one or more amino groups such as aniline and a heteroaromatic amine such as pyridine. Preferable examples thereof include an aromatic amine represented by the formula (C2):

(C2)

wherein $Ar^{c1}$ represents an aromatic hydrocarbon group, and $R^{c5}$ and $R^{c6}$ independently represent a hydrogen atom, an aliphatic hydrocarbon group, a saturated cyclic hydrocarbon group or an aromatic hydrocarbon group, and the aliphatic hydrocarbon group, the saturated cyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group.

The aliphatic hydrocarbon group is preferably an alkyl group and the saturated cyclic hydrocarbon group is preferably a cycloalkyl group. The aliphatic hydrocarbon group preferably has 1 to 6 carbon atoms. The saturated cyclic hydrocarbon group preferably has 5 to 10 carbon atoms. The aromatic hydrocarbon group preferably has 6 to 10 carbon atoms.

As the aromatic amine represented by the formula (C2), an amine represented by the formula (C2-1):

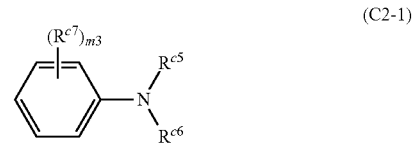

(C2-1)

wherein $R^{c5}$ and $R^{c6}$ are the same as defined above, and $R^{c7}$ is independently in each occurrence an aliphatic hydrocarbon group, an alkoxy group, a saturated cyclic hydrocarbon group or an aromatic hydrocarbon group, and the aliphatic hydrocarbon group, the alkoxy group, the saturated cyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group, and m3 represents an integer of 0 to 3, is preferable. The aliphatic hydrocarbon group is preferably an alkyl group and the saturated cyclic hydrocarbon group is preferably a cycloalkyl group. The aliphatic hydrocarbon group preferably has 1 to 6 carbon atoms. The saturated cyclic hydrocarbon group preferably has 5 to 10 carbon atoms. The aromatic hydrocarbon group preferably has 6 to 10 carbon atoms. The alkoxy group preferably has 1 to 6 carbon atoms.

Examples of the aromatic amine represented by the formula (C2) include 1-naphthylamine, 2-naphthylamine, aniline, diisopropylaniline, 2-methylaniline, 3-methylaniline, 4-methylaniline, 4-nitroaniline, N-methylaniline, N,N-dimethylaniline, and diphenylamine, and among them, preferred is diisopropylaniline and more preferred is 2,6-diisopropylaniline.

Other examples of the basic compound include amines represented by the formulae (C3) to (C11):

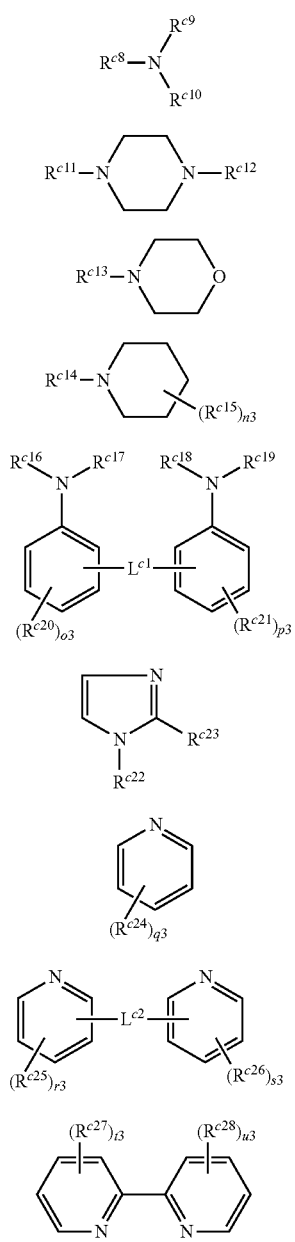

wherein $R^{c8}$, $R^{c20}$, $R^{c21}$, and $R^{c23}$ to $R^{c28}$ independently represent an aliphatic hydrocarbon group, an alkoxy group, a saturated cyclic hydrocarbon group or an aromatic hydrocarbon group, and the aliphatic hydrocarbon group, the alkoxy group, the saturated cyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group, $R^{c9}$, $R^{c10}$, $R^{c11}$ to $R^{c14}$, $R^{c16}$ to $R^{c19}$, and $R^{c22}$ independently represents a hydrogen atom, an aliphatic hydrocarbon group, a saturated cyclic hydrocarbon group or an aromatic hydrocarbon group, and the aliphatic hydrocarbon group, the saturated cyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group, $R^{c15}$ is independently in each occurrence an aliphatic hydrocarbon group, a saturated cyclic hydrocarbon group or an alkanoyl group, $L^{c1}$ and $L^{c2}$ independently represents a divalent aliphatic hydrocarbon group, —CO—, —C(=NH)—, —C(=NR^{c3})—, —S—, —S—S— or a combination thereof and $R^{c3}$ represents a C1-C4 alkyl group, O3 to u3 each independently represents an integer of 0 to 3 and n3 represents an integer of 0 to 8.

The aliphatic hydrocarbon group has preferably 1 to 6 carbon atoms, and the saturated cyclic hydrocarbon group has preferably 3 to 6 carbon atoms, and the alkanoyl group has preferably 2 to 6 carbon atoms, and the divalent aliphatic hydrocarbon group has preferably 1 to 6 carbon atoms. The divalent aliphatic hydrocarbon group is preferably an alkylene group.

Examples of the amine represented by the formula (C3) include hexylamine, heptylamine, octylamine, nonylamine, decylamine, dibutylamine, dipentylamine, dihexylamine, diheptylamine, dioctylamine, dinonylamine, didecylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethydipentylamine, ethyldihexylamine, ethydiheptylamine, ethyldioctylamine, ethyldinonylamine, ethyldidecylamine, dicyclohexylmethylamine, tris[2-(2-methoxyethoxy)ethyl]amine, triisopropanolamine, ethylenediamine, tetramethylenediamine, hexamethylenediamine, 4,4'-diamino-1,2-diphenylethane, 4,4'-diamino-3,3'-dimethyldiphenylmethane and 4,4'-diamino-3,3'-diethyldiphenylmethane.

Examples of the amine represented by the formula (C4) include piperazine. Examples of the amine represented by the formula (C5) include morpholine. Examples of the amine represented by the formula (C6) include piperidine and hindered amine compounds having a piperidine skeleton as disclosed in JP 11-52575 A. Examples of the amine represented by the formula (C7) include 2,2'-methylenebisaniline. Examples of the amine represented by the formula (C8) include imidazole and 4-methylimidazole. Examples of the amine represented by the formula (C9) include pyridine and 4-methylpyridine. Examples of the amine represented by the formula (C10) include di-2-pyridyl ketone, 1,2-di(2-pyridyl)ethane, 1,2-di(4-pyridyl)ethane, 1,3-di(4-pyridyl)propane, 1,2-bis(2-pyridyl)ethene, 1,2-bis(4-pyridyl)ethene, 1,2-di(4-pyridyloxy)ethane, 4,4'-dipyridyl sulfide, 4,4'-dipyridyl disulfide, 2,2'-dipyridylamine and 2,2'-dipicolylamine. Examples of the amine represented by the formula (C11) include bipyridine.

Examples of the quaternary ammonium hydroxide include tetramethylammonium hydroxide, tetrabutylammonium hydroxide, tetrahexylammonium hydroxide, tetraoctylammonium hydroxide, phenyltrimethylammonium hydroxide, (3-trifluoromethylphenyl)trimethylammonium hydroxide and (2-hydroxyethyl) trimethylammonium hydroxide (so-called "choline").

When the photoresist compositions contain the basic compound, the content thereof is usually 0.01 to 1% by mass based on sum of solid component. The content of the basic compound is preferably smaller than total content of SALT (I) and the acid generator other than SALT (I).

The photoresist compositions of the present invention usually contain one or more solvents. Examples of the solvent include a glycol ether ester such as ethyl cellosolve acetate, methyl cellosolve acetate and propylene glycol monomethyl ether acetate; a glycol ether such as propylene glycol monomethyl ether; an acyclic ester such as ethyl lactate, butyl acetate, amyl acetate and ethyl pyruvate; a ketone such as acetone, methyl isobutyl ketone, 2-heptanone and cyclohexanone; and a cyclic ester such as γ-butyrolactone.

The amount of the solvent is usually 90% by weight or more, preferably 92% by weight or more preferably 94% by weight or more based on total amount of the photoresist composition of the present invention. The amount of the solvent is usually 99.9% by weight or less and preferably 99% by weight or less based on total amount of the photoresist composition of the present invention.

The photoresist compositions of the present invention can contain, if necessary, a small amount of various additives such as a sensitizer, a dissolution inhibitor, other polymers, a surfactant, a stabilizer and a dye as long as the effect of the present invention is not prevented.

The photoresist compositions of the present invention are useful for a chemically amplified photoresist composition.

A photoresist pattern can be produced by the following steps (1) to (5):

(1) a step of applying the first or second photoresist composition of the present invention on a substrate, (2) a step of forming a photoresist film by conducting drying, (3) a step of exposing the photoresist film to radiation, (4) a step of baking the exposed photoresist film, and (5) a step of developing the baked photoresist film with an alkaline developer, thereby forming a photoresist pattern.

The applying of the photoresist composition on a substrate is usually conducted using a conventional apparatus such as spin coater. The photoresist composition is preferably filtrated with filter having a pore size of 0.01 to 0.2 μm before applying. Examples of the substrate include a silicon wafer or a quartz wafer on which a sensor, a circuit, a transistor or the like is formed.

The formation of the photoresist film is usually conducted using a heating apparatus such as hot plate or a decompressor, and the heating temperature is usually 50 to 200° C., and the operation pressure is usually 1 to $1.0*10^5$ Pa.

The photoresist film obtained is exposed to radiation using an exposure system. The exposure is usually conducted through a mask having a pattern corresponding to the desired photoresist pattern. Examples of the exposure source include a light source radiating laser light in a UV-region such as a KrF excimer laser (wavelength: 248 nm), an ArF excimer laser (wavelength: 193 nm) and a $F_2$ laser (wavelength: 157 nm), and a light source radiating harmonic laser light in a far UV region or a vacuum UV region by wavelength conversion of laser light from a solid laser light source (such as YAG or semiconductor laser).

The temperature of baking of the exposed photoresist film is usually 50 to 200° C., and preferably 70 to 150° C.

The development of the baked photoresist film is usually carried out using a development apparatus. The alkaline developer used may be any one of various alkaline aqueous solution used in the art. Generally, an aqueous solution of tetramethylammonium hydroxide or (2-hydroxyethyl)trimethylammoniumhydroxide (commonly known as "choline") is often used. After development, the photoresist pattern formed is preferably washed with ultrapure water, and the remained water on the photoresist pattern and the substrate is preferably removed.

The photoresist composition of the present invention provides a photoresist pattern showing good Exposure Latitude (EL), and therefore, the photoresist composition of the present invention is suitable for ArF excimer laser lithography, KrF excimer laser lithography, ArF immersion lithography, EUV (extreme ultraviolet) lithography, EUV immersion lithography and EB (electron beam) lithography. Further, the photoresist composition of the present invention can especially be used for EUV lithography and EB lithography.

EXAMPLES

The present invention will be described more specifically by Examples, which are not construed to limit the scope of the present invention.

The "%" and "part(s)" used to represent the content of any component and the amount of any material used in the following examples and comparative examples are on a mass basis unless otherwise specifically noted. The weight-average molecular weight of any material used in the following examples is a value found by gel permeation chromatography [Column: Three of TSKgel Multipore HXL-M with guard column, manufactured by TOSOH CORPORATION, Solvent: tetrahydrofuran, Flow rate: 1.0 mL/min., Detector: RI Detector, Column temperature: 40° C., Injection volume: 100 μL] using standard polystyrene as a standard reference material. Structures of compounds were determined by mass spectrometry (Liquid Chromatography: 1100 Type, manufactured by AGILENT TECHNOLOGIES LTD., Mass Spectrometry: LC/MSD Type, manufactured by AGILENT TECHNOLOGIES LTD.).

Example 1

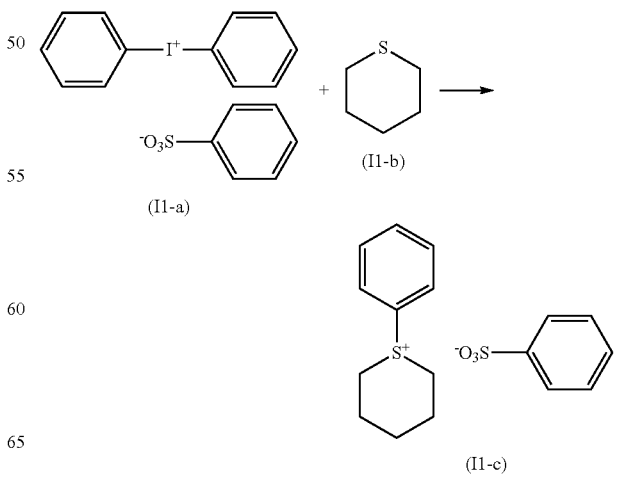

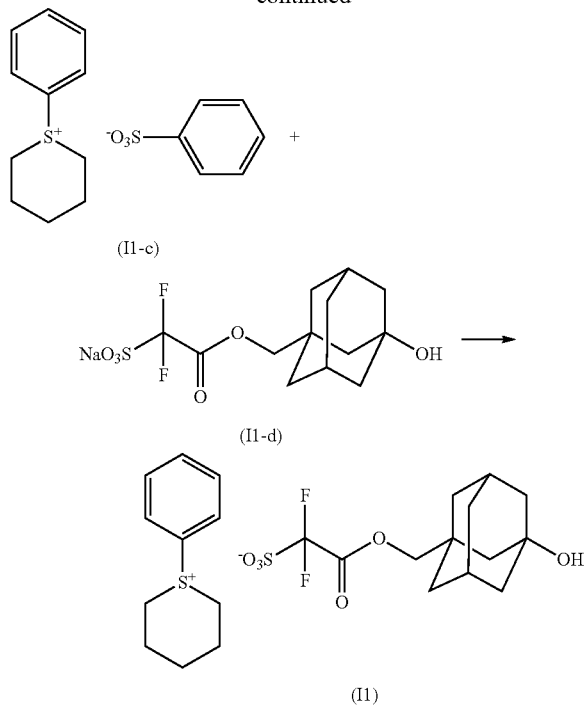

(I1-c)

(I1-d)

(I1)

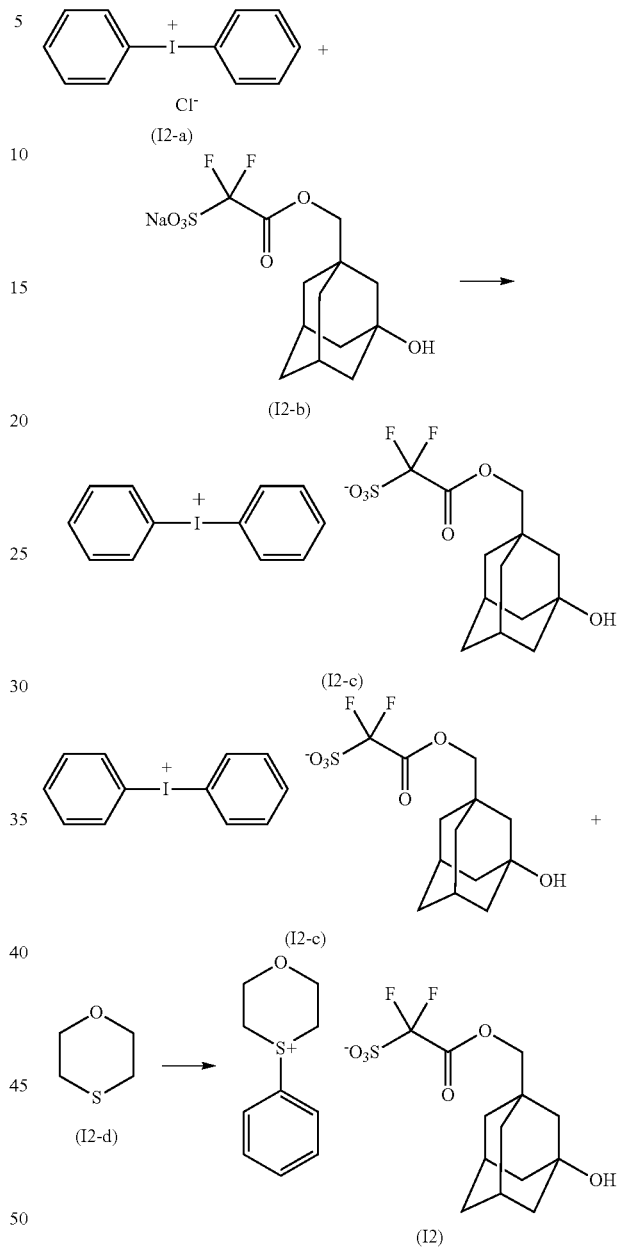

(I2-a)

(I2-b)

(I2-c)

(I2-c)

(I2-d)

(I2)

To the solution containing 10.00 parts of the salt represented by the formula (I1-a), 2.33 parts of the compound represented by the formula (I1-b) and 50 parts of monochlorobenzene, added was 0.17 part of copper (II) dibenzoate. The resultant mixture was stirred at 100° C. for 2 hours. The mixture was cooled down to 23° C., and 10 parts of acetonitrile was added thereto, and the resultant mixture was stirred for 30 minutes followed by concentration. The residue obtained was mixed with 161.60 parts of tert-butyl methyl ether, and the mixture obtained was stirred at 23° C. for 30 minutes. After removing a supernatant, the concentration was conducted. To the residue, 20 parts of acetonitrile was added, and the resultant mixture was stirred at 23° C. for 30 minutes followed by concentration to obtain 5.25 parts of the salt represented by the formula (I1-c).

To the solution containing 3.24 parts of the salt represented by the formula (I1-d) which had been produced according to the method described in JP 2008-209917 A, and 48.70 parts of chloroform, 3.38 parts of the salt represented by the formula (I1-c) and 33.83 parts of ion-exchanged water were added. The resultant mixture was stirred at 23° C. for 15 hours. The reaction mixture was separated to obtain an organic layer. The organic layer was washed with 24.35 parts of ion-exchanged water. This washing was repeated five times. The organic layer was concentrated. The residue was mixed with 20 parts of ethyl acetate. After removing a supernatant, the concentration was conducted. To the residue, 20 parts of acetonitrile was added, and the resultant mixture was stirred at 23° C. for 30 minutes followed by concentration. To the residue, 20 parts of tert-butyl methyl ether was added, and the resultant mixture was stirred at 23° C. for 30 minutes. After removing a supernatant, the concentration was conducted. To the residue, 20 parts of acetonitrile was added, and the resultant mixture was stirred at 23° C. for 30 minutes followed by concentration to obtain 1.24 parts of the salt represented by the formula (I1). This is called as Salt I1.

MS (ESI(+) Spectrum): M$^+$ 179.1
MS (ESI(−) Spectrum): M$^−$ 339.1

Example 2

A mixture containing 35.00 parts of the salt represented by the formula (I2-b) which had been produced according to the method described in JP 2008-209917 A, 30.58 parts of the salt represented by the formula (I2-a), 100 parts of chloroform and 50 parts of ion-exchanged water was stirred at 23° C. for 15 hours. The reaction mixture was separated to obtain an organic layer. The organic layer was washed with 30 parts of ion-exchanged water. This washing was repeated five times. The organic layer was concentrated. The residue was mixed with 100 parts of tert-butyl methyl ether. The resultant mixture was stirred at 23° C. for 30 minutes followed by filtrating to obtain 44.93 parts of the salt represented by the formula (I2-c).

A mixture containing 20.00 parts of the salt represented by the formula (I2-c), 3.36 parts of the compound represented by the formula (I2-d) and 100 parts of monochlorobenzene was stirred at 23° C. for 30 minutes. To the resultant mixture, added was 0.25 part of copper (II) dibenzoate. The resultant mixture was stirred at 100° C. for 1 hour. The mixture was concentrated, and 200 parts of chloroform, 8 parts of acetonitrile and 50 parts of ion-exchanged water were added to the residue obtained, and the resultant mixture was stirred at 23° C. for 30 minutes followed by separation. The organic layer obtained was washed with 50 parts of ion-exchanged water. This washing was repeated four times. The organic layer was concentrated. To the residue, 37 parts of acetonitrile was added, and the resultant mixture was concentrated. To the residue, 71.80 parts of tert-butyl methyl ether was added. After removing a supernatant, the residue was dissolved in acetonitrile followed by concentration to obtain 2.44 parts of the salt represented by the formula (I2). This is called as Salt I2.

MS (ESI(+) Spectrum): M⁺ 181.1
MS (ESI(−) Spectrum): M⁻ 339.1

Example 3

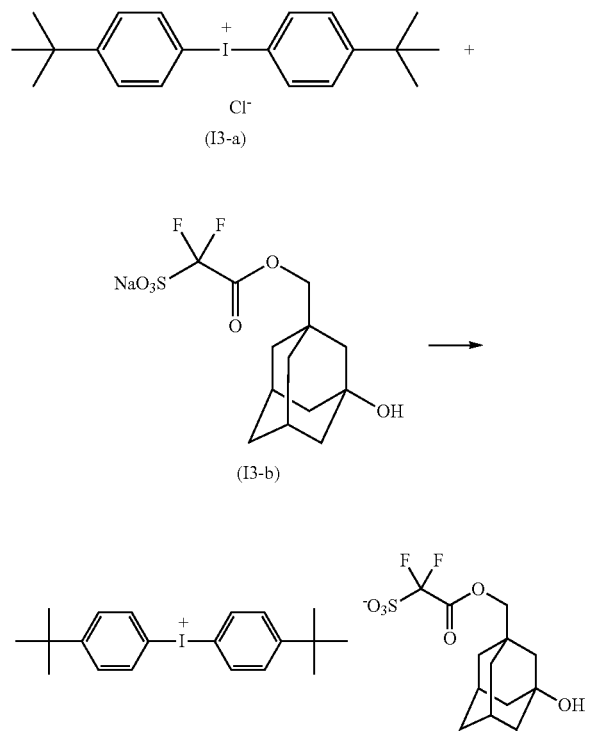

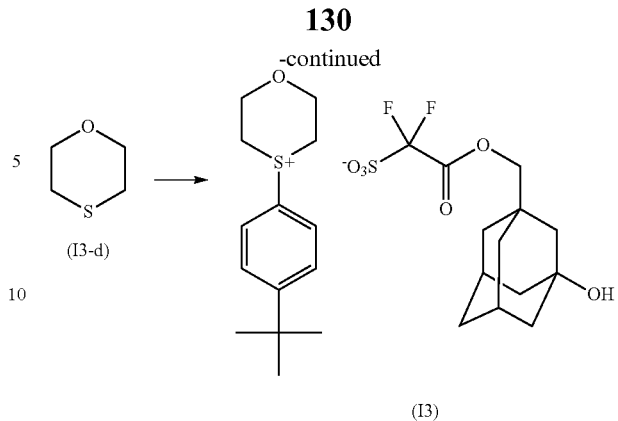

A mixture containing 30.00 parts of the salt represented by the formula (I3-b) which had been produced according to the method described in JP 2008-209917 A, 35.50 parts of the salt represented by the formula (I3-a), 100 parts of chloroform and 50 parts of ion-exchanged water was stirred at 23° C. for 15 hours. The reaction mixture was separated to obtain an organic layer. The organic layer was washed with 30 parts of ion-exchanged water. This washing was repeated five times. The organic layer was concentrated. The residue was mixed with 100 parts of tert-butyl methyl ether. The resultant mixture was stirred at 23° C. for 30 minutes followed by filtrating to obtain 48.57 parts of the salt represented by the formula (I3-c).

A mixture containing 20.00 parts of the salt represented by the formula (I3-c), 2.84 parts of the compound represented by the formula (I3-d) and 250 parts of monochlorobenzene was stirred at 23° C. for 30 minutes. To the resultant mixture, added was 0.21 part of copper (II) dibenzoate. The resultant mixture was stirred at 100° C. for 1 hour. The mixture was concentrated, and 200 parts of chloroform and 50 parts of ion-exchanged water were added to the residue obtained, and the resultant mixture was stirred at 23° C. for 30 minutes followed by separation. The organic layer obtained was washed with 50 parts of ion-exchanged water. This washing was repeated five times. The organic layer was concentrated. To the residue, 53.51 parts of acetonitrile was added, and the resultant mixture was concentrated. To the residue, 113.05 parts of tert-butyl methyl ether was added followed by filtrating to obtain 10.47 parts of the salt represented by the formula (I3). This is called as Salt I3.

MS (ESI(+) Spectrum): M⁺ 237.1
MS (ESI(−) Spectrum): M⁻ 339.1

Example 4

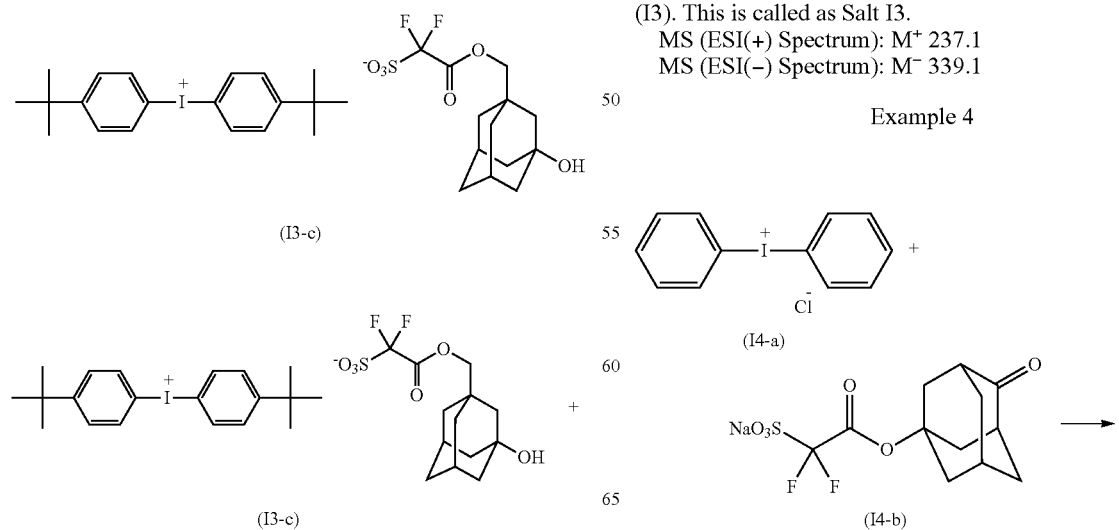

-continued

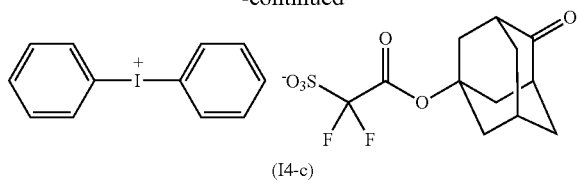

(I4-c)

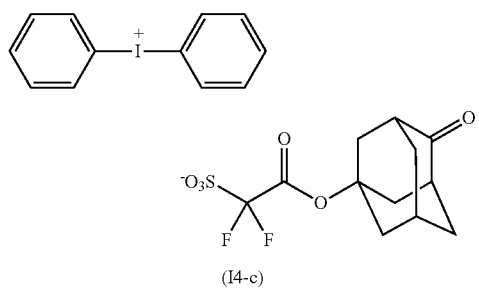

(I4-c)

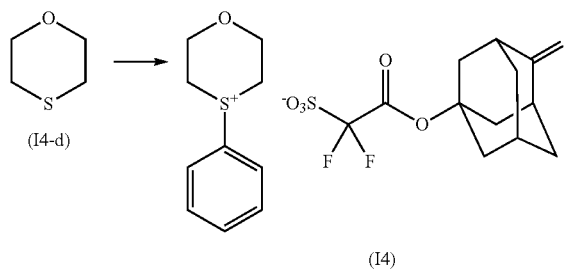

(I4)

A mixture containing 10.00 parts of the salt represented by the formula (I4-b) which had been produced according to the method described in JP 2008-209917 A, 8.31 parts of the salt represented by the formula (I4-a), 50 parts of chloroform and 25 parts of ion-exchanged water was stirred at 23° C. for 15 hours. The reaction mixture was separated to obtain an organic layer. The organic layer was washed with 15 parts of ion-exchanged water. This washing was repeated five times. The organic layer was concentrated. The residue was mixed with 50 parts of tert-butyl methyl ether. The resultant mixture was stirred at 23° C. for 30 minutes followed by filtrating to obtain 9.88 parts of the salt represented by the formula (I4-c).

A mixture containing 9.88 parts of the salt represented by the formula (I4-c), 1.70 parts of the compound represented by the formula (I4-d) and 39.56 parts of monochlorobenzene was stirred at 23° C. for 30 minutes. To the resultant mixture, added was 0.12 part of copper (II) dibenzoate. The resultant mixture was stirred at 100° C. for 30 minutes. The mixture was concentrated, and 49.45 parts of chloroform and 12.36 parts of ion-exchanged water were added to the residue obtained, and the resultant mixture was stirred at 23° C. for 30 minutes followed by separation. The organic layer obtained was washed with 12.36 parts of ion-exchanged water. This washing was repeated eight times. The organic layer was concentrated. To the residue, 43.75 parts of tert-butyl methyl ether was added followed by filtrating to obtain 2.74 parts of the salt represented by the formula (I4). This is called as Salt I4.

MS (ESI(+) Spectrum): M⁺ 181.1
MS (ESI(−) Spectrum): M⁻ 323.0

Example 5

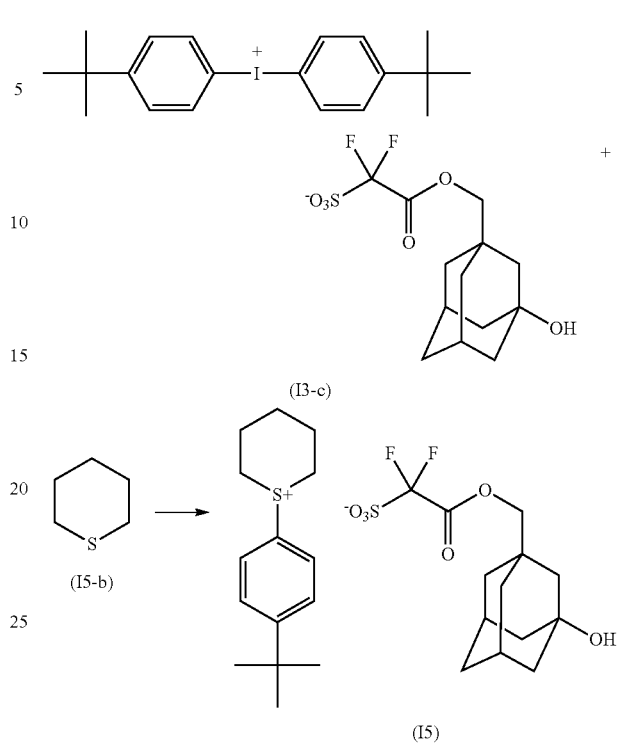

A mixture containing 12.00 parts of the salt represented by the formula (I3-c) obtained according to the same manner as that described in Example 3, 1.67 parts of the compound represented by the formula (I5-b) and 60 parts of monochlorobenzene was stirred at 23° C. for 30 minutes. To the resultant mixture, added was 0.13 part of copper (II) dibenzoate. The resultant mixture was stirred at 100° C. for 1 hour. The mixture was concentrated, and 60 parts of chloroform and 15 parts of ion-exchanged water were added to the residue obtained, and the resultant mixture was stirred at 23° C. for 30 minutes followed by separation. The organic layer obtained was washed with 15 parts of ion-exchanged water. This washing was repeated five times. The organic layer was concentrated. To the residue, 83.40 parts of tert-butyl methyl ether was added followed by filtrating to obtain 7.97 parts of the salt represented by the formula (I5). This is called as Salt I5.

MS (ESI(+) Spectrum): M⁺ 235.2
MS (ESI(−) Spectrum): M⁻ 339.1

Example 6

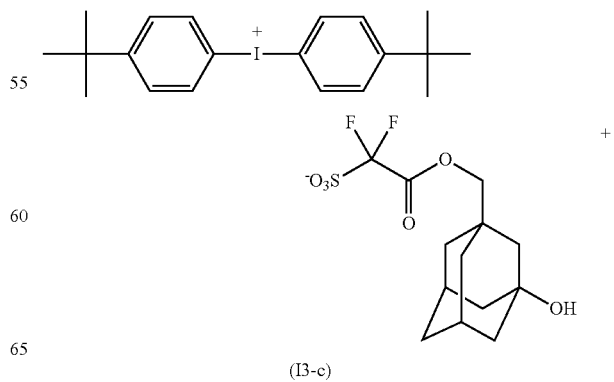

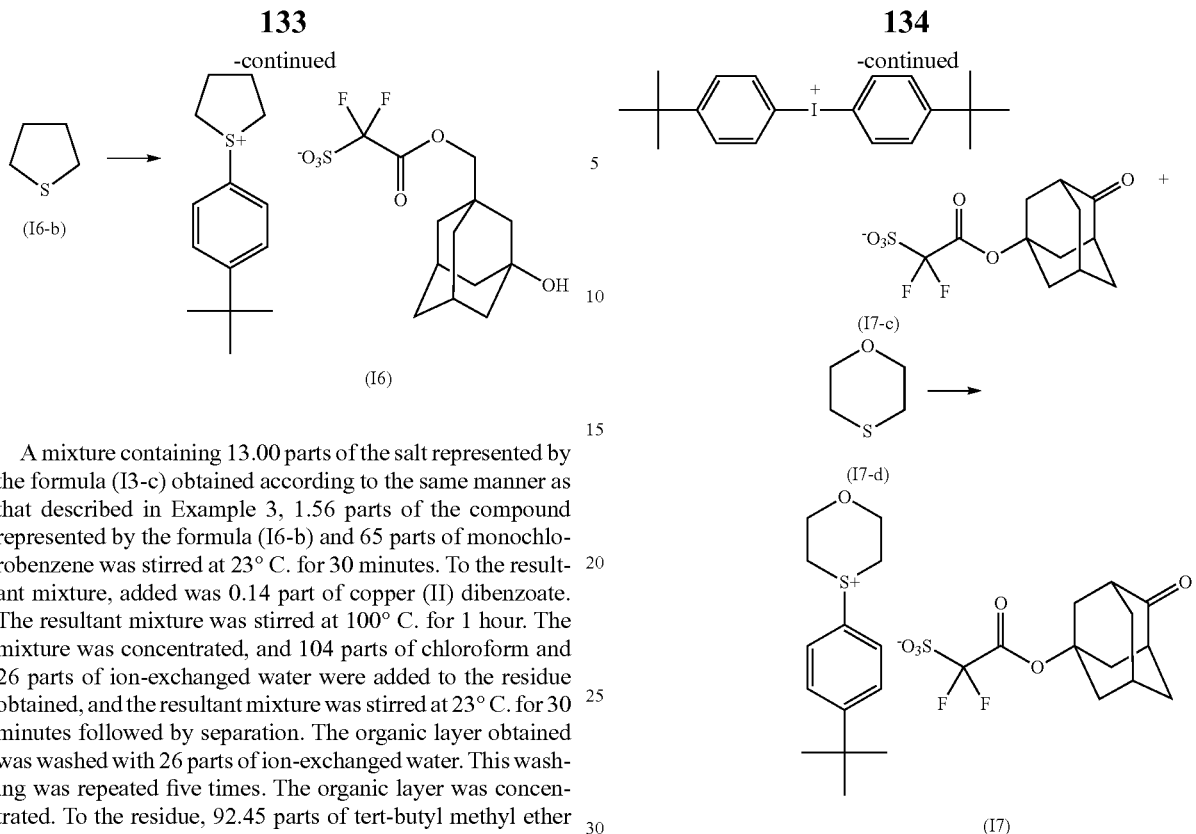

A mixture containing 13.00 parts of the salt represented by the formula (I3-c) obtained according to the same manner as that described in Example 3, 1.56 parts of the compound represented by the formula (I6-b) and 65 parts of monochlorobenzene was stirred at 23° C. for 30 minutes. To the resultant mixture, added was 0.14 part of copper (II) dibenzoate. The resultant mixture was stirred at 100° C. for 1 hour. The mixture was concentrated, and 104 parts of chloroform and 26 parts of ion-exchanged water were added to the residue obtained, and the resultant mixture was stirred at 23° C. for 30 minutes followed by separation. The organic layer obtained was washed with 26 parts of ion-exchanged water. This washing was repeated five times. The organic layer was concentrated. To the residue, 92.45 parts of tert-butyl methyl ether was added followed by separating a supernatant. To the residue, acetonitrile was added followed by concentrating to obtain 6.77 parts of the salt represented by the formula (I6). This is called as Salt I6.

MS (ESI(+) Spectrum): $M^+$ 221.1
MS (ESI(−) Spectrum): $M^−$ 339.1

Example 7

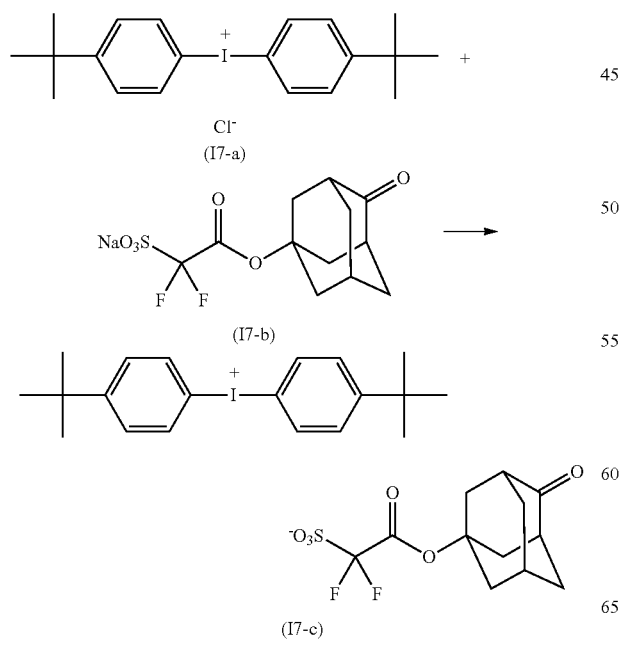

A mixture containing 11.26 parts of the salt represented by the formula (I7-a), 10.00 parts of the salt represented by the formula (I7-b), 50 parts of chloroform and 25 parts of ion-exchanged water was stirred at 23° C. for 15 hours. The reaction mixture was separated to obtain an organic layer. The organic layer was washed with 15 parts of ion-exchanged water. This washing was repeated five times. The organic layer was concentrated. The residue was mixed with 50 parts of tert-butylmethyl ether. The resultant mixture was stirred at 23° C. for 30 minutes followed by filtrating to obtain 11.75 parts of the salt represented by the formula (I7-c).

A mixture containing 11.71 parts of the salt represented by the formula (I7-c), 1.70 parts of the compound represented by the formula (I7-d) and 46.84 parts of monochlorobenzene was stirred at 23° C. for 30 minutes. To the resultant mixture, added was 0.12 part of copper (II) dibenzoate. The resultant mixture was stirred at 100° C. for 30 minutes. The mixture was concentrated, and 50 parts of chloroform and 12.50 parts of ion-exchanged water were added to the residue obtained, and the resultant mixture was stirred at 23° C. for 30 minutes followed by separation. The organic layer obtained was washed with 12.50 parts of ion-exchanged water. This washing was repeated eight times. The organic layer was concentrated. To the residue, 50 parts of tert-butyl methyl ether was added followed by filtrating to obtain 6.84 parts of the salt represented by the formula (I7). This is called as Salt I7.

MS (ESI(+) Spectrum): $M^+$ 237.1
MS (ESI(−) Spectrum): $M^−$ 323.0

Example 8

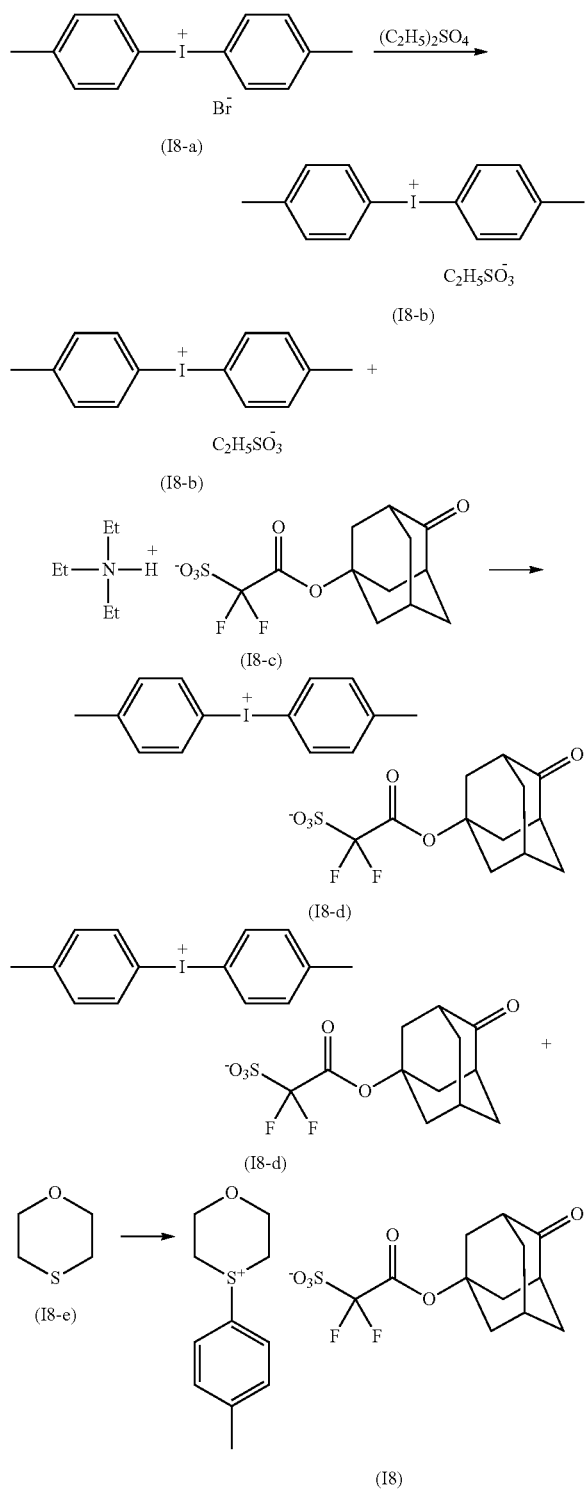

To the mixture containing 1.97 parts of the salt represented by the formula (I8-a) and 30 parts of chloroform, 0.94 parts of diethyl sulfate was added dropwise. The resultant mixture was stirred at 23° C. for 1 hour to prepare a solution containing a salt represented by the formula (I8-b). To the solution obtained, 3.23 parts of the salt represented by the formula (I8-c) which had been produced according to the method described in JP 2008-94835 A and 15 parts of ion-exchanged water were added, and the resultant mixture was stirred at 23° C. for 15 hours. The reaction mixture was separated to obtain an organic layer. The organic layer was washed with 10 parts of ion-exchanged water. This washing was repeated five times. The organic layer was concentrated. The residue was mixed with 25.40 parts of tert-butyl methyl ether. The resultant mixture was stirred at 23° C. for 30 minutes followed by filtrating to obtain 2.79 parts of the salt represented by the formula (I8-d).

A mixture containing 2.70 parts of the salt represented by the formula (I8-d), 0.67 parts of the compound represented by the formula (I8-e) and 21.60 parts of monochlorobenzene was stirred at 23° C. for 30 minutes. To the resultant mixture, added was 0.03 part of copper (II) dibenzoate. The resultant mixture was stirred at 100° C. for 30 minutes. The mixture was concentrated, and 40.50 parts of chloroform, 13.50 parts of ion-exchanged water and 0.15 part of 28% ammonia water were added to the residue obtained, and the resultant mixture was stirred at 23° C. for 30 minutes followed by separation. The organic layer obtained was washed with 13.50 parts of ion-exchanged water. This washing was repeated three times. The organic layer was concentrated. To the residue, 36.55 parts of tert-butyl methyl ether was added followed by filtrating to obtain 1.16 parts of the salt represented by the formula (I8). This is called as Salt I8.

MS (ESI(+) Spectrum): M$^+$ 195.1
MS (ESI(−) Spectrum): M$^-$ 323.0

Example 9

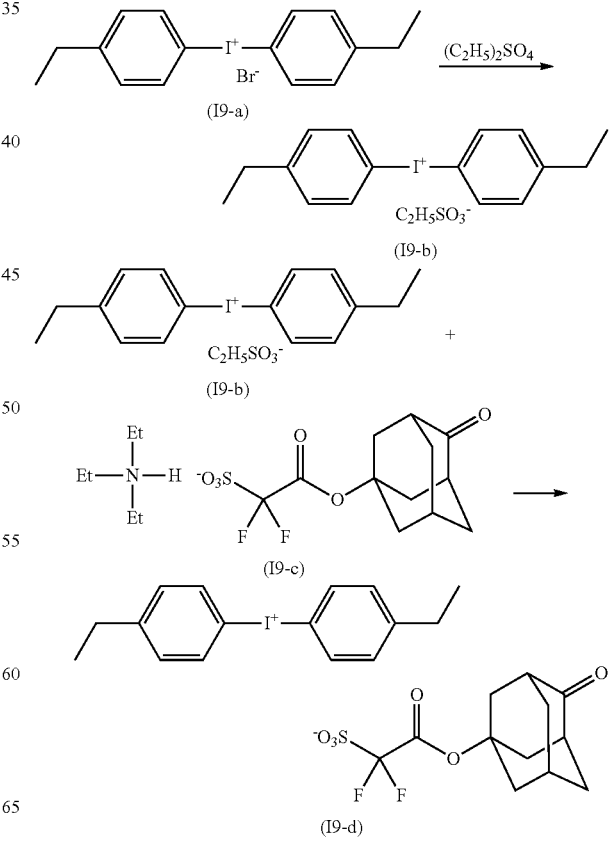

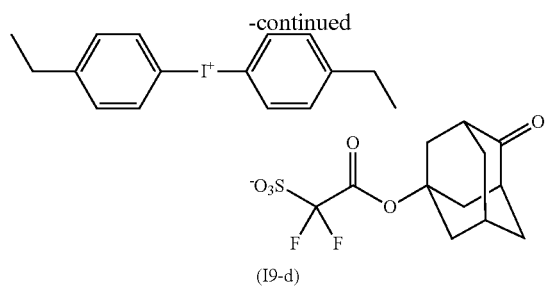

(I9-d)

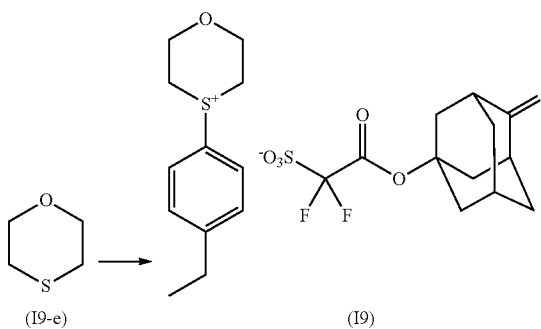

(I9-e) (I9)

To the mixture containing 1.97 parts of the salt represented by the formula (I9-a) and 30 parts of chloroform, 0.87 parts of diethyl sulfate was added dropwise. The resultant mixture was stirred at 23° C. for 1 hour to prepare a solution containing a salt represented by the formula (I9-b). To the solution obtained, 3.01 parts of the salt represented by the formula (I9-c) and 15 parts of ion-exchanged water were added, and the resultant mixture was stirred at 23° C. for 15 hours. The reaction mixture was separated to obtain an organic layer. The organic layer was washed with 10 parts of ion-exchanged water. This washing was repeated six times. The organic layer was concentrated. The residue was mixed with 21.20 parts of tert-butyl methyl ether. The resultant mixture was stirred at 23° C. for 30 minutes followed by filtrating to obtain 2.57 parts of the salt represented by the formula (I9-d).

A mixture containing 2.49 parts of the salt represented by the formula (I9-d), 0.59 parts of the compound represented by the formula (I9-e) and 20 parts of monochlorobenzene was stirred at 23° C. for 30 minutes. To the resultant mixture, added was 0.03 part of copper (II) dibenzoate. The resultant mixture was stirred at 100° C. for 30 minutes. The mixture was concentrated, and 37.50 parts of chloroform, 12.50 parts of ion-exchanged water and 0.15 part of 28% ammonia water were added to the residue obtained, and the resultant mixture was stirred at 23° C. for 30 minutes followed by separation. The organic layer obtained was washed with 12.50 parts of ion-exchanged water. This washing was repeated three times. The organic layer was concentrated. To the residue, 18.45 parts of tert-butyl methyl ether was added followed by filtrating to obtain 1.30 parts of the salt represented by the formula (I9). This is called as Salt I9.

MS (ESI(+) Spectrum): $M^+$ 209.1
MS (ESI(-) Spectrum): $M^-$ 323.0

Example 10

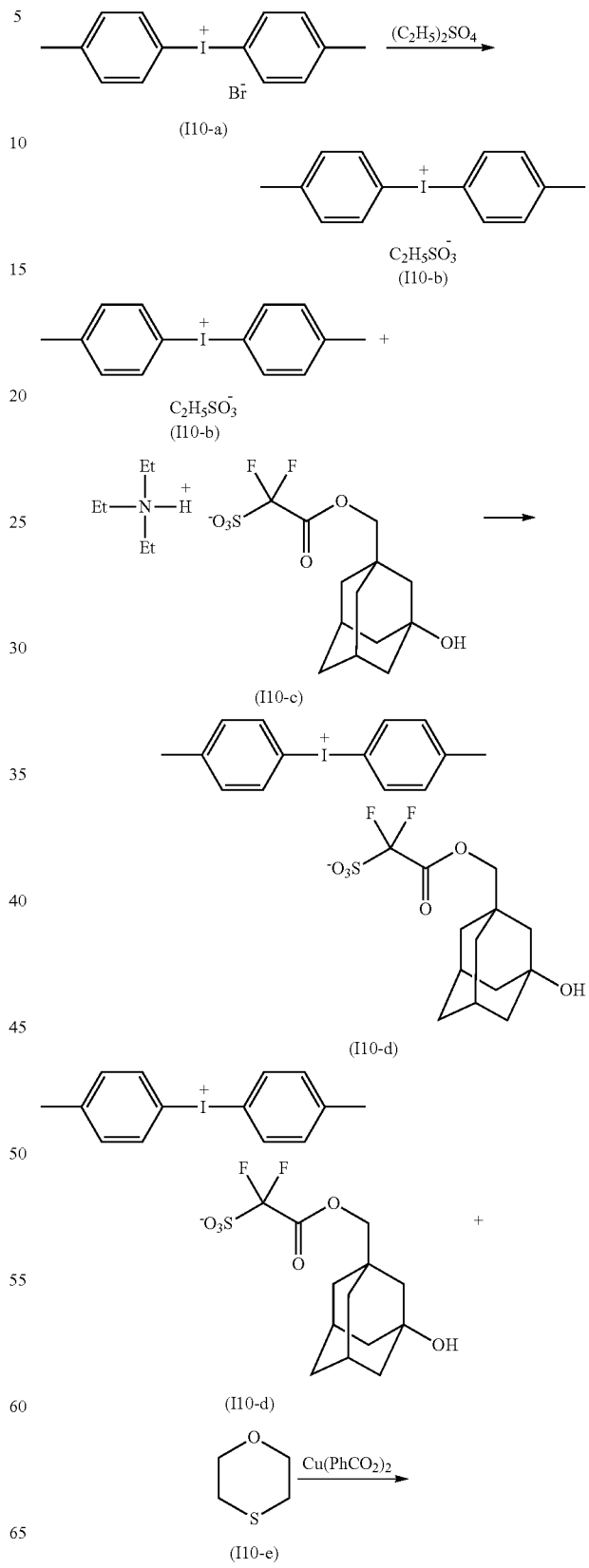

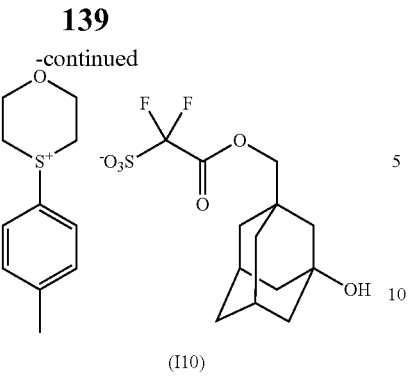

(I10)

To the mixture containing 4.44 parts of the salt represented by the formula (I10-a) and 90 parts of methanol, 2.11 parts of diethyl sulfate was added dropwise. The resultant mixture was stirred at 23° C. for 1 hour to prepare a solution containing a salt represented by the formula (I10-b). To the solution obtained, 7.55 parts of the salt represented by the formula (I10-c) was added, and the resultant mixture was stirred at 23° C. for 12 hours. The reaction mixture was concentrated. To the residue obtained, 55.28 parts of ion-exchanged water was added. The resultant mixture was stirred at 23° C. for 30 minutes followed by removing a supernatant. To the residue obtained, 10 parts of acetonitrile was added. The resultant mixture was stirred at 23° C. for 30 minutes followed by concentrating to obtain 3.57 parts of the salt represented by the formula (I10-d).

A mixture containing 3.57 parts of the salt represented by the formula (I10-d), 0.86 parts of the compound represented by the formula (I10-e) and 35.68 parts of monochlorobenzene was stirred at 23° C. for 30 minutes. To the resultant mixture, added was 0.04 part of copper (II) dibenzoate. The resultant mixture was stirred at 100° C. for 30 minutes. The mixture was concentrated, and 44.60 parts of chloroform, 14.87 parts of ion-exchanged water and 0.15 part of 28% ammonia water were added to the residue obtained, and the resultant mixture was stirred at 23° C. for 30 minutes followed by separation. The organic layer obtained was washed with 14.87 parts of ion-exchanged water. This washing was repeated three times. The organic layer was concentrated. To the residue, 18.65 parts of tert-butyl methyl ether was added followed by removing a supernatant. To the residue, 10 parts of acetonitrile was added. The resultant mixture was stirred at 23° C. for 30 minutes followed by concentrating to obtain 0.85 part of the salt represented by the formula (I10). This is called as Salt I10.

MS (ESI(+) Spectrum): M⁺ 195.1
MS (ESI(−) Spectrum): M⁻ 339.1

Example 11

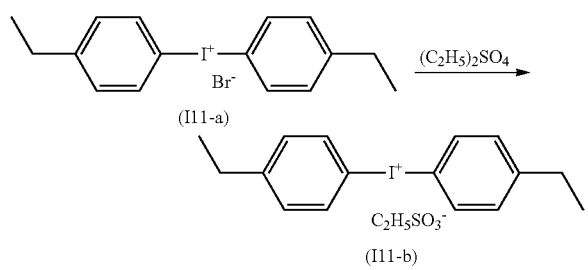

(I11-a)

(I11-b)

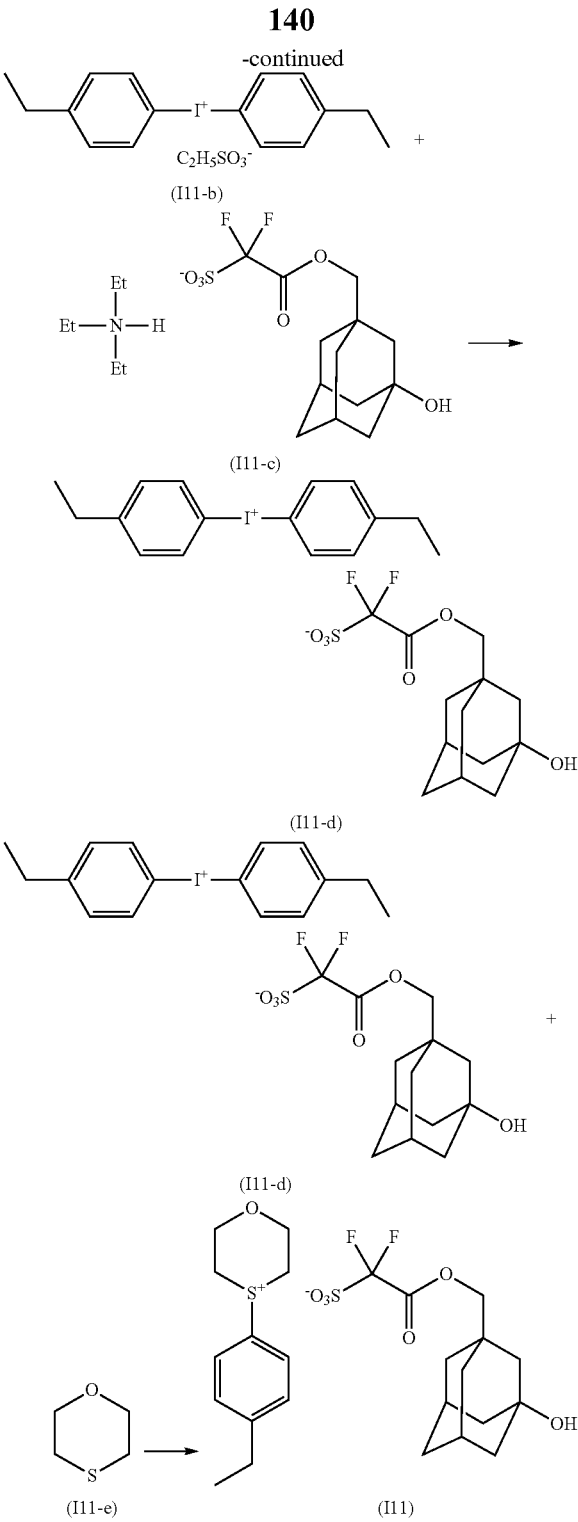

To the mixture containing 1.97 parts of the salt represented by the formula (I11-a) and 40 parts of methanol, 0.87 parts of diethyl sulfate was added dropwise. The resultant mixture was stirred at 23° C. for 1 hour to prepare a solution containing a salt represented by the formula (I11-b). To the solution obtained, 3.13 parts of the salt represented by the formula (I11-c) was added, and the resultant mixture was stirred at 23° C. for 12 hours. The reaction mixture was concentrated. To the residue obtained, 30.50 parts of ion-exchanged water was added. The resultant mixture was stirred at 23° C. for 30 minutes followed by filtrating to obtain 2.10 parts of the salt represented by the formula (I11-d).

A mixture containing 2.01 parts of the salt represented by the formula (I11-d), 0.46 parts of the compound represented by the formula (I11-e) and 18.40 parts of monochlorobenzene was stirred at 23° C. for 30 minutes. To the resultant mixture, added was 0.02 part of copper (II) dibenzoate. The resultant mixture was stirred at 100° C. for 30 minutes. The mixture was concentrated, and 34.50 parts of chloroform, 11.50 parts of ion-exchanged water and 0.15 part of 28% ammonia water were added to the residue obtained, and the resultant mixture was stirred at 23° C. for 30 minutes followed by separation. The organic layer obtained was washed with 11.50 parts of ion-exchanged water. This washing was repeated three times. The organic layer was concentrated. To the residue, 13.45 parts of tert-butyl methyl ether was added followed by filtrating to obtain 0.77 part of the salt represented by the formula (I11). This is called as Salt I11.

MS (ESI(+) Spectrum): M⁺ 209.1

MS (ESI(−) Spectrum): M⁻ 339.1

Monomers used in the following Resin Synthesis Examples 1 to 2 are following monomers (A), (B), (C), (D), (E) and (F).

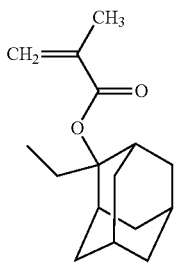
(A)

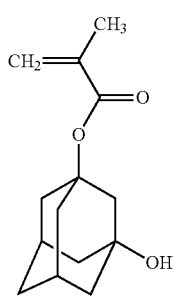
(B)

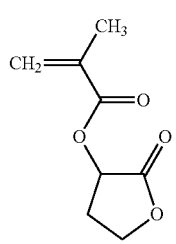
(C)

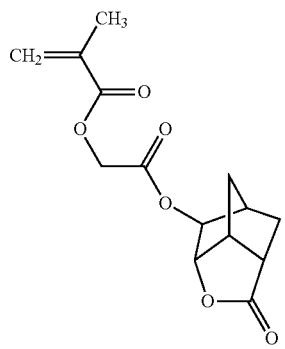
(D)

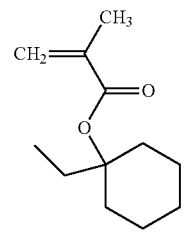
(E)

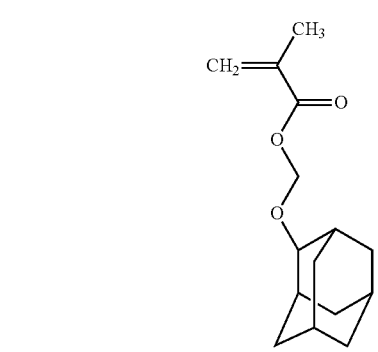
(F)

Resin Synthesis Example 1

The monomers (A), (E), (B), (C) and (D) were mixed in a molar ratio of 30/14/6/20/30 (monomer (A)/monomer(E)/monomer (B)/monomer (C)/monomer (D)), and 1,4-dioxane in 1.5 times part based on total parts of all monomers was added to prepare a mixture. To the mixture, azobisisobutyronitrile as an initiator in a ratio of 1 mol % based on all monomer molar amount and azobis(2,4-dimethylvaleronitrile) as an initiator in a ratio of 3 mol % based on all monomer molar amount were added, and the obtained mixture was heated at 75° C. for about 5 hours. The reaction mixture obtained was poured into a large amount of a mixture of methanol and water (ratio=4/1) to cause precipitation. The precipitate was collected by filtration and then, was dissolved followed by poured the resultant solution into a large amount of a mixture of methanol and water to cause precipitation. This operation was repeated twice for purification. As a result, a resin having a weight-average molecular weight of about 7.2×10³ was obtained in a yield of 78%. This resin is called as resin A1. Resin A1 had the following structural units.

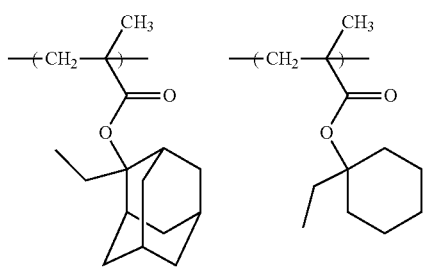

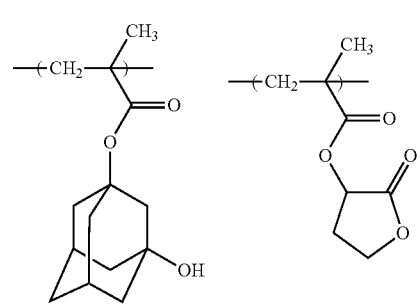

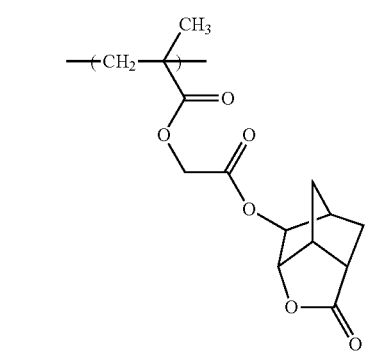

Resin Synthesis Example 2

The monomers (F), (C) and (B) were mixed in a molar ratio of 40/40/20 (monomer (F)/monomer (C)/monomer (B)), and 1,4-dioxane in 1.5 times part based on total parts of all monomers was added to prepare a mixture. To the mixture, azobisisobutyronitrile as an initiator in a ratio of 0.8 mol % based on all monomer molar amount and azobis(2,4-dimethylvaleronitrile) as an initiator in a ratio of 2.4 mol % based on all monomer molar amount were added, and the obtained mixture was heated at 70° C. for about 5 hours. The reaction mixture obtained was poured into a large amount of a mixture of methanol and water (ratio=3/1) to cause precipitation. The precipitate was collected by filtration and then, was dissolved in followed by poured the resultant solution into a large amount of a mixture of methanol and water to cause precipitation. This operation was repeated twice for purification. As a result, a resin having a weight-average molecular weight of about $1.0 \times 10^4$ was obtained in a yield of 78%. This resin is called as resin A2. Resin A2 had the following structural units.

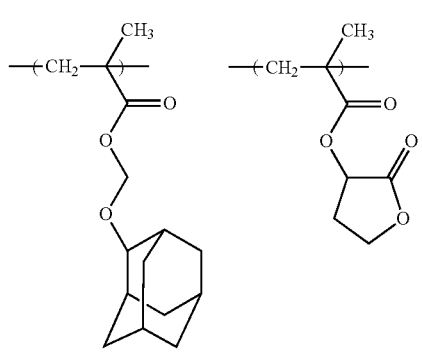

Examples 12 to 29 and Comparative Example 1

| <Resin> |
|---|
| Resin A1, A2 |
| <Acid generator> |

| | |
|---|---|
| I1: | Salt I1 |
| I2: | Salt I2 |
| I3: | Salt I3 |
| I4: | Salt I4 |
| I5: | Salt I5 |
| I6: | Salt I6 |
| I7: | Salt I7 |
| I8: | Salt I8 |
| I9: | Salt I9 |
| I10: | Salt I10 |
| I11: | Salt I11 |

B1:

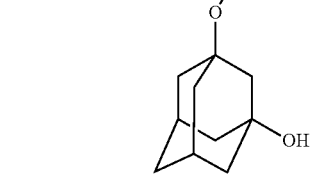

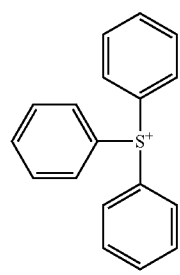 [SMILES: c1ccc([S+](c2ccccc2)c2ccccc2)cc1]

-continued

B2:

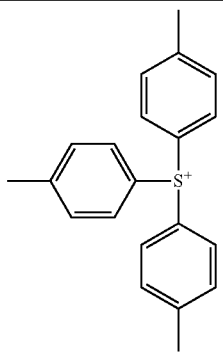

B3:

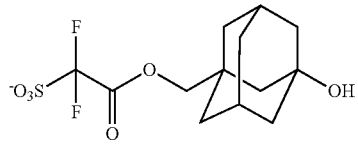

| | <Quencher> |
|---|---|
| C1: | 2,6-diisopropylaniline |

<Solvent>

| E1: | propylene glycol monomethyl ether acetate | 265 parts |
|---|---|---|
| | propylene glycol monomethyl ether | 20 parts |
| | 2-heptanone | 20 parts |
| | γ-butyrolactone | 3.5 parts |

The following components were mixed and dissolved, further, filtrated through a fluorine resin filter having pore diameter of 0.2 to prepare photoresist compositions.
Resin (kind and amount are described in Table 6)
Acid generator (kind and amount are described in Table 6)
Quencher (kind and amount are described in Table 6)
Solvent E1

TABLE 6

| Ex. No. | Resin (kind/amount (part)) | Acid generator (kind/amount (part)) | Quencher (kind/amount (part)) | PB (° C.) | PEB (° C.) |
|---|---|---|---|---|---|
| Ex. 12 | A1/10 | I1/1.5 | C1/0.065 | 100 | 95 |
| Ex. 13 | A1/10 | I1/0.8 B2/0.7 | C1/0.065 | 100 | 95 |
| Ex. 14 | A1/10 | I1/0.8 B1/0.7 | C1/0.065 | 100 | 95 |
| Ex. 15 | A2/10 | I1/1.5 | C1/0.065 | 100 | 95 |
| Ex. 16 | A1/10 | I2/1.5 | C1/0.065 | 100 | 95 |
| Ex. 17 | A1/10 | I3/1.5 | C1/0.065 | 100 | 95 |
| Ex. 18 | A1/10 | I4/1.5 | C1/0.065 | 100 | 95 |
| Ex. 19 | A1/10 | I5/1.5 | C1/0.065 | 100 | 95 |
| Ex. 20 | A1/10 | I6/1.5 | C1/0.065 | 100 | 95 |
| Ex. 21 | A1/10 | I2/0.8 B2/0.7 | C1/0.065 | 100 | 95 |
| Ex. 22 | A1/10 | I3/0.8 B2/0.7 | C1/0.065 | 100 | 95 |
| Ex. 23 | A1/10 | I7/1.5 | C1/0.065 | 100 | 95 |

TABLE 6-continued

| Ex. No. | Resin (kind/amount (part)) | Acid generator (kind/amount (part)) | Quencher (kind/amount (part)) | PB (° C.) | PEB (° C.) |
|---|---|---|---|---|---|
| Ex. 24 | A1/10 | I8/1.5 | C1/0.065 | 100 | 95 |
| Ex. 25 | A1/10 | I9/1.5 | C1/0.065 | 100 | 95 |
| Ex. 26 | A1/10 | I10/1.5 | C1/0.065 | 100 | 95 |
| Ex. 27 | A1/10 | I11/1.5 | C1/0.065 | 100 | 95 |
| Ex. 28 | A2/10 | I7/0.8 B2/0.7 | C1/0.065 | 100 | 95 |
| Ex. 29 | A1/10 | I3/0.4 I7/0.4 B2/0.7 | C1/0.065 | 100 | 95 |
| Comp. Ex. 1 | A2/10 | B3/1.5 | C1/0.065 | 100 | 95 |

Silicon wafers (12 inches) were each coated with "ARC-29", which is an organic anti-reflective coating composition available from Nissan Chemical Industries, Ltd., and then baked at 205° C. for 60 seconds, to form a 780 Å-thick organic anti-reflective coating. Each of the photoresist compositions prepared as above was spin-coated over the anti-reflective coating so that the thickness of the resulting film became 85 nm after drying. The silicon wafers thus coated with the respective photoresist compositions were each prebaked on a direct hotplate at a temperature shown in the column "PB" in Table 6 for 60 seconds. Using an ArF excimer stepper for immersion exposure ("XT: 1900Gi" manufactured by ASML, NA=1.35, ¾ Annular, X-Y polarization), each wafer thus formed with the respective resist film was subjected to contact hole pattern exposure using a photomask for forming a contact hole pattern having a hole pitch of 100 nm and a hole diameter of 70 nm with the exposure quantity being varied stepwise. Ultrapure water was used as an immersion medium.

After the exposure, each wafer was subjected to post-exposure baking on a hotplate at a temperature shown in the column "PEB" in Table 6 for 60 seconds and then to paddle development for 60 seconds with an aqueous solution of 2.38% by mass tetramethylammonium hydroxide.

Each of patterns developed on the organic anti-reflective coating substrate after the development was observed with a scanning electron microscope, the results of which are shown in Table 7.

Effective sensitivity (ES): It was expressed as the amount of exposure that the hole diameter of the contact hole pattern became 55 nm after exposure and development.

CD uniformity (CDU): The photoresist pattern at ES was observed with a scanning electron microscope. The hole diameter of the contact hole pattern was twenty four times measured and its average diameter was calculated. The average diameters of four hundred holes on the same wafer were respectively measured. When population was the average diameters of four hundred holes, the standard deviation (CDU) was calculated. The smaller the standard deviation is, the better pattern profile is. When the standard deviation is less than 1.85 nm, CDU is very good and its evaluation is marked by "⊚ ⊚", when the standard deviation is 1.85 nm or more and less than 1.90 nm, CDU is good and its evaluation is marked by "⊚", when the standard deviation is 1.90 nm or more and less than 2.00 nm, CDU is usual and its evaluation is marked by "○", and when the standard deviation is more than 2.00 nm, CDU is bad and its evaluation is marked by "×". Further, each of the standard deviation is also shown in parentheses in a column of "CDU".

TABLE 7

| Ex. No. | CDU |
|---|---|
| Ex. 12 | ◎ (1.86) |
| Ex. 13 | ◎◎ (1.48) |
| Ex. 14 | ◎◎ (1.72) |
| Ex. 15 | ○ (1.98) |
| Ex. 16 | ◎◎ (1.79) |
| Ex. 17 | ◎◎ (1.82) |
| Ex. 18 | ○ (1.92) |
| Ex. 19 | ◎ (1.87) |
| Ex. 20 | ◎ (1.89) |
| Ex. 21 | ◎◎ (1.33) |
| Ex. 22 | ◎◎ (1.42) |
| Ex. 23 | ◎ (1.85) |
| Ex. 24 | ○ (1.90) |
| Ex. 25 | ○ (1.90) |
| Ex. 26 | ◎◎ (1.80) |
| Ex. 27 | ◎◎ (1.84) |
| Ex. 28 | ◎◎ (1.33) |
| Ex. 29 | ◎◎ (1.31) |
| Comp. Ex. 1 | X (2.64) |

The salt of the present invention is suitable for an acid generator and the photoresist composition comprising the salt of the present invention provides a good photoresist pattern having good CD uniformity.

What is claimed is:

1. A salt represented by the formula (I):

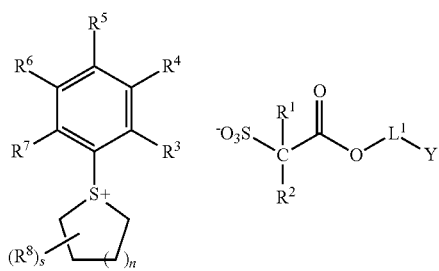

wherein $R^1$ and $R^2$ independently each represent a fluorine atom or a C1-C6 perfluoroalkyl group, $L^1$ represents a single bond, a C1-C6 alkanediyl group, a C4-C8 divalent alicyclic hydrocarbon group, —$(CH_2)_t$—CO—O—* or —$(CH_2)_t$—CO—O—$CH_2$—$(CH_2)_u$—*, one or more —$CH_2$— in the alkanediyl group and —$(CH_2)_u$— can be replaced by —O—, t represents an integer of 1 to 12, u represents an integer of 0 to 12, * represents a binding position to Y, Y represents a C3-C18 monovalent alicyclic hydrocarbon group which can have one or more substituents, one or more of —$CH_2$— groups in the monovalent alicyclic hydrocarbon group can be replaced by —O—, —CO— or —$SO_2$—, $R^3$, $R^4$, $R^5$, $R^6$ and $R^7$ each independently represent a hydrogen atom, a hydroxyl group, a C1-C6 alkyl group, a C1-C6 alkoxy group, a C2-C7 alkoxycarbonyl group or a C2-C12 acyloxy group, and one or more of —$CH_2$— groups in the alicycle containing $S^+$ have been replaced by —O— or —CO—, n represents an integer of 1 to 3, s represents an integer of 0 to 3, and $R^8$ is independently in each occurrence a C1-C6 alkyl group.

2. The salt according to claim 1, wherein $L^1$ is a single bond or a methylene group.

3. An acid generator comprising the salt according to claim 1.

4. A photoresist composition comprising the acid generator according to claim 3 and a resin having an acid-labile group, being insoluble or poorly soluble in an aqueous alkali solution but becoming soluble in an aqueous alkali solution by the action of an acid.

5. The photoresist composition according to claim 4, which further comprises a basic compound.

6. A process for producing a photoresist pattern comprising the following steps (1) to (5):
    (1) a step of applying the photoresist composition according to claim 4 on a substrate,
    (2) a step of forming a photoresist film by conducting drying,
    (3) a step of exposing the photoresist film to radiation,
    (4) a step of baking the exposed photoresist film, and
    (5) a step of developing the baked photoresist film with an alkaline developer, thereby forming a photoresist pattern.

7. An acid generator comprising the salt according to claim 2.

8. A process for producing a photoresist pattern comprising the following steps (1) to (5):
    (1) a step of applying the photoresist composition according to claim 5 on a substrate,
    (2) a step of forming a photoresist film by conducting drying,
    (3) a step of exposing the photoresist film to radiation,
    (4) a step of baking the exposed photoresist film, and
    (5) a step of developing the baked photoresist film with an alkaline developer, thereby forming a photoresist pattern.

* * * * *